(12) United States Patent
Hinderer et al.

(10) Patent No.: US 12,221,615 B2
(45) Date of Patent: Feb. 11, 2025

(54) GLP-1 AND USE THEREOF IN COMPOSITIONS FOR TREATING METABOLIC DISEASES

(71) Applicant: The Trustees of the University of Pennsylvania, Philadelphia, PA (US)

(72) Inventors: Christian Hinderer, Philadelphia, PA (US); James M. Wilson, Philadelphia, PA (US); Matthew Wilson, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 712 days.

(21) Appl. No.: 15/750,240

(22) PCT Filed: Aug. 5, 2016

(86) PCT No.: PCT/US2016/045696
§ 371 (c)(1),
(2) Date: Feb. 5, 2018

(87) PCT Pub. No.: WO2017/024198
PCT Pub. Date: Feb. 9, 2017

(65) Prior Publication Data
US 2018/0230488 A1     Aug. 16, 2018

Related U.S. Application Data

(60) Provisional application No. 62/356,289, filed on Jun. 29, 2016, provisional application No. 62/201,803, filed on Aug. 6, 2015.

(51) Int. Cl.
| | |
|---|---|
| *C12N 15/86* | (2006.01) |
| *A61K 38/26* | (2006.01) |
| *A61K 38/28* | (2006.01) |
| *A61K 48/00* | (2006.01) |
| *A61P 3/10* | (2006.01) |
| *C07K 14/00* | (2006.01) |
| *C07K 14/605* | (2006.01) |

(52) U.S. Cl.
CPC ............. *C12N 15/86* (2013.01); *A61K 38/26* (2013.01); *A61K 38/28* (2013.01); *A61K 48/00* (2013.01); *A61K 48/005* (2013.01); *A61K 48/0058* (2013.01); *A61P 3/10* (2018.01); *C07K 14/00* (2013.01); *C07K 14/605* (2013.01); *C12N 2750/14143* (2013.01); *C12N 2750/14171* (2013.01); *C12N 2800/22* (2013.01)

(58) Field of Classification Search
CPC .......... C12N 15/86; C12N 2750/14143; C12N 2750/14171; C12N 2800/22; C12N 9/644; C12N 15/88; C12N 2750/14141; C12N 2840/007; C07K 14/00; C07K 14/605; C07K 14/47; C07K 14/745; C07K 14/76; A61K 48/00; A61K 48/005; A61K 38/28; A61K 48/0058; A61K 38/26; A61P 3/10
See application file for complete search history.

(56) References Cited

U.S. PATENT DOCUMENTS

| | | | |
|---|---|---|---|
| 5,139,941 | A | 8/1992 | Muzyczka et al. |
| 5,478,745 | A | 12/1995 | Samulski et al. |
| 5,741,683 | A | 4/1998 | Zhou et al. |
| 6,057,152 | A | 5/2000 | Samulski et al. |
| 6,204,059 | B1 | 3/2001 | Samulski et al. |
| 6,268,213 | B1 | 7/2001 | Samulski et al. |
| 6,491,907 | B1 | 12/2002 | Rabinowitz et al. |
| 6,596,535 | B1 | 7/2003 | Carter |
| 6,660,514 | B1 | 12/2003 | Zolotukhin et al. |
| 6,951,753 | B2 | 10/2005 | Shenk et al. |
| 7,094,604 | B2 | 8/2006 | Snyder et al. |
| 7,125,717 | B2 | 10/2006 | Carter |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,282,199 | B2 | 10/2007 | Gao et al. |
| 7,439,065 | B2 | 10/2008 | Ferrari et al. |
| 7,456,683 | B2 | 11/2008 | Takano et al. |
| 7,588,772 | B2 | 9/2009 | Kay et al. |
| 7,790,449 | B2 | 9/2010 | Gao et al. |
| 7,906,111 | B2 | 3/2011 | Wilson et al. |

(Continued)

FOREIGN PATENT DOCUMENTS

| | | |
|---|---|---|
| EP | 1310571 | 5/2003 |
| WO | WO1987006941 A1 * | 11/1987 |

(Continued)

OTHER PUBLICATIONS

Korshidi et al. "Functional expression of the human coagulation factor IX using heterologous signal peptide and propeptide sequences in mammalian cell line." Biotechnol Lett. Sep. 2015;37(9):1773-81. Epub Jun. 24, 2015 (Year: 2015).*

(Continued)

*Primary Examiner* — Titilayo Moloye
(74) *Attorney, Agent, or Firm* — Howson & Howson LLP; Colleen M. Schaller

(57) ABSTRACT

Compositions and methods for treating type II diabetes in a subject. A viral vector is provided which includes a nucleic acid molecule comprising a sequence encoding a propeptide and the active portion of GLP-1, wherein, when expressed, the N-terminal amino acid of GLP-1 immediately follows the C-terminal amino acid of the propeptide. In desired embodiments, the subject is a cat or dog.

20 Claims, 6 Drawing Sheets
Specification includes a Sequence Listing.

(56) References Cited

U.S. PATENT DOCUMENTS

| | | | |
|---|---|---|---|
| 2003/0092013 A1* | 5/2003 | McCarthy | C12Q 1/6883 |
| | | | 435/6.11 |
| 2004/0143104 A1* | 7/2004 | Wadsworth | C07K 14/605 |
| | | | 530/399 |
| 2007/0036760 A1 | 2/2007 | Wilson et al. | |
| 2009/0197338 A1 | 8/2009 | Vandenberghe et al. | |
| 2011/0162096 A1* | 6/2011 | Cooper | C12N 15/8509 |
| | | | 800/14 |
| 2012/0137379 A1* | 5/2012 | Gao | C07K 14/005 |
| | | | 800/8 |
| 2012/0252732 A1 | 10/2012 | Ballance et al. | |
| 2012/0308540 A1 | 12/2012 | Madison et al. | |
| 2018/0009869 A1 | 1/2018 | Lu et al. | |
| 2018/0230488 A1 | 8/2018 | Hinderer et al. | |

FOREIGN PATENT DOCUMENTS

| | | | |
|---|---|---|---|
| WO | WO 2003/014318 | 2/2003 | |
| WO | WO 2003/030946 | 4/2003 | |
| WO | WO 2003/042397 | 5/2003 | |
| WO | WO 2005/033321 | 4/2005 | |
| WO | WO 2006/110689 | 10/2006 | |
| WO | WO 2011/126808 | 10/2011 | |
| WO | WO 2012/145523 | 10/2012 | |
| WO | WO 2013/049493 | 4/2013 | |
| WO | WO 2013/134881 | 9/2013 | |
| WO | WO-2013134881 A1 * | 9/2013 | ....... C07K 14/57563 |
| WO | WO 2014/052789 | 4/2014 | |
| WO | WO 2015/012924 | 1/2015 | |
| WO | WO 2020/139984 | 7/2020 | |

OTHER PUBLICATIONS

Tessitore et al. "205. AAV-Mediated Gene Transfer to Muscle and Liver of MPS VI Animal Models." Molecular Therapy, vol. 15, Supplement 1, 2007, p. S41, ISSN 1525-0016. (Year: 2007).*

Pontius et al. "Initial sequence and comparative analysis of the cat genome." Genome Res. 17:1675-1689(2007). (Year: 2007).*

Lindblad-Toh et al. "Genome sequence, comparative analysis and haplotype structure of the domestic dog." Nature vol. 438, pp. 803-819 (2005). (Year: 2005).*

Thiagarajan et al. "Thrombin." In: Encyclopedia of Life Sciences (ELS). John Wiley & Sons, Ltd: Chichester (2009) (Year: 2009).*

UniProtKB—M3WSI8 (M3WSI8_FELCA) (accessed May 22, 2021) (Year: 2021).*

UniProtKB—E2RRM2 (E2RRM2_CANLF) (accessed May 22, 2021) (Year: 2021).*

UniProtKB—P00734 (THRB_Human) (accessed May 22, 2021). (Year: 2021).*

Palta et al. "Overview of the coagulation system. "Indian J Anaesth. Sep.-Oct. 2014; 58(5): 515-523 (Year: 2014).*

Yu et al. "Synthetic fusion protein design and applications. "Biotechnol Adv . Jan.-Feb. 2015;33(1):155-164. (Year: 2015).*

Ke et al. "Secretion of functional a1-antitrypsin is cell type dependent: Implications for intramuscular delivery for gene therapy." Proc Natl Acad Sci U S A .Aug. 2, 2022;119(31): (Year: 2022).*

Communication pursuant to Article 94(3) EPC issued in European Patent Application No. 16833915.8, dated Nov. 20, 2020.

Buning H et al., Recent developments in adeno-associated virus vector technology, J. Gene Med, May 2008; 10(7):717-733.

Choi SH and Lee HC, Long-term, antidiabetogenic effects of GLP-1 gene therapy using a double-stranded, adeno-associated viral vector, Gene Therapy, Feb. 2011; 18:155-63.

Diehl KH et al., A good practice guide to the administration of substances and removal of blood, including routes and volumes, J. Applied Toxicology, Jan.-Feb. 2001; 21(1):15-23.

Fisher KJ et al. Transduction with recombinant adeno-associated virus for gene therapy is limited by leading-strand synthesis. J. Virol., Jan. 1996; 70:520-32.

Gaddy DF et al., dsAAV8-mediated gene transfer and b-cell expression of IL-4 and b-cell growth factors are capable of reversing early-onset diabetes in NOD mice, Gene Therapy, Aug. 2012; 19(8):791-9.

GenBank Accession No. AAA36501.1, protein Z [*Homo sapiens*] (revised Jun. 23, 2010).

GenBank Accession No. AAA60166.1, Protein C [*Homo sapiens*] (revised Jun. 23, 2010).

GenBank Accession No. AAA98726.1, factor IX [*Homo sapiens*] (revised Jan. 7, 2010).

GenBank Accession No. AAA98797.1, albumin [*Homo sapiens*] (revised Jun. 23, 2010).

GenBank Accession No. AAR26346.1, factor IX [Felis catus] (submitted Nov. 7, 2003).

GenBank Accession No. ABB02531.1, coagulation factor VII [Canis lupus familiaris] (revised Dec. 24, 2009).

GenBank Accession No. ACB87203.1, factor VII [*Homo sapiens*] (revised May 17, 2010).

GenBank Accession No. CAA05126.1, Protein C [Canis lupus familiaris] (revised Feb. 3, 2011).

GenBank Accession No. CAA59279.1, albumin precursor [Felis catus] (submitted Feb. 20, 1995).

GenBank Accession No. CAB64867.1, albumin [Canis lupus familiaris] (revised Feb. 3, 2011).

Grieger JC and RJ Samulski., Adeno-associated virus as a gene therapy vector: Vector development, production and clinical applications, Adv. Biochem. Eng. Biotechnol., Oct. 2005; 99:119-45.

Ma M et al., Calpastatin overexpression protects axonal transport in an in vivo model of traumatic axonal injury, J Neurotrauma, Nov. 2012; 29(16):2555-63. (Epub Aug. 29, 2012).

McCarty DM et al., Self-complementary recombinant adeno-associated virus (scAAV) vectors promote efficient transduction independently of DNA synthesis, Gene Therapy, Aug. 2001; 8(16):1248-54.

Miyatake S et al., Transcriptional targeting of herpes simples virus for cell-specific replication, J. Virol., Jul. 1997; 71(7):5124-32.

NCBI Reference Sequence: NP_001009377.1, coagulation factor IX precursor [Felis catus] (submitted Feb. 20, 1995).

NCBI Reference Sequence: XP_003980582.1, coagulation factor VII [Felis catus] (revised Feb. 10, 2015).

NCBI Reference Sequence: XP_003993267.1, prothrombin [Felis catus] (revised Feb. 10, 2015).

NCBI Reference Sequence: XP_011284289.1, vitamin K-dependent protein S, partial [Felis catus] (revised Feb. 10, 2015).

NCBI Reference Sequence: NM_001003044.1, Canis lupus familiaris glucagon (GCG), mRNA (revised Sep. 26, 2013).

NCBI Reference Sequence: NP_000124.1, coagulation factor IX preproprotein [*Homo sapiens*] (revised Mar. 15, 2015).

NCBI Reference Sequence: NP_000497.1, prothrombin preproprotein [*Homo sapiens*] (revised Mar. 15, 2015).

NCBI Reference Sequence: NP_001003323.1, coagulation factor IX preproprotein [Canis lupus familiaris] (revised May 25, 2014).

NCBI Reference Sequence: NP_062562.1, coagulation factor VII isoform b preproprotein [*Homo sapiens*] (revised Mar. 15, 2015).

NCBI Reference Sequence: XM_006935320.1, Felis catus glucagon (GCG), mRNA (revised Feb. 10, 2015).

NCBI Reference Sequence: XP_003639742.1, prothrombin-like [Canis lupus familiaris] (revised Dec. 2, 2011).

NCBI Reference Sequence: XP_005639500.1, vitamin K-dependent protein S [Canis lupus familiaris] (revised Sep. 24, 2013).

NCBI Reference Sequence: XP_011283508.1, vitamin K-dependent protein C [Felis catus] (revised Feb. 10, 2015).

Sandig V et al., HBV-derived promoters direct liver-specific expression of an adenovirally transduced LDL receptor gene, Gene Ther., Nov. 1996; 3(11):1002-9.

Thompson JD et al., A comprehensive comparison of multiple sequence alignments, Nucl. Acids. Res., Jul. 1, 1999; 27(13):2682-90.

Tian S et al., FurinDB: A database of 20-residue furin cleavage site motifs, substrates and their associated drugs, Int. J. Mol. Sci, Feb. 2011; 12(2):1060-5.

UniProtKB: P07225, PROS1 sequence (last modified Apr. 1, 1988).

(56) References Cited

OTHER PUBLICATIONS

Zhang H et al., Adenovirus-adeno-associated virus hybrid for large-scale recombinant adeno-associated virus production, Human Gene Therapy, Sep. 2009; 20:922-9.
International Search Report and Written Opinion mailed Oct. 31, 2016 in International Patent Application No. PCT/US2016/045696.
Riedel et al., DsAAV8-mediated expression of glucagon-like peptide-1 in pancreatic beta-cells ameliorates streptozotocin-induced diabetes, Gene Therapy, vol. 17(2): 171-180, Feb. 2010.
Examination Report issued Jan. 30, 2020 in European Patent Application No. 16833915.8.
Response to Examination Report in European Patent Application No. 16833915.8, filed Jul. 29, 2020.
Office Action dated Jul. 1, 2020 issued in Japanese Patent Application No. 2018-506330.
Communication pursuant to Article 94(3) EPC issued in European Patent Application No. 16833915.8, dated Jul. 12, 2022.
Gilor et al., New Approaches to Feline Diabetes Mellitus: Glucagon-like peptide-1 analogs. J Feline Med Surg. Sep. 2016; 18(9):733-43.
Partial European Search Report dated Nov. 26, 2024 issued in European Patent Application No. 21862600.0.

\* cited by examiner

GLP1 in cats (capsid and dose comparison)

ic form herewith. This file is
GLP-1 AND USE THEREOF IN COMPOSITIONS FOR TREATING METABOLIC DISEASES

INCORPORATION-BY-REFERENCE OF MATERIAL SUBMITTED IN ELECTRONIC FORM

Applicant hereby incorporates by reference the Sequence Listing material filed in electronic form herewith. This file is labeled "15-7471_Seq_Listing_ST25".

BACKGROUND OF THE INVENTION

One in 400 cats and 1 in 500 dogs in the U.S. have a condition similar to Type II diabetes (T2DM) in humans. The current standard of care is twice daily insulin injections by the owner along with frequent veterinarian visits and disposable diagnostics that are both expensive, time consuming and inconvenient for the owners of these animals.

Glucagon-like peptide 1 (GLP-1) is an endogenous peptide hormone that plays a central role in glucose homeostasis. GLP-1 analogs are currently used as common human therapeutic hormones for the treatment of diabetes. GLP-1 has the ability to control hyperglycemia by potentiating insulin release, increasing insulin sensitivity, preventing beta cell loss, and delaying gastric emptying. However, because of its short half-life in circulation, it is difficult to develop GLP-1 as a standalone therapeutic without stable vector mediated delivery. GLP-1 analogues engineered to overcome the short half-life of the native hormone have emerged as important therapeutics for the treatment of T2DM. However, these drugs still require frequent subcutaneous injections. An alternative approach to achieve sustained therapeutic levels of GLP-1 is through continuous in vivo production of the native peptide using gene transfer mediated by an adeno-associated virus or other viral or non-viral vector. GLP-1 is an ideal candidate for this method of delivery due to its short half-life, wide therapeutic index, and the safety of long term exposure. This approach could provide a convenient and effective therapy for T2DM in both humans and other species affected by the disease.

GLP-1 cannot be expressed in its native form from a gene therapy vector due to the need for cell-specific proteases to release the active peptide from the precursor polypeptide. Attempts to simply express the peptide alone with a signal peptide to direct secretion have failed, possibly due to the inefficient translation and secretion of small proteins, or inefficient cleavage of the signal peptide to generate active GLP-1. In previous rodent studies of vector-mediated GLP-1 expression, effective circulating levels of GLP-1 were only achieved when the peptide was expressed in the context of a larger, non-species-specific propeptide followed influenza hemagglutinin and a cleavage site immediately preceding the GLP-1 N-terminus. See, e.g., Gaddy et al, dsAAV8-mediated gene transfer and b-cell expression of IL-4 and b-cell growth factors are capable of reversing early-onset diabetes in NOD mice, Gene Therapy, 19:791-9 (2012) and Choi and Lee, Long-term, antidiabetogenic effects of GLP-1 gene therapy using a double-stranded, adeno-associated viral vector, Gene Therapy, 18:155-63 (2011), which are incorporated herein by reference. However, these foreign propeptides have the potential to illicit destructive immune responses against transduced cells. Therefore, compositions useful for effectively treating Type II diabetes in subjects, particularly companion animals, are needed.

SUMMARY OF THE INVENTION

Novel engineered glucagon-like peptide 1 (GLP-1) constructs are provided herein. The GLP-1 proteins expressed from these constructs are suitably characterized by increased circulating half-life, as compared to GLP-1 protein given as a standalone therapeutic, and are effectively processed to release the active portion of GLP-1 in vivo. These constructs can be delivered to subjects in need thereof via a number of routes, and particularly by expression in vivo mediated by a recombinant vector such as a recombinant adeno-associated virus (rAAV) vector.

In some embodiments, a viral vector comprising a GLP-1 construct is provided. In some embodiments, the GLP-1 construct encodes a propeptide and the active portion of GLP-1, wherein, when expressed, the N-terminal amino acid of GLP-1 immediately follows the C-terminal amino acid of the propeptide.

In some embodiments, the propeptide is an endogenous sequence. That is, the propeptide sequence is derived from the same subject species for which administration is ultimately intended.

In some embodiments, the propeptide is a leader sequence derived from a coagulation factor. In one embodiment, the propeptide sequence is a leader sequence selected from protein S, factor IX, albumin, albumin, IL2, thrombin, and mannosidase. In another embodiment, the propeptide includes a furin site.

In some embodiments, the GLP-1 construct encodes the GLP-1 sequence corresponding to the active portion of GLP-1. In one embodiment, the GLP-1 sequence encodes amino acids 7-37 of GLP-1. In another embodiment, the GLP-1 sequence is SEQ ID NO: 1. In one embodiment of, the GLP-1 construct encodes the amino acid sequence set forth in SEQ ID NO: 5. In one embodiment, the nucleic acid sequence encoding the GLP-1 construct is set forth in SEQ ID NO: 6. In yet another embodiment, the GLP-1 construct is a codon optimized sequence encoding SEQ ID NO: 5.

In some embodiments, the recombinant vectors provided herein have an expression cassette comprising the propeptide and GLP-1. In some embodiments, the expression cassette comprises a promoter which specifically directs expression of the GLP-1 in liver cells.

In some embodiments, the recombinant vector is a recombinant adeno-associated virus (rAAV) vector. In some embodiments, the rAAV has a capsid selected from AAV8, AAVrh64R1, AAV9, AAVhu.37 or AAVrh10. In a particular embodiment, an rAAV vector is provided that has an expression cassette comprising a propeptide and the active portion of GLP-1. In a specific embodiment, the propeptide comprises a coagulation factor IX leader sequence. In another embodiment, the GLP-1 sequence encodes aa 7-37 of GLP-1. In another embodiment, the rAAV vector comprises an expression cassette comprising a promoter which specifically directs expression of the GLP-1 construct in liver cells.

In some embodiments, a pharmaceutical composition comprising a pharmaceutically acceptable carrier and a recombinant vector as described herein is provided. Also provided are methods for treating T2DM by administering to a subject in need thereof a recombinant vector described herein that has an expression cassette, wherein said expression cassette further comprises regulatory control sequences which direct expression of the GLP-1 construct in the subject. In some embodiments, the subject being treated is a companion animal. In one embodiment, the subject is a feline. In another embodiment, the subject is a canine. As used herein, the terms "patient" and "subject" are used interchangeably, and can refer to a human or veterinary subject.

In yet another embodiment, methods for increasing the circulating half-life of GLP-1 in a subject comprising providing recombinant vector described herein that has an expression cassette encoding an endogenous propeptide and the active portion of GLP-1, wherein, when expressed, the N-terminal amino acid of GLP-1 immediately follows the C-terminal amino acid of the propeptide.

The recombinant vectors described above can be used in a regimen for treating type II diabetes.

Other aspects and advantages of the invention will be readily apparent from the following detailed description of the invention.

DETAILED DESCRIPTION OF THE INVENTION

Figure 1:
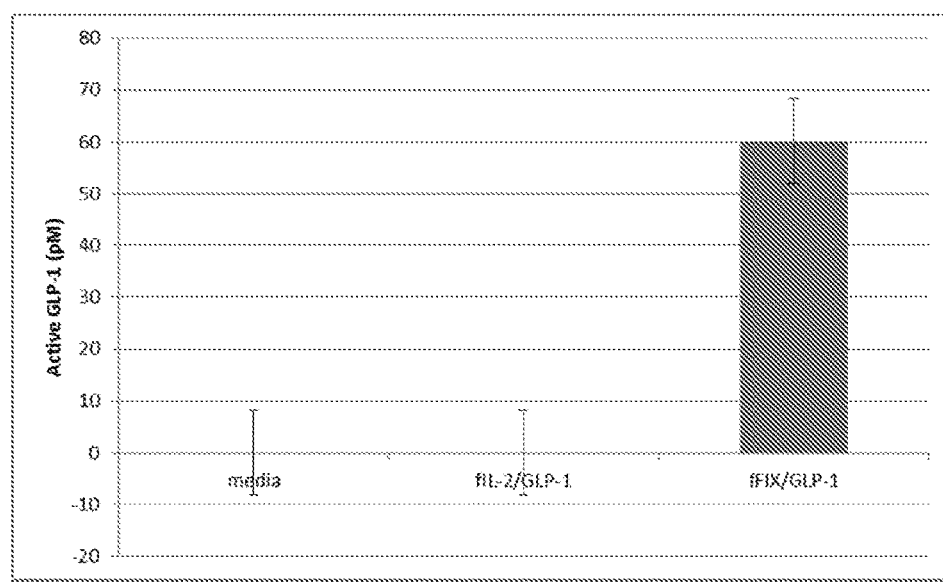
FIG. 1 provides the results of in vitro evaluation of active GLP-1 expression in transfected HEK293 cells, as described in Example 2. Bar on the left corresponds to a media-only control. Bar in the middle corresponds to a GLP-1 construct containing an interleukin-2 signal peptide followed by GLP-1 (7-37), as described in Example 1. Bar on the right corresponds to GLP-1 construct containing a factor IX propeptide followed by GLP-1 (7-37), as described in Example 1. Values are mean+/−SEM of replicate wells.

GLP-1 expression constructs have been developed for use in subjects including companion animals and humans, in which the leader propeptide is derived from proteins endogenous to the species of the veterinary or human patient. Desirably, following cleavage and secretion, all products produced from the construct, i.e., the free propeptide and active GLP-1, are non-immunogenic self-peptides.

The GLP-1 constructs described herein are characterized in that they provide an increased half-life of circulating GLP-1 as compared to administration of the GLP-1 peptide as a stand-alone therapeutic. This is due to the continued expression of the expression cassette contained within the vector, in combination with correct processing of the N-terminus of the GLP-1 active peptide.

Delivery of these constructs to subjects in need thereof via a number of routes, and particularly by expression in vivo mediated by a recombinant vector such as a rAAV vector, is described. Also provided are methods of using these constructs in regimens for treating T2DM or metabolic syndrome in a subject in need thereof and increasing the half-life of GLP-1 in a subject. In addition, methods are provided for enhancing the activity of GLP-1 in a subject. Also provided are methods for inducing weight loss in a subject in need thereof.

Glucagon-like peptide 1, or GLP-1, is an incretin derived from the transcription product of the proglucagon gene. In vivo, the glucagon gene expresses a 180 amino acid prepropolypeptide that is proteolytically processed to form glucagon, two forms of GLP-1 and GLP-2. The original sequencing studies indicated that GLP-1 possessed 37 amino acid residues. However, subsequent information showed that this peptide was a propeptide and was additionally processed to remove 6 amino acids from the amino-terminus to a form GLP-1(7-37), an active form of GLP-1. The glycine at position 37 is also transformed to an amide in vivo to form GLP-1 (7-36) amide. GLP-1 (7-37) and GLP-1 (7-36) amide are insulinotropic hormones of equal potency. Thus, as used herein, the biologically "active" forms of GLP-1 which are useful herein are: GLP-1-(7-37) and GLP-1-(7-36)NH$_2$.

For convenience, the sequence of "wild-type" GLP-1 (7-37), i.e., the native sequence of human GLP-1, is shown in SEQ ID NO: 1: HAEGTFTSDV SSYLEGQAAK EFIAWLVKGR G. This wild-type amino acid sequence was utilized in the examples below and is conserved across various species, including human, cat and dog. However, as used herein, the term GLP-1 refers to any of the active forms of GLP-1, e.g., GLP-1 (7-37) or GLP-1 (7-36) amide. In addition, in one embodiment, the term GLP-1 refers to functional variants of the GLP-1 peptide. Functional variants include homologs derived from different species. The N-terminus (active portion) of GLP-1 and its family peptides share a high degree of sequence identity. However, some variation amongst GLP-1 proteins is seen across species, especially in the bolded residues below:

HAEGTFTSDVSSYLEGQAAK EFIAWLVKGRG

In one embodiment, functional variants of GLP-1 include variants which may include up to about 10% variation from a GLP-1 nucleic acid or amino acid sequence described herein or known in the art, which retain the function of the wild type sequence. As used herein, by "retain function" it is meant that the nucleic acid or amino acid functions in the same way as the wild type sequence, although not necessarily at the same level of expression or activity. For example, in one embodiment, a functional variant has increased expression or activity as compared to the wild type sequence. In another embodiment, the functional variant has decreased expression or activity as compared to the wild type sequence. In one embodiment, the functional variant has 10%, 20%, 30%, 40%, 50%, 60%, 70%, 80%, 90% or greater increase or decrease in expression or activity as compared to the wild type sequence.

In another embodiment, functional variants of GLP-1 include variants which may include up to about 20% variation from a GLP-1 nucleic acid or amino acid sequence described herein or known in the art, which retain the function of the wild type sequence.

In one embodiment, functional variants of GLP-1 include variants which may include up to about 30% variation from a GLP-1 nucleic acid or amino acid sequence described herein or known in the art, which retain the function of the wild type sequence.

In one embodiment, the term GLP-1 refers to active GLP-1 in which one or more amino acid substitutions have been made, as compared to the sequence produced above (SEQ ID NO: 1). In one embodiment, one or more amino acid substitutions are made in a residue in which variation is shown across species (i.e., the bolded residues above). In another embodiment, one or more amino acid substitutions are made in a residue in which conservation is shown across species. Although GLP-1 shares a high degree of identity across species, it may be desirable to select the GLP-1 sequence based on the species of the subject for which administration of the vector is ultimately intended. In one example, the subject is a mammal. For example, in one embodiment, if the subject is a feline, the GLP-1 sequence is derived from a feline protein. In another embodiment, the GLP-1 sequence is derived from a canine protein. In yet another embodiment, the GLP-1 sequence is derived from a human protein. In another embodiment, the GLP-1 sequence is derived from a non-human primate protein. In another embodiment, the GLP-1 is derived from bovine, ovine, or porcine protein. In yet another embodiment, the GLP-1 is derived from a rodent. In one embodiment, the GLP-1 sequence encodes GLP-1 (7-37). In another embodiment, the GLP-1 sequence is SEQ ID NO: 1. In another embodiment, the GLP-1 sequence is aa 1-29 of SEQ ID NO:1 (which corresponds to aa 7-36 of wild-type GLP-1).

As used herein, the terms "derived" or "derived from" mean the sequence or protein is sourced from a specific subject species or shares the same sequence as a protein or sequence sourced from a specific subject species. For example, a propeptide sequence which is "derived from" a canine, shares the same sequence (or a variant thereof, as defined herein) as the same propeptide sequence as expressed in a canine. However, the specified nucleic acid or amino acid need not actually be sourced from a canine. Various techniques are known in the art which are able to produce a desired sequence, including mutagenesis of a similar protein (e.g., a homolog) or artificial production of a nucleic acid or amino acid sequence. The "derived" nucleic acid or amino acid retains the function of the same nucleic acid or amino acid in the species from which it is "derived", regardless of actual source of the derived sequence.

As used herein the terms "GLP-1 construct", "GLP-1 expression construct" and synonyms include the GLP-1 sequence as described herein in combination with a propeptide sequence. The terms "GLP-1 construct", "GLP-1 expression construct" and synonyms can be used to refer to the nucleic acid sequences encoding the propeptide and GLP-1 or the expression products thereof.

The GLP-1 constructs described herein also include a propeptide sequence. As used herein, the terms leader sequence, propeptide, signal sequence, prepeptide and similar synonyms refer to the sequence which is cleaved from the final active GLP-1 peptide in vivo. Such "propeptide" sequence may include more than one such sequence, e.g., a signal sequence and a propeptide sequence. Although endogenous GLP-1 is expressed as a prohormone (proglucagon, which is cleaved into the active form of GLP-1), desirably, the propeptide used in the constructs described herein is a leader sequence which is derived from a protein heterologous to GLP-1.

In one embodiment, the propeptide is derived from the same species for which administration is ultimately intended. For example, in one embodiment, the desired subject is a feline, and the propeptide sequence is derived from a feline protein. In another embodiment, the propeptide sequence is derived from a canine protein. In yet another embodiment, the propeptide sequence is derived from a human protein. In another embodiment, the propeptide sequence is derived from a non-human primate protein. In another embodiment, the propeptide is derived from bovine, ovine, or porcine protein. In yet another embodiment, the propeptide is derived from a rodent protein.

The length of the propeptide can be varied and/or selected in order to enhance expression of the GLP-1 construct in vivo. Thus, the endogenous propeptide can be selected for its desirable length, or a desired propeptide may be engineered to result in a propeptide which retains the function of the wild type propeptide, but at a more desirable sequence length.

Desirably, the propeptide adds at least about 19 amino acids to the length of GLP1, making the ultimate propeptide-GLP-1 expression product at least about 45-50 amino acids in length. In one embodiment, the propeptide is at least about 35 amino acids in length, making the ultimate propeptide-GLP-1 expression product at least about 65 amino acids in length. Because of these size requirements, albumin and clotting factors are desirable sources of the propeptide. Mutants and variants of these propeptides, as described herein, are also useful in the compositions and method described herein. In particular, N-terminally truncated fragments (i.e., retaining the C-terminal portion) of the propeptides described herein are useful provided they retain the cleavage signal required for proper processing of the expression product into active GLP-1.

In one embodiment, functional variants of the desired propeptide include variants which may include up to about 10% variation from a propeptide nucleic acid or amino acid sequence described herein or known in the art, which retain the function of the wild type sequence. As used herein, by "retain function" it is meant that the nucleic acid or amino acid functions in the same way as the wild type sequence, although not necessarily at the same level of expression or activity. For example, in one embodiment, a functional variant has increased expression or activity as compared to the wild type sequence. In another embodiment, the functional variant has decreased expression or activity as compared to the wild type sequence. In one embodiment, the functional variant has 10%, 20%, 30%, 40%, 50%, 60%, 70%, 80%, 90% or greater increase or decrease in expression or activity as compared to the wild type sequence.

In another embodiment, functional variants of the desired propeptide include variants which may include up to about 20% variation from a propeptide nucleic acid or amino acid sequence described herein or known in the art, which retain the function of the wild type sequence.

In another embodiment, functional variants of the desired propeptide include variants which may include up to about 30% variation from a propeptide nucleic acid or amino acid sequence described herein or known in the art, which retain the function of the wild type sequence.

In one embodiment, the propeptide sequence is combined with an additional sequence to increase the efficiency of N-terminal processing. In one embodiment, the propeptide sequence is combined with a furin cleavage site. In one embodiment, the furin sequence comprises the RX[R/K]R consensus sequence. In another embodiment, the furin sequence comprises the sequence RKRR. The furin site may be modified by the person of skill in the art. See, Tian et al, Int. J. Mol. Sci, 2011, 12:1010-5 for a discussion of FurinDB, a database containing experimentally verified furin cleavage sites, substrates, species, experimental methods, original publications of experiments and associated drugs targeting furin substrates, which document is incorporated herein by reference.

In one embodiment, the propeptide is a Factor IX propeptide. In another embodiment, the propeptide is factor II propeptide. In another embodiment, the propeptide is factor VII propeptide. In another embodiment, the propeptide is factor X propeptide. In another embodiment, the propeptide is a protein C propeptide. In another embodiment, the propeptide is a protein S propeptide. In another embodiment, the propeptide is an albumin propeptide. In another embodiment, the propeptide is a mannosidase propeptide. In another embodiment, the propeptide is derived from a bone "gla" protein. In one embodiment, the propeptide is at least about 19-100 amino acids in length, inclusive, including any integer therebetween. In another embodiment, the propeptide is about 25 amino acids in length. In another embodiment, the propeptide is about 35 amino acids in length. In another embodiment, the propeptide is about 40 amino acids in length. In another embodiment, the propeptide is about 40 amino acids in length. In another embodiment, the propeptide is about 45 amino acids in length. In another embodiment, the propeptide is about 50 amino acids in length. In another embodiment, the propeptide is about 55 amino acids in length. In another embodiment, the propeptide is about 60 amino acids in length. In another embodiment, the propeptide is about 65 amino acids in length. In another embodiment, the propeptide is about 70 amino acids in length. In another embodiment, the propeptide is about 75 amino acids in length. In another embodiment, the propeptide is about 80, 85, 90, 95 or 100 amino acids in length. In one embodiment, the propeptide is 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49 amino acids in length.

The term "amino acid substitution" and its synonyms are intended to encompass modification of an amino acid sequence by replacement of an amino acid with another, substituting, amino acid. The substitution may be a conservative substitution. It may also be a non-conservative substitution. The term conservative, in referring to two amino acids, is intended to mean that the amino acids share a common property recognized by one of skill in the art. For example, amino acids having hydrophobic nonacidic side chains, amino acids having hydrophobic acidic side chains, amino acids having hydrophilic nonacidic side chains, amino acids having hydrophilic acidic side chains, and amino acids having hydrophilic basic side chains. Common properties may also be amino acids having hydrophobic side chains, amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Methods for replacing an amino acid are well known to the skilled in the art and include, but are not limited to, mutations of the nucleotide sequence encoding the amino acid sequence. Reference to "one or more" herein is intended to encompass the individual embodiments of, for example, 1, 2, 3, 4, 5, 6, or more.

In another embodiment, the GLP-1 peptide or propeptide includes variants which may include up to about 10% variation from the GLP-1 sequence or a propeptide sequence, as those terms are described herein. That is, the GLP-1 peptide or propeptide shares about 90% identity to about 99.9% identity, about 95% to about 99% identity or about 97% to about 98% identity to the GLP-1 or propeptide sequences provided herein and/or known in the art.

In addition to the GLP-1 peptides and propeptides provided herein, nucleic acid sequences encoding these peptides are provided. In one embodiment, a nucleic acid sequence is provided which encodes for the GLP-1 peptides described herein. In another embodiment, this includes any nucleic acid sequence which encodes the GLP-1 sequence of SEQ ID NO: 1. The wild type nucleic acid sequence of GLP-1 (7-37) is provided in SEQ ID NO: 56. The sequence of feline glucagon is known and can be found, e.g., as NCBI Reference Sequence: XM_006935320.1. The sequence of canine glucagon is known and can be found, e.g, as NCBI Reference Sequence: NM_001003044.1. In one embodiment, the nucleic acid sequence encoding GLP-1 is a codon optimized sequence encoding any of the GLP-1 peptides described herein. In one embodiment, the codon optimized sequence shares at least about 60% identity with a GLP-1 nucleic acid sequence know in the art or described herein. In one embodiment, the codon optimized sequence shares at least about 70% identity with a GLP-1 nucleic acid sequence know in the art or described herein. In one embodiment, the codon optimized sequence shares at least about 80% identity with a GLP-1 nucleic acid sequence know in the art or described herein. In one embodiment, the codon optimized sequence shares at least about 90% identity with a GLP-1 nucleic acid sequence know in the art or described herein. In one embodiment, the GLP-1 sequence is optimized for expression in feline. In one embodiment, the nucleic acid sequence of GLP-1 (7-37) is provided in SEQ ID NO: 2. In another embodiment, a nucleic acid sequence is provided which encodes for any of the propeptide sequences described herein. In one embodiment, the nucleic acid sequence encodes a factor IX propeptide sequence. In another embodiment, the nucleic acid sequence encoding the feline factor IX propeptide sequence is SEQ ID NO: 4.

In one embodiment the propeptide and GLP-1 peptide are arranged such that, when the products are expressed, the N-terminal amino acid residue of the GLP-1 peptide immediately follows the C-terminal amino acid residue of the propeptide without any additional residues between. Thus, desirably, the coding regions for both the propeptide and GLP-1 peptide are incorporated into a single nucleic acid sequence without a linker between the coding sequences of the propeptide and GLP-1.

When a variant or fragment of the GLP-1 peptide and/or propeptide is desired, the coding sequences for these peptides may be generated using site-directed mutagenesis of the wild-type nucleic acid sequence. Alternatively or additionally, web-based or commercially available computer programs, as well as service based companies may be used to back translate the amino acids sequences to nucleic acid coding sequences, including both RNA and/or cDNA. See, e.g., backtranseq by EMBOSS, http://www.ebi.ac.uk/Tools/st/; Gene Infinity (http://www.geneinfinity.org/sms-/sms_backtranslation.html); ExPasy (http://www.expasy.org/tools/). In one embodiment, the RNA and/or cDNA coding sequences are designed for optimal expression in the subject species for which administration is ultimately intended, as discussed herein. Thus, in one embodiment, the coding sequences are designed for optimal expression in a feline. Thus, in another embodiment, the coding sequences are designed for optimal expression in a canine. Thus, in one embodiment, the coding sequences are designed for optimal expression in a human. Thus, in one embodiment, the coding sequences are designed for optimal expression in a primate. In another embodiment, the coding sequences are designed for optimal expression in an ovine, bovine or porcine. In another embodiment, the coding sequences are designed for optimal expression in a rodent.

The coding sequences may be designed for optimal expression using codon optimization. Codon-optimized coding regions can be designed by various different methods. This optimization may be performed using methods which are available on-line, published methods, or a company which provides codon optimizing services. One codon optimizing method is described, e.g., in International Patent Application Pub. No. WO 2015/012924, which is incorporated by reference herein. Briefly, the nucleic acid sequence encoding the product is modified with synonymous codon sequences. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

The terms "percent (%) identity", "sequence identity", "percent sequence identity", or "percent identical" in the context of nucleic acid sequences refers to the bases in the two sequences which are the same when aligned for correspondence. The length of sequence identity comparison may be over the full-length of the genome, the full-length of a gene coding sequence, or a fragment of at least about 100 to 150 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 70 amino acids to about 100 amino acids, or a peptide fragment thereof or the corresponding nucleic acid sequence coding sequencers. A suitable amino acid fragment may be at least about 8 amino acids in length, and may be up to about 150 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

Various combinations of propeptide and GLP-1 sequences can be made in accordance with the teachings herein to produce desirable GLP-1 expression constructs. This includes combinations of propeptide sequence which are known in the art with GLP-1 active peptide sequences as described herein.

In some embodiments, the use of coagulation factor propeptides is desirable. The propeptide portions of the vitamin k-dependent plasma proteins are highly conserved. See, Hemostasis and Thrombosis: Basic Principles and Clinical Practice, Colman, Ed., 1827 pp., illustrated. Philadelphia, Lippincott Williams & Wilkins, 2006.

In one embodiment, the propeptide sequence is a factor IX sequence. In another embodiment, the propeptide sequence includes a factor IX sequence in combination with a furin site. As demonstrated in the examples below, and in one embodiment, the propeptide sequence is a feline (*Felis catus*) factor IX leader sequence combined with the GLP-1(7-37) wild type sequence. In one embodiment, the factor IX leader sequence includes the signal and activation sequences (pro-sequence) and is about 46 amino acids long.

In one embodiment of, the GLP-1 construct encodes the amino acid sequence set forth in SEQ ID NO: 5. In one embodiment, the nucleic acid sequence encoding the GLP-1 construct is set forth in SEQ ID NO: 6. In yet another embodiment, the GLP-1 construct is a codon optimized sequence encoding SEQ ID NO: 5. The amino acid sequence of feline Factor IX is known and can be found at: GenBank accession no. AAR26346.1 which is reproduced in SEQ ID NO: 11 for convenience. In another embodiment, the propeptide sequence is a canine (*Canis lupis familiaris*) factor IX leader sequence combined with the GLP-1(7-37) wild type sequence. The amino acid sequence of canine Factor IX is known and can be found at: NCBI Reference Sequence: NP_001003323.1, which is reproduced in SEQ ID NO: 12 for convenience. In one embodiment, the propeptide sequence is amino acids 1-39 of SEQ ID NO: 12. In another embodiment, the GLP-1 construct sequence encodes the amino acid sequence set forth in SEQ ID NO: 13. In yet another embodiment, the GLP-1 construct is a codon optimized sequence encoding SEQ ID NO: 13. In another embodiment, the propeptide sequence is a human factor IX leader sequence combined with the GLP-1(7-37) wild type sequence. The amino acid sequence of human Factor IX is known and can be found, e.g. at: NCBI Reference Sequence: AAA98726.1, which is reproduced in SEQ ID NO: 14 for convenience. In one embodiment, the propeptide sequence is amino acids 1-46 of SEQ ID NO: 14. In another embodiment, the GLP-1 construct sequence encodes the amino acid sequence set forth in SEQ ID NO: 15. In yet another embodiment, the GLP-1 construct is a codon optimized sequence encoding SEQ ID NO: 15. Similar constructs can be made using other isoforms of Factor IX known in the art.

In another embodiment, the propeptide sequence is a Factor VII sequence. In another embodiment, the propeptide sequence includes a factor VII sequence in combination with a furin site. In one embodiment, the factor VII leader sequence includes the signal and activation sequences (pro-sequence) and is about 37-40 amino acids long. In another embodiment, the propeptide sequence is a feline (*felis catus*) factor VII leader sequence combined with the GLP-1(7-37) wild type sequence. The amino acid sequence of feline Factor VII is known and can be found at: GenBank accession no. XP_003980582.1 which is reproduced in SEQ ID NO: 16 for convenience. In one embodiment, the propeptide sequence is amino acids 1-40 of SEQ ID NO: 16. In one embodiment of, the GLP-1 construct encodes the amino acid sequence set forth in SEQ ID NO: 17. In yet another embodiment, the GLP-1 construct is a codon optimized sequence encoding SEQ ID NO:17. In another embodiment, the GLP-1 construct sequence is a canine factor VII leader sequence combined with the GLP-1(7-37) wild type sequence. The amino acid sequence of canine Factor VII is known and can be found at: NCBI Reference Sequence: ABB02531.1, which is reproduced in SEQ ID NO: 18 for convenience. In one embodiment, the propeptide sequence is amino acids 1-40 of SEQ ID NO: 18. In another embodiment, the GLP-1 construct sequence encodes the amino acid sequence set forth in SEQ ID NO: 19. In yet another embodiment, the GLP-1 construct is a codon optimized sequence encoding SEQ ID NO: 19. In another embodiment, the GLP-1 construct sequence is a human factor VII leader sequence combined with the GLP-1(7-37) wild type sequence. The amino acid sequence of human Factor VII is known and can be found, e.g. at: NCBI Reference Sequence: ACB87203.1, which is reproduced in SEQ ID NO: 20 for convenience. In one embodiment, the propeptide sequence is amino acids 1-60 of SEQ ID NO: 20. In another embodiment, the GLP-1 construct sequence encodes the amino acid sequence set forth in SEQ ID NO: 21. In yet another embodiment, the GLP-1 construct is a codon optimized sequence encoding SEQ ID NO: 21. An alternate form of human Factor VII, having a leader sequence of 38 aa, is sometimes called variant 2. This variant 2 lacks an exon in the 5' coding region, but maintains the reading frame, compared to variant 1. The encoded isoform (b) is shorter than isoform (a). The amino acid sequence of human Factor VII, variant 2 is known and can be found, e.g. at: NCBI Reference Sequence: NP_062562.1, which is reproduced in SEQ ID NO: 22 for convenience. In one embodiment, the propeptide sequence is amino acids 1-38 of SEQ ID NO: 22. In another embodiment, the GLP-1 construct sequence encodes the amino acid sequence set forth in SEQ ID NO: 23. In yet another embodiment, the GLP-1 construct is a codon optimized sequence encoding SEQ ID NO: 23. Similar constructs can be made using other isoforms of Factor VII known in the art.

Anticoagulant factor II is also called prothrombin. As used herein, factor II is used interchangeably with prothrombin and thrombin. In one embodiment, the propeptide sequence is a factor II leader sequence. In another embodiment, the propeptide sequence includes a factor II (thrombin) sequence in combination with a furin site. In one embodiment, the propeptide is about 41-43 amino acids long. In another embodiment, the propeptide sequence is a feline factor II leader sequence combined with the GLP-1(7-37) wild type sequence. The amino acid sequence of feline Factor II is known and can be found at: GenBank accession no. XP_003993267.1 which is reproduced in SEQ ID NO: 24 for convenience. In one embodiment, the propeptide sequence is amino acids 1-43 of SEQ ID NO: 24. In one embodiment of, the GLP-1 construct encodes the amino acid sequence set forth in SEQ ID NO: 25. In yet another embodiment, the GLP-1 construct is a codon optimized sequence encoding SEQ ID NO: 25. In another embodiment, the GLP-1 construct sequence is a canine factor II leader sequence combined with the GLP-1(7-37) wild type sequence. The amino acid sequence of canine Factor II is known and can be found at: NCBI Reference Sequence: XP_003639742.1, which is reproduced in SEQ ID NO: 26 for convenience. In one embodiment, the propeptide sequence is amino acids 1-41 of SEQ ID NO: 26. In another embodiment, the GLP-1 construct sequence encodes the amino acid sequence set forth in SEQ ID NO: 27. In yet another embodiment, the GLP-1 construct is a codon optimized sequence encoding SEQ ID NO: 27. In another embodiment, the GLP-1 construct sequence is a human factor II leader sequence combined with the GLP-1(7-37) wild type sequence. The amino acid sequence of human Factor II is known and can be found, e.g. at: NCBI Reference Sequence: NP_000497.1, which is reproduced in SEQ ID NO: 28 for convenience. In one embodiment, the propeptide sequence is amino acids 1-43 of SEQ ID NO: 28. In another embodiment, the GLP-1 construct sequence encodes the amino acid sequence set forth in SEQ ID NO: 29. In yet another embodiment, the GLP-1 construct is a codon optimized sequence encoding SEQ ID NO: 29. Similar constructs can be made using other isoforms of Factor II known in the art.

In another embodiment, the propeptide sequence is a factor IX leader sequence. In another embodiment, the propeptide sequence includes a factor IX sequence in combination with a furin site. In one embodiment, the propeptide is about 39-46 amino acids long. In another embodiment, the propeptide sequence is a feline factor IX leader sequence combined with the GLP-1(7-37) wild type sequence. The amino acid sequence of feline Factor IX is known and can be found at: GenBank accession no. NP_001009377.1 which is reproduced in SEQ ID NO: 30 for convenience. In one embodiment, the propeptide sequence is amino acids 1-46 of SEQ ID NO: 30. In one embodiment of, the GLP-1 construct encodes the amino acid sequence set forth in SEQ ID NO: 31. In yet another embodiment, the GLP-1 construct is a codon optimized sequence encoding SEQ ID NO: 31. In another embodiment, the GLP-1 construct sequence is a canine factor IX leader sequence combined with the GLP-1(7-37) wild type sequence. The amino acid sequence of canine Factor IX is known and can be found at: NCBI Reference Sequence: NP_001003323.1, which is reproduced in SEQ ID NO: 32 for convenience. In one embodiment, the propeptide sequence is amino acids 1-39 of SEQ ID NO: 32. In another embodiment, the GLP-1 construct sequence encodes the amino acid sequence set forth in SEQ ID NO: 33. In yet another embodiment, the GLP-1 construct is a codon optimized sequence encoding SEQ ID NO: 33. In another embodiment, the GLP-1 construct sequence is a human factor IX leader sequence combined with the GLP-1(7-37) wild type sequence. The amino acid sequence of human Factor IX is known and can be found, e.g. at: NCBI Reference Sequence: NP_000124.1, which is reproduced in SEQ ID NO: 34 for convenience. In one embodiment, the propeptide sequence is amino acids 1-46 of SEQ ID NO: 34. In another embodiment, the GLP-1 construct sequence encodes the amino acid sequence set forth in SEQ ID NO: 35. In yet another embodiment, the GLP-1 construct is a codon optimized sequence encoding SEQ ID NO: 35. Similar constructs can be made using other isoforms of Factor IX known in the art.

In another embodiment, the propeptide sequence is a protein S (also called vitamin K-dependent protein S) leader sequence. In another embodiment, the propeptide sequence includes a protein S sequence in combination with a furin site. In one embodiment, the propeptide is about 36-57 amino acids long. In another embodiment, the propeptide sequence is a feline protein S leader sequence combined with the GLP-1(7-37) wild type sequence. In one embodiment, the propeptide sequence is amino acids 1-57 of SEQ ID NO: 7. In one embodiment, the GLP-1 construct encodes the amino acid sequence set forth in SEQ ID NO: 7. In yet another embodiment, the GLP-1 construct is a codon optimized sequence encoding SEQ ID NO: 7. In another embodiment, the GLP-1 construct is encoded by SEQ ID NO: 8, or a codon optimized sequence thereof. The amino acid sequence of feline protein S is known and can be found at: GenBank accession no. XP_011284289 which is reproduced in SEQ ID NO: 36 for convenience. In one embodiment, the propeptide sequence is amino acids 1-36 of SEQ ID NO: 36. In one embodiment of, the GLP-1 construct encodes the amino acid sequence set forth in SEQ ID NO: 37. In yet another embodiment, the GLP-1 construct is a codon optimized sequence encoding SEQ ID NO: 37. In another embodiment, the GLP-1 construct sequence is a canine protein S leader sequence combined with the GLP-1(7-37) wild type sequence. The amino acid sequence of canine protein S is known and can be found at: NCBI Reference Sequence: XP_005639500.1, which is reproduced in SEQ ID NO: 38 for convenience. In one embodiment, the propeptide sequence is amino acids 1-41 of SEQ ID NO: 38. In another embodiment, the GLP-1 construct sequence encodes the amino acid sequence set forth in SEQ ID NO: 39. In yet another embodiment, the GLP-1 construct is a codon optimized sequence encoding SEQ ID NO: 39. In another embodiment, the GLP-1 construct sequence is a human protein S leader sequence combined with the GLP-1(7-37) wild type sequence. The amino acid sequence of human protein S is known and can be found, e.g. at: UniProtKB/Swiss-Prot: P07225.1, which is reproduced in SEQ ID NO: 40 for convenience. In one embodiment, the propeptide sequence is amino acids 1-41 of SEQ ID NO: 40. In another embodiment, the GLP-1 construct sequence encodes the amino acid sequence set forth in SEQ ID NO: 41. In yet another embodiment, the GLP-1 construct is a codon optimized sequence encoding SEQ ID NO: 41. Similar constructs can be made using other isoforms of Protein S known in the art.

In another embodiment, the propeptide sequence is a protein Z (also called vitamin K-dependent protein Z) leader sequence. In another embodiment, the propeptide sequence includes a protein Z sequence in combination with a furin site. In one embodiment, the propeptide is about 62 amino acids long. In another embodiment, the propeptide sequence is a feline protein Z leader sequence combined with the GLP-1(7-37) wild type sequence. In another embodiment, the GLP-1 construct sequence is a canine protein Z leader sequence combined with the GLP-1 (7-37) sequence shown in SEQ ID NO: 1. In another embodiment, the GLP-1 construct sequence is a human protein Z leader sequence combined with the GLP-1(7-37) wild type sequence. The amino acid sequence of human protein Z is known and can be found, e.g. at: GenBank: AAA36501.1, which is reproduced in SEQ ID NO: 42 for convenience. In one embodiment, the propeptide sequence is amino acids 1-62 of SEQ ID NO: 42. In another embodiment, the GLP-1 construct sequence encodes the amino acid sequence set forth in SEQ ID NO: 43. In yet another embodiment, the GLP-1 construct is a codon optimized sequence encoding SEQ ID NO: 43. Similar constructs can be made using other isoforms of Protein Z known in the art.

In another embodiment, the propeptide sequence is a protein C (also called vitamin K-dependent protein C) leader sequence. In another embodiment, the propeptide sequence includes a protein C sequence in combination with a furin site. In one embodiment, the propeptide is about 42 amino acids long. In another embodiment, the propeptide sequence is a feline protein C leader sequence combined with the GLP-1(7-37) sequence shown in SEQ ID NO: 1. The amino acid sequence of feline protein C is known and can be found at: NCBI Reference Sequence: XP_011283508.1 which is reproduced in SEQ ID NO: 44 for convenience. In one embodiment, the propeptide sequence is amino acids 1-42 of SEQ ID NO: 44. In one embodiment of, the GLP-1 construct encodes the amino acid sequence set forth in SEQ ID NO: 45. In yet another embodiment, the GLP-1 construct is a codon optimized sequence encoding SEQ ID NO: 45. In another embodiment, the GLP-1 construct sequence is a canine protein C leader sequence combined with the GLP-1(7-37) wild type sequence. The amino acid sequence of canine protein C is known and can be found at: NCBI Reference Sequence: GenBank: CAA05126.1, which is reproduced in SEQ ID NO: 46 for convenience. In one embodiment, the propeptide sequence is amino acids 1-42 of SEQ ID NO: 46. In another embodiment, the GLP-1 construct sequence encodes the amino acid sequence set forth in SEQ ID NO: 47. In yet another embodiment, the GLP-1 construct is a codon optimized sequence encoding SEQ ID NO: 47. In another embodiment, the GLP-1 construct sequence is a human protein C leader sequence combined with the GLP-1(7-37) sequence shown in SEQ ID NO: 1. The amino acid sequence of human protein C is known and can be found, e.g. at: GenBank: AAA60166.1, which is reproduced in SEQ ID NO: 48 for convenience. In one embodiment, the propeptide sequence is amino acids 1-42 of SEQ ID NO: 48. In another embodiment, the GLP-1 construct sequence encodes the amino acid sequence set forth in SEQ ID NO: 49. In yet another embodiment, the GLP-1 construct is a codon optimized sequence encoding SEQ ID NO: 49. Similar constructs can be made using other isoforms of Protein C known in the art.

In another embodiment, the propeptide sequence is an albumin leader sequence. In another embodiment, the propeptide sequence includes an albumin leader sequence in combination with a furin site. In one embodiment, the propeptide is about 24 amino acids long. In another embodiment, the propeptide sequence is a feline albumin leader sequence combined with the GLP-1 (7-37) wild type sequence. The amino acid sequence of feline albumin is known and can be found at: GenBank accession no. CAA59279.1 which is reproduced in SEQ ID NO: 50 for convenience. In one embodiment, the propeptide sequence is amino acids 1-24 of SEQ ID NO: 50. In one embodiment, the GLP-1 construct encodes the amino acid sequence set forth in SEQ ID NO: 9. In yet another embodiment, the GLP-1 construct is a codon optimized sequence encoding SEQ ID NO: 9. In one embodiment, the nucleic acid sequence encoding the feline albumin propeptide-GLP-1 construct is SEQ ID NO: 10. In another embodiment, the GLP-1 construct sequence is a canine albumin leader sequence combined with the GLP-1(7-37) wild type sequence. The amino acid sequence of canine albumin is known and can be found at: NCBI Reference Sequence: CAB64867.1, which is reproduced in SEQ ID NO: 51 for convenience. In one embodiment, the propeptide sequence is amino acids 1-24 of SEQ ID NO: 51. In another embodiment, the GLP-1 construct sequence encodes the amino acid sequence set forth in SEQ ID NO: 52. In yet another embodiment, the GLP-1 construct is a codon optimized sequence encoding SEQ ID NO: 52. In another embodiment, the GLP-1 construct sequence is a human albumin leader sequence combined with the GLP-1(7-37) wild type sequence. The amino acid sequence of human albumin is known and can be found, e.g. at: NCBI Reference Sequence: AAA98797.1, which is reproduced in SEQ ID NO: 53 for convenience. In one embodiment, the propeptide sequence is amino acids 1-24 of SEQ ID NO: 53. In another embodiment, the GLP-1 construct sequence encodes the amino acid sequence set forth in SEQ ID NO: 54. In yet another embodiment, the GLP-1 construct is a codon optimized sequence encoding SEQ ID NO: 54. Similar constructs can be made using other isoforms of albumin known in the art.

In one embodiment, the nucleic acid sequences encoding the GLP-1 constructs described herein are engineered into any suitable genetic element, e.g., naked DNA, phage, transposon, cosmid, RNA molecule (e.g., mRNA), episome, etc., which transfers the hLDLR sequences carried thereon to a host cell, e.g., for generating nanoparticles carrying DNA or RNA, viral vectors in a packaging host cell and/or for delivery to a host cell in a subject. In one embodiment, the genetic element is a plasmid. The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, NY (2012).

As used herein, an "expression cassette" refers to a nucleic acid molecule which comprises the GLP-1 construct coding sequences (e.g., coding sequences for the propeptide and GLP-1 active peptide), promoter, and may include other regulatory sequences therefor, which cassette may be engineered into a genetic element and/or packaged into the capsid of a viral vector (e.g., a viral particle). Typically, such an expression cassette for generating a viral vector contains the GLP-1 construct sequences described herein flanked by packaging signals of the viral genome and other expression control sequences such as those described herein. Any of the expression control sequences can be optimized for a specific species using techniques known in the art including, e.g, codon optimization, as described herein.

The expression cassette typically contains a promoter sequence as part of the expression control sequences. In one embodiment, the liver-specific promoter thyroxin binding globulin (TBG) is used. In the plasmids and vectors described herein, a CB7 promoter is used. CB7 is a chicken β-actin promoter with cytomegalovirus enhancer elements. Alternatively, other liver-specific promoters may be used [see, e.g., The Liver Specific Gene Promoter Database, Cold Spring Harbor, http://rulai.schl.edu/LSPD, alpha 1 antitrypsin (A1AT); human albumin Miyatake et al., J. Virol., 71:5124 32 (1997), humAlb; and hepatitis B virus core promoter, Sandig et al., Gene Ther., 3:1002 9 (1996)]. TTR minimal enhancer/promoter, alpha-antitrypsin promoter, LSP (845 nt)25 (requires intron-less scAAV). Although less desired, other promoters, such as viral promoters, constitutive promoters, regulatable promoters [see, e.g., WO 2011/126808 and WO 2013/04943], or a promoter responsive to physiologic cues may be used may be utilized in the vectors described herein.

In addition to a promoter, an expression cassette and/or a vector may contain other appropriate transcription initiation, termination, enhancer sequences, efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. Examples of suitable polyA sequences include, e.g., SV40, bovine growth hormone (bGH), and TK polyA. Examples of suitable enhancers include, e.g., the alpha fetoprotein enhancer, the TTR minimal promoter/enhancer, LSP (TH-binding globulin promoter/alpha1-microglobulin/bikunin enhancer), amongst others.

These control sequences are "operably linked" to the GLP-1 construct sequences. As used herein, the term "operably linked" refers to both expression control sequences that are contiguous with the gene of interest and expression control sequences that act in trans or at a distance to control the gene of interest.

The expression cassette may be engineered onto a plasmid which is used for production of a viral vector. The minimal sequences required to package the expression cassette into an AAV viral particle are the AAV 5' and 3' ITRs, which may be of the same AAV origin as the capsid, or of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped.

Typically, an expression cassette for an AAV vector comprises an AAV 5' ITR, the propeptide-GLP-1 active peptide coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

Exemplary plasmids are provided in the sequence listing. SEQ ID NO: 57 provides the sequence of a plasmid encoding a feline protein S propeptide-GLP1 construct, entitled pn1044.CB7.GLP1feprotS. In one embodiment, the expression cassette is engineered into the plasmid of SEQ ID NO: 57. SEQ ID NO: 58 provides the sequence of a plasmid encoding a feline IL2 propeptide (including furin site)-GLP1 construct, entitled pn1044.CB7.GLP1feIL2fur. In one embodiment, the expression cassette is engineered into the plasmid of SEQ ID NO: 58. SEQ ID NO: 59 provides the sequence of a plasmid encoding a feline thrombin propeptide-GLP1 construct, entitled p1044.CB7.GLP1feThrombin. In one embodiment, the expression cassette is engineered into the plasmid of SEQ ID NO: 59. SEQ ID NO: 60 provides the sequence of a plasmid encoding a feline mannosidase (with furin site) propeptide-GLP1 construct, entitled p1044.CB7.GLP1feManFur. In one embodiment, the expression cassette is engineered into the plasmid of SEQ ID NO: 60. SEQ ID NO: 61 provides the sequence of a plasmid encoding a feline albumin propeptide-GLP1 construct, entitled p1044 GLP1fealb. In one embodiment, the expression cassette is engineered into the plasmid of SEQ ID NO: 61. SEQ ID NO: 62 provides the sequence of a plasmid encoding a feline albumin (with furin site) propeptide-GLP1 construct, entitled p1044 GLP1fealbfur. In one embodiment, the expression cassette is engineered into the plasmid of SEQ ID NO: 62. SEQ ID NO: 63 provides the sequence of a plasmid encoding a feline thrombin (with furin site) propeptide-GLP1 construct, entitled p1044 GLP1fealbfur. In one embodiment, the expression cassette is engineered into the plasmid of SEQ ID NO: 62.

The abbreviation "sc" refers to self-complementary. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

An adeno-associated virus (AAV) viral vector is an AAV DNase-resistant particle having an AAV protein capsid into which is packaged nucleic acid sequences for delivery to target cells. An AAV capsid is composed of 60 capsid (cap) protein subunits, VP1, VP2, and VP3, that are arranged in an icosahedral symmetry in a ratio of approximately 1:1:10 to 1:1:20, depending upon the selected AAV. AAV serotypes may be selected as sources for capsids of AAV viral vectors (DNase resistant viral particles) including, e.g., AAV1, AAV2, AAV3, AAV4, AAV5, AAV6, AAV6.2, AAV7, AAV8, AAV9, rh10, AAVrh64R1, AAVrh64R2, rh8, rh.10, variants of any of the known or mentioned AAVs or AAVs yet to be discovered. See, e.g., US Published Patent Application No. 2007-0036760-A1; US Published Patent Application No. 2009-0197338-A1; EP 1310571. See also, WO 2003/042397 (AAV7 and other simian AAV), U.S. Pat. Nos. 7,790,449 and 7,282,199 (AAV8), WO 2005/033321 and U.S. Pat. No. 7,906,111 (AAV9), and WO 2006/110689, and WO 2003/042397 (rh.10). Alternatively, a recombinant AAV based upon any of the recited AAVs, may be used as a source for the AAV capsid. These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV Caps or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

For packaging an expression cassette into virions, the ITRs are the only AAV components required in cis in the same construct as the gene. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or obtained from academic, commercial, or public sources (e.g., the American Type Culture Collection, Manassas, VA). Alternatively, the AAV sequences may be obtained through synthetic or other suitable means by reference to published sequences such as are available in the literature or in databases such as, e.g., GenBank®, PubMed®, or the like.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, NY (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

Optionally, the GLP-1 constructs described herein may be delivered via viral vectors other than rAAV. Such other viral vectors may include any virus suitable for gene therapy may be used, including but not limited to adenovirus; herpes virus; lentivirus; retrovirus; etc. Suitably, where one of these other vectors is generated, it is produced as a replication-defective viral vector.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

Also provided are compositions which include the viral vector constructs described herein. The pharmaceutical compositions described herein are designed for delivery to subjects in need thereof by any suitable route or a combination of different routes. Direct delivery to the liver (optionally via intravenous, via the hepatic artery, or by transplant), oral, inhalation, intranasal, intratracheal, intraarterial, intraocular, intravenous, intramuscular, subcutaneous, intradermal, and other parental routes of administration. The viral vectors described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

The replication-defective viruses can be formulated with a physiologically acceptable carrier for use in gene transfer and gene therapy applications. In the case of AAV viral vectors, quantification of the genome copies ("GC") may be used as the measure of the dose contained in the formulation. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal).

Also, the replication-defective virus compositions can be formulated in dosage units to contain an amount of replication-defective virus that is in the range of about $1.0 \times 10^9$ GC to about $1.0 \times 10^{15}$ GC. In another embodiment, this amount of viral genome may be delivered in split doses. In one embodiment, the dosage is about $1.0 \times 10^{11}$ GC to about $1.0 \times 10^{12}$ GC for an average feline or small canine subject of about 5 kg. In one embodiment, the dosage is about $1.0 \times 10^{12}$ GC to about $1.0 \times 10^{13}$ GC for an average medium canine subject of about 20 kg. The average canine ranges from about 5 to about 50 kg in body weight. In one embodiment, the dosage is about $1.0 \times 10^{12}$ GC to about $1.0 \times 10^{13}$ GC for an average human subject of about 70 kg. The average human subject ranges from about 55 to about 80 kg in body weight. In one embodiment, the dosage is about $1.0 \times 10^{11}$ GC to $1.0 \times 10^{13}$ GC for a subject. In another embodiment, the dose about $3 \times 10^{12}$ GC. For example, the dose of AAV virus may be about $1 \times 10^{11}$ GC, about $5 \times 10^{11}$ GC, about $1 \times 10^{12}$ GC, about $5 \times 10^{12}$ GC, or about $1 \times 10^{13}$ GC. In another example, the constructs may be delivered in an amount of about 0.001 mg to about 10 mg per mL. In one embodiment, the constructs may be delivered in volumes from 14 to about 100 mL for a veterinary subject. See, e.g., Diehl et al, J. Applied Toxicology, 21:15-23 (2001) for a discussion of good practices for administration of substances to various veterinary animals. This document is incorporated herein by reference. As used herein, the term "dosage" can refer to the total dosage delivered to the subject in the course of treatment, or the amount delivered in a single (of multiple) administration.

The above-described recombinant vectors may be delivered to host cells according to published methods. The rAAV, preferably suspended in a physiologically compatible carrier, may be administered to a desired subject including without limitation, a cat, dog, human or non-human mammalian subject. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and/or variants and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

In one embodiment, a composition provided which includes one or more viral vectors which each comprise one or more GLP-1 constructs as described herein. For example, in one embodiment, a composition includes an AAV vector which encodes a propeptide—GLP-1-(7-37) construct. The same composition also includes an AAV vector which encodes a propeptide and GLP-1-(7-36)NH$_2$ construct. The source of the AAV vector capsids can be the same or different for each construct contained in the composition.

The viral vectors and other constructs described herein may be used in preparing a medicament for delivering a GLP-1 construct to a subject in need thereof, supplying GLP-1 having an increased half-life to a subject, and/or for treating type II diabetes or metabolic syndrome in a subject. Thus, in another aspect a method of treating diabetes is provided. The method includes administering a composition as described herein to a subject in need thereof. In one embodiment, the composition includes a viral vector containing a propeptide-GLP-1 expression cassette, as described herein. In one embodiment, the subject is a mammal. In another embodiment, the subject is a feline or canine. In another embodiment, the subject is a human.

In another embodiment, a method for treating T2DM in a feline is provided. The method includes administering a viral vector comprising a nucleic acid molecule comprising a sequence encoding a feline factor IX propeptide and the active portion of GLP-1, wherein, when expressed, the N-terminal amino acid of GLP-1 immediately follows the C-terminal amino acid of the propeptide.

In another aspect a method of treating metabolic syndrome is provided. The method includes administering a composition as described herein to a subject in need thereof. In one embodiment, the composition includes a viral vector containing a propeptide-GLP-1 expression cassette, as described herein. In one embodiment, the subject is a mammal. In another embodiment, the subject is a feline or canine. In another embodiment, the subject is a human.

In another aspect a method of reducing body weight in a subject is provided. The method includes administering a composition as described herein to a subject in need thereof. In one embodiment, the composition includes a viral vector containing a propeptide-GLP-1 expression cassette, as described herein. In one embodiment, the subject is a mammal. In another embodiment, the subject is a feline or canine. In another embodiment, the subject is a human.

A course of treatment may optionally involve repeat administration of the same viral vector (e.g., an AAV8 vector) or a different viral vector (e.g., an AAV8 and an AAVrh10). Still other combinations may be selected using the viral vectors described herein. Optionally, the composition described herein may be combined in a regimen involving other diabetic drugs or protein-based therapies (including e.g., GLP-1 analogues, insulin, oral antihyperglycemic drugs (sulfonylureas, biguanides, thiazolidinediones, and alpha-glucosidase inhibitors). Optionally, the composition described herein may be combined in a regimen involving lifestyle changes including dietary and exercise regimens.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

The term "regulation" or variations thereof as used herein refers to the ability of a composition to inhibit one or more components of a biological pathway.

A "subject" is a mammal, e.g., a human, mouse, rat, guinea pig, dog, cat, horse, cow, pig, or non-human primate, such as a monkey, chimpanzee, baboon or gorilla. As used herein, the term "subject" is used interchangeably with "patient".

As used herein, "disease", "disorder" and "condition" are used interchangeably, to indicate an abnormal state in a subject.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

Example 1—Construction of GLP-1 Vectors

Several secreted proteins containing propeptides with known cleavage sites were selected. These include coagulation factors (factor II, VII, IX, X, protein C, protein S) and other proteins produced by the liver (albumin). The propeptide sequence was placed upstream of the GLP-1 (7-37) amino acid sequence. A control sequence containing only an interleukin-2 signal peptide followed by GLP-1 (7-37) was also designed. The resulting protein sequence was back-translated and codon optimized, followed by addition of a kozak consensus sequence, stop codon, and cloning sites. The sequences were produced by GeneArt, and cloned into an expression vector containing a chicken-beta actin promoter with CMV enhancer (p1044). The expression construct is flanked by AAV2 ITRs. The feline FIX_GLP1 amino acid sequence is shown in SEQ ID NO: 5. The feline ProtS_GLP1 amino acid sequence is shown in SEQ ID NO: 7. The feline Alb_GLP1 amino acid sequence is shown in SEQ ID NO: 9. The feline FVII_GLP1 amino acid sequence is shown in SEQ ID NO: 17. The feline FII_GLP1 amino acid sequence is shown in SEQ ID NO: 25. The feline ProtC_GLP1 amino acid sequence is shown in SEQ ID NO: 45.

Example 2—In Vitro Assays

The purified plasmids for the constructs containing only the IL-2 signal peptide or the feline factor IX propeptide upstream of the GLP-1 sequence were transfected into triplicate wells of a 6 well plate of 90% confluent HEK 293 cells using lipofectamine 2000 according to the manufacturer's instructions. Supernatant was harvested 48 hours after transfection and active GLP-1 was measured using the high-sensitivity N-terminal GLP-1 ELISA (Millipore). The expression of the two constructs is shown in FIG. 1. FIG. 1 shows that expression of GLP-1 in the IL-2 control was essentially zero, while that of the factor IX construct was about 60 pM.

Example 3—In Vivo GLP-1 Expression

Figure 2:
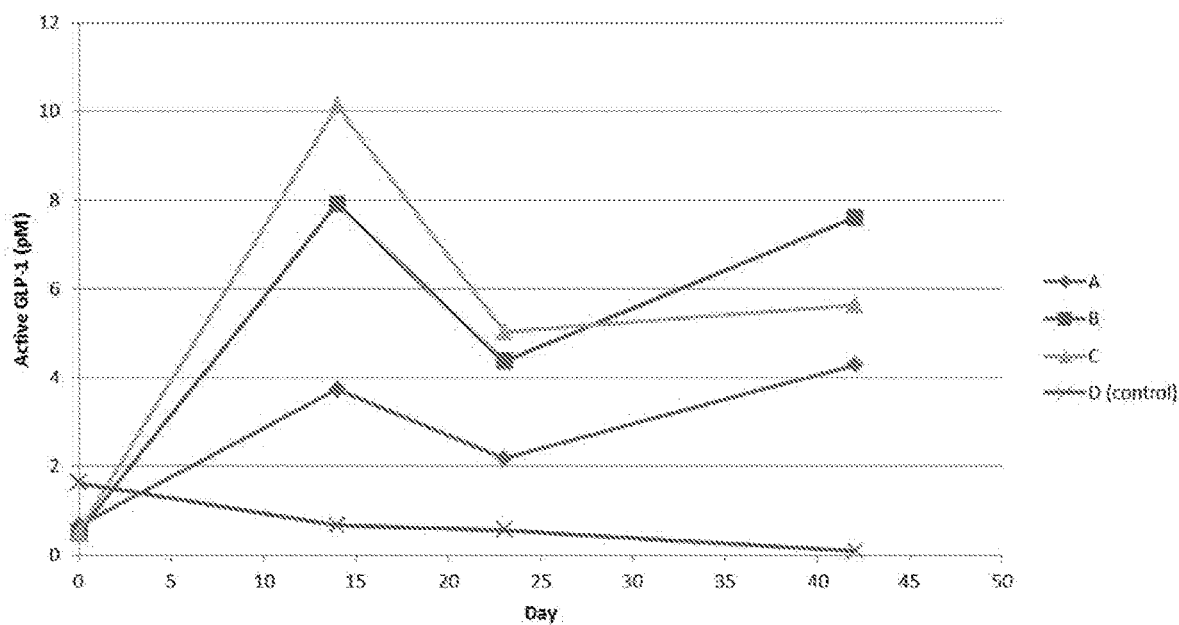
FIG. 2 provides results from a study showing in vivo expression of GLP-1 via transduction of RAG−/− mice with AAV8.CB.fFIX_GLP1. Top three lines (square, triangle and diamond) correspond to three mice treated with AAV8.CB.fFIX_GLP1. Bottom line corresponds to an internal control mouse.

The construct containing the feline factor IX propeptide was packaged in an AAV serotype 8 vector by triple transfection and iodixanol gradient purification, as previously described. RAG−/− mice (n=4) mice were treated with an intravenous injection of the vector ($10^{12}$ GC/kg) in 50 microliters of PBS. Intravenous access could not be achieved in one animal (mouse D) which served as an internal control. Serum was serially collected by separating whole blood in serum separator tubes containing 5 microliters DPP-IV inhibitor (Millipore) and assayed for active GLP-1 as above. Serum active GLP-1 concentrations are shown in FIG. 2. FIG. 2 shows that the level of active GLP-1 in the control mouse is below to 2 pM. In contrast, in the three mice injected with AAV8.CB.fFIX_GLP1, the GLP-1 concentration started at under 1 pM, spiked at day 14 (to about 10 pM in mouse C), decreased at day 21 and then rebounded at day 42. Although the GLP-1 is delivered in an artificial construct, following cleavage of the propeptide, the peptide is active as shown in FIG. 2. In addition to liver (FIG. 2), processing of propeptide has been characterized in muscle (data not shown). Processing is efficient even when overexpressed.

Example 4—In Vivo Treatment of Diabetes with GLP-1 Construct

Figure 3:
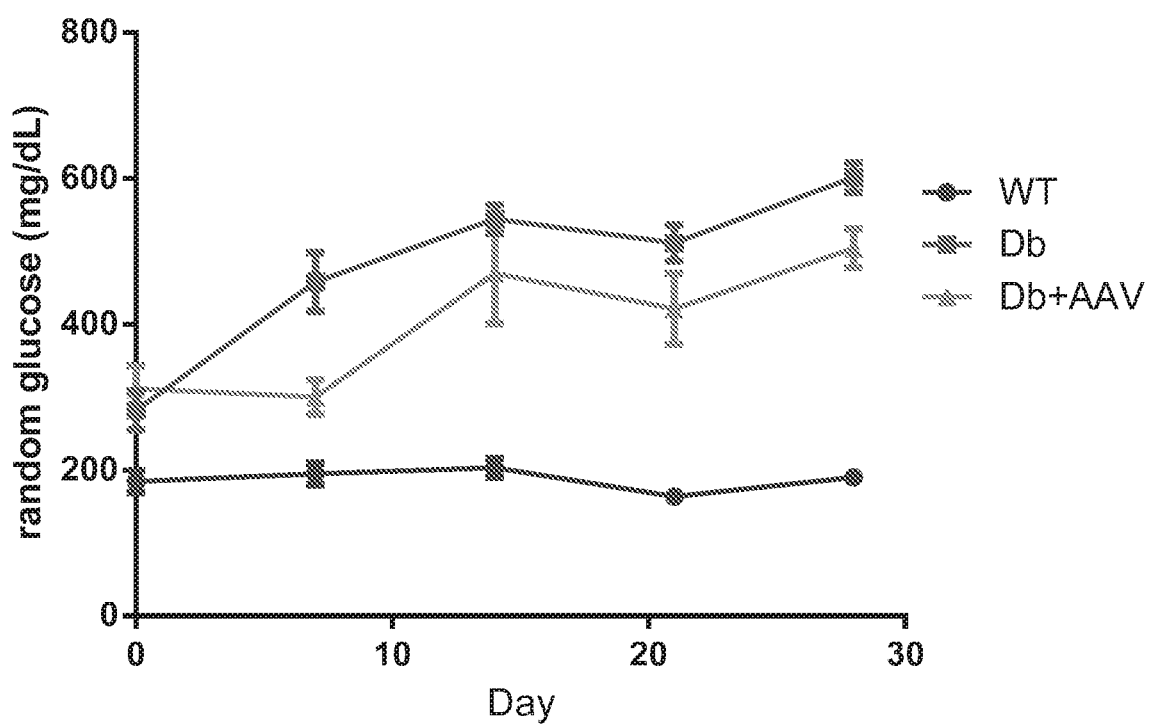
FIG. 3 provides results from a study in which diabetic mice (db/db) were treated with AAV8.CB.fFIX_GLP1 (Db+ AAV). Wild type (WT), age matched controls were used as were diabetic (Db) mice not transfected with the vector. Serum glucose levels were measured each week. Values are mean+/−SEM.
Figure 4:
FIG. 4 is a map showing the construct strategy for the GLP-1 construct used in Examples 2 and 3. The map shows the CB7 promoter, feline factor IX propeptide, GLP-1(7-37) and a poly A sequence.
Figure 5:
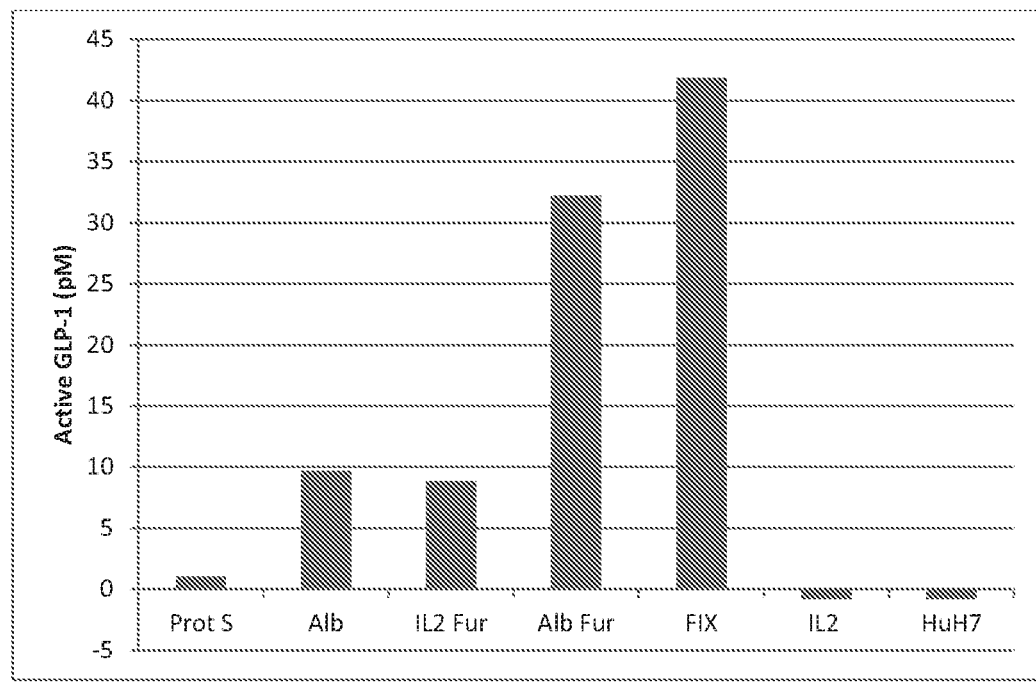
FIG. 5 provides the results of in vitro evaluation of active GLP-1 expression in transfected HuH7 cells. Each of the following sequences was placed upstream of the GLP-1 sequence as described in Example 1: Protein S propeptide (Prot S), Albumin propeptide (Alb), IL2 leader with furin site (IL2 Fur), albumin propeptide with furin site (Alb Fur), factor IX propeptide (FIX), IL2 leader without furin site (IL2), and untransfected HuH7 cells. All sequences used were feline sequences.
Figure 6:
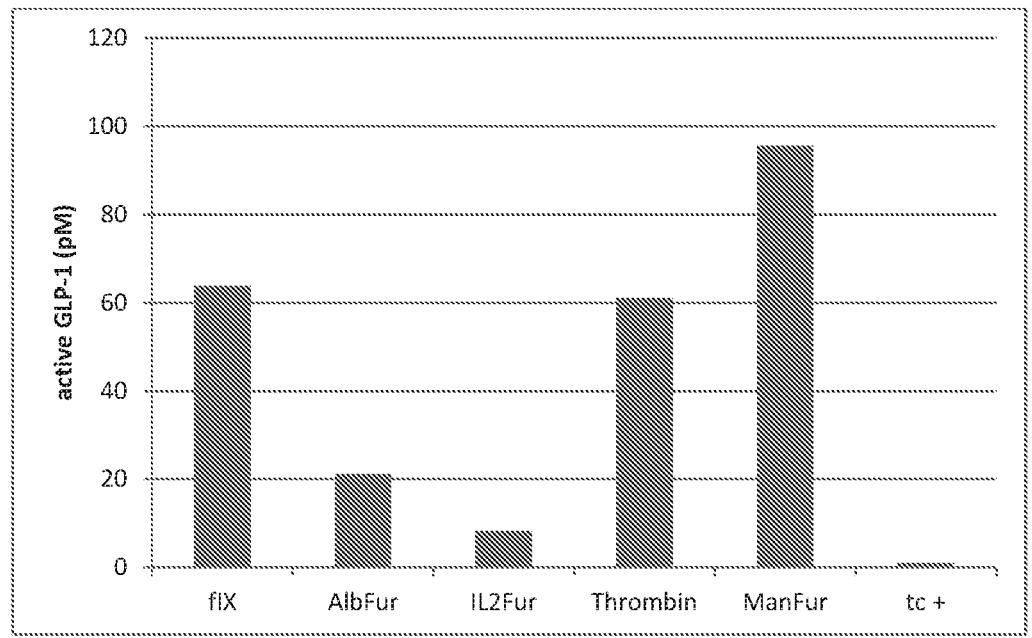
FIG. 6 provides the results of in vitro evaluation of active GLP-1 expression in transfected cells. Each of the following sequences was placed upstream of the GLP-1 sequence as described in Example 1: IL2 leader with furin site (IL2 Fur), albumin propeptide with furin site (Alb Fur), factor IX propeptide (FIX), thrombin leader sequence, mannosidase leader with furin site (ManFur), and untransfected cells (tc+). All sequences used were feline sequences.

Diabetic (db/db) mice at 6-7 weeks of age were treated with an intravenous injection of the factor IX propeptide vector ($3\times10^{12}$ GC/kg, n=5) in 50 microliters PBS. Untreated age-matched db/db mice (n=5) and untreated db+/−mice (n=5) (WT) served as controls. Serum glucose was measured weekly using a plate based glucose assay (Caymen Chemical). The serum glucose data are shown in FIG. 3. FIG. 3 shows that the serum glucose level of diabetic mice treated with AAV8.CB.fFIX_GLP1 was consistently less than untreated, age-matched diabetic (Db) mice after treatment.

Example 5—In Vivo GLP-1 Expression of Various Constructs

Figure 7:
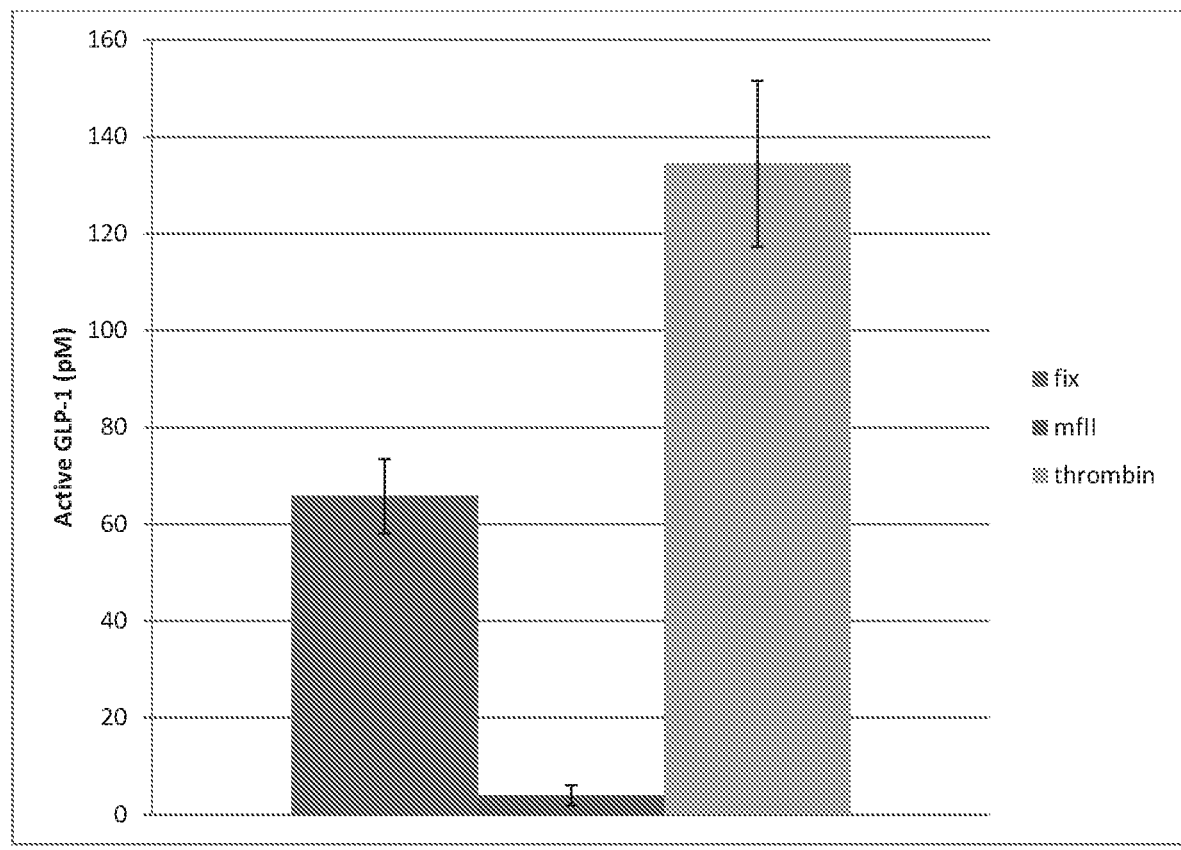
FIG. 7 provides the results of administration of three different GLP-1 constructs in wildtype mice as described in Example 5. Cohorts of 4 mice each were injected with $5 \times 10^{10}$ of the corresponding vector and were evaluated for active GLP-1 expression.

This study was designed to analyze possible clinical candidates for AAV mediated GLP-1 expression. We had seen previously the Factor IX furin propeptide was able to express n-terminus cleaved glp1 (active glp-1) in mice. We then tried various other constructs in black six wildtype mice to evaluate a possibly better construct. Cohorts were of 4 four mice each, with $5\times10^{10}$ total of corresponding vector administered IV. Thrombin furin propeptide, another clotting factor, produced more active GLP-1 in black six than Factor IX and Mannosidase furin constructs. FIG. 7.

Example 6—In Vivo GLP-1 Treatment of Cats

A single dose, open label pilot study will be done on 6 client-owned animals. Inclusion criteria include:

1. Blood glucose ≥200 mg/dL on at least 2 consecutive measurements
2. Fructosamine above the laboratory reference range
3. Subject is not a candidate for insulin therapy (due to inability of the owner to provide treatment or other contraindication)
4. Owner willing to adhere to study protocol Exclusion criteria include:

1. Hyperglycemia believed to be secondary to medications, acromegaly, etc
2. Currently using insulin or oral hypoglycemic medications
3. Not amenable to restraint and venipuncture
4. Any condition that, in the opinion of the investigator, would present additional risk to the subject or interfere with evaluation of the study drug.

The subject animals will receive $10^{13}$ GC AAV8.CB7.thrGLP1 on day 0. CBC/chem, fructosamine, glucose curve, and serum GLP-1 will be done at screening and days 0, 14, 28, 42, 60, 90, 120, 150, 180.

Example 7—Capsid and Dosage Comparison in Healthy Cats

Healthy cats were given vector expressing GLP1 as described below, and evaluated via Millipore Active GLP1 assay on a weekly basis till d90. Blood for assay analysis was collected in GLP1 preservation DPPIV inhibitor plasma tubes (BD Biosciences, P700 plasma tubes). CBC and chemistry panels were taken at day 0, day 14, day 28, day 42, day 60 and at day 90. Post day 90, animals were sacrificed.

Figure 8:
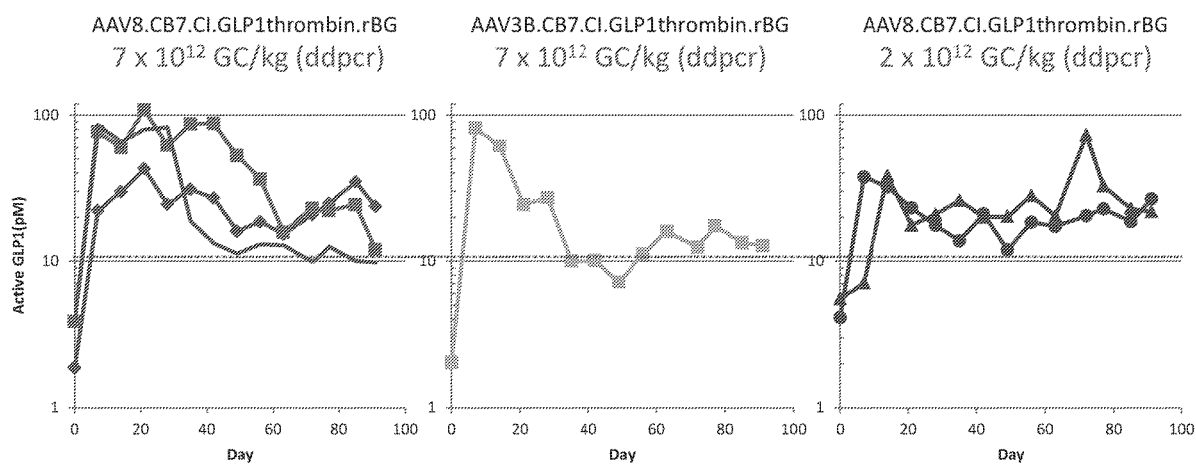
FIG. 8 provides the results of administration of three different GLP-1 constructs in healthy cats as described in Example 7. Blood was evaluated for active GLP-1 expression at the time points indicated.

The first cohort of cats was given AAV8.CB7.CI.GLP1thrombin.rBG at $7\times10^{12}$ gc/kg as determined by digital droplet PCR (ddpcr). One cat was given AAV3b.CB7.CI.GLP1thrombin.rBG at $7\times10^{12}$ gc/kg (ddpcr). Two cats were given AAV8.CB7.CI.GLP1thrombin.rBG $2\times10^{12}$ gc/kg (ddpcr). The difference in glp1 activity is shown FIG. 8.

All publications cited in this specification, as well as U.S. Provisional applications 62/201,803 and 62/356,289, are incorporated herein by reference. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

What is claimed is:

1. A recombinant adeno-associated virus (AAV) vector useful for treating diabetes in a feline comprising a nucleic acid molecule comprising a sequence encoding a propeptide and a GLP-1 peptide, wherein the propeptide is a feline clotting factor II propeptide, wherein the feline clotting factor II propeptide is amino acids 1-43 of SEQ ID NO: 24, and the GLP-1 peptide is SEQ ID NO: 1 and wherein the nucleic acid sequence encoding the GLP-1 peptide is SEQ ID NO: 2.

2. The AAV vector of claim 1, wherein the AAV vector further comprises expression control sequences that direct expression of the propeptide and GLP-1 peptide in a host cell.

3. The AAV vector of claim 2, wherein the expression control sequences comprise a promoter selected from CB7 promoter, thyroxin-binding globulin (TBG) promoter and a lymphocyte-specific protein 1 (LSP1) promoter.

4. The AAV vector of claim 1, further comprising one or more of an intron, a Kozak sequence, a polyA, and a post-transcriptional regulatory element.

5. The AAV vector of claim 1, wherein the AAV has an AAV8, rh64R1, AAV9, AAVhu.37, or rh10 capsid, or a variant thereof.

6. A pharmaceutical composition comprising a pharmaceutically acceptable carrier and the AAV vector according to claim 1.

7. A method for treating diabetes, said method comprising administering the composition of claim 6 to a feline in need thereof.

8. The method according to claim 7, wherein said composition is administered with insulin therapy.

9. The method according to claim 7, wherein a dose of about $1\times10^{12}$ GC/kg of the recombinant AAV vector is administered.

10. The method according to claim 7, wherein said composition is administered more than once.

11. A recombinant AAV vector useful for treating diabetes in a canine comprising a nucleic acid molecule comprising a sequence encoding a propeptide and a GLP-1 peptide, wherein the propeptide is a canine clotting factor II propeptide, wherein the canine clotting factor II propeptide is amino acids 1-41 of SEQ ID NO: 26, and the GLP-1 peptide is SEQ ID NO: 1 and wherein the nucleic acid sequence encoding the GLP-1 peptide is SEQ ID NO: 2.

12. The AAV vector of claim 11, wherein the AAV vector further comprises expression control sequences that direct expression of the propeptide and GLP-1 peptide in a host cell.

13. The AAV vector of claim 12, wherein the expression control sequences comprise a promoter selected from CB7 promoter, thyroxin-binding globulin (TBG) promoter and a lymphocyte-specific protein 1 (LSP1) promoter.

14. The AAV vector of claim 11, further comprising one or more of an intron, a Kozak sequence, a polyA, and a post-transcriptional regulatory element.

15. The AAV vector of claim 11, wherein the AAV has an AAV8, rh64R1, AAV9, AAVhu.37, or rh10 capsid, or a variant thereof.

16. A pharmaceutical composition comprising a pharmaceutically acceptable carrier and the AAV vector according to claim 11.

17. A method for treating diabetes in a canine, said method comprising administering the composition of claim 16 to a canine in need thereof.

18. The method according to claim 17, wherein said composition is administered with insulin therapy.

19. The method according to claim 17, wherein a dose of about $1\times10^{12}$ GC/kg of the recombinant AAV vector is administered.

20. The method according to claim 17, wherein said composition is administered more than once.

* * * * *

```
SEQUENCE LISTING

<160> NUMBER OF SEQ ID NOS: 62

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
```

<210> SEQ ID NO 2
<211> LENGTH: 96
<212> TYPE: DNA
<213> ORGANISM: Homo sapiens

<400> SEQUENCE: 2
cacgccgagg gcacctttac cagcgacgtg tccagctacc tggaaggcca ggccgccaaa    60
gagtttatcg cctggctcgt gaagggcaga ggctga    96

<210> SEQ ID NO 3
<211> LENGTH: 46
<212> TYPE: PRT
<213> ORGANISM: Felis catus

<400> SEQUENCE: 3

Met Arg Cys Leu Asn Met Ile Met Ala Glu Pro Pro Gly Leu Ile Thr
1               5                   10                  15

Ile Cys Leu Leu Gly Tyr Leu Leu Gly Ala Asp Cys Thr Val Phe Leu
            20                  25                  30

Asp His Glu Asp Ala Thr Lys Val Leu Ser Arg Pro Lys Arg
        35                  40                  45

<210> SEQ ID NO 4
<211> LENGTH: 138
<212> TYPE: DNA
<213> ORGANISM: Felis catus

<400> SEQUENCE: 4
atgcggtgcc tgaatatgat catggccgag ccccctggcc tgatcaccat ctgtctgctg    60
ggctacctgc tgggcgccga ctgcaccgtg tttctggatc acgaggacgc caccaaggtg   120
ctgagccggc ctaagaga   138

<210> SEQ ID NO 5
<211> LENGTH: 77
<212> TYPE: PRT
<213> ORGANISM: Artificial Sequence
<220> FEATURE:
<223> OTHER INFORMATION: feline factor IX leader_GLP-1 active

<400> SEQUENCE: 5

Met Arg Cys Leu Asn Met Ile Met Ala Glu Pro Pro Gly Leu Ile Thr
1               5                   10                  15

Ile Cys Leu Leu Gly Tyr Leu Leu Gly Ala Asp Cys Thr Val Phe Leu
            20                  25                  30

Asp His Glu Asp Ala Thr Lys Val Leu Ser Arg Pro Lys Arg His Ala
        35                  40                  45

Glu Gly Thr Phe Thr Ser Asp Val Ser Ser Tyr Leu Glu Gly Gln Ala
    50                  55                  60

Ala Lys Glu Phe Ile Ala Trp Leu Val Lys Gly Arg Gly
65                  70                  75

<210> SEQ ID NO 6
<211> LENGTH: 234
<212> TYPE: DNA
<213> ORGANISM: Artificial Sequence
<220> FEATURE:
<223> OTHER INFORMATION: feline factor IX leader_GLP-1 active

<400> SEQUENCE: 6

```
atgcggtgcc tgaatatgat catggccgag cccctggcc tgatcaccat ctgtctgctg      60
ggctacctgc tgggcgccga ctgcaccgtg tttctggatc acgaggacgc caccaaggtg    120
ctgagccggc taagagaca cgccgagggc acctttacca gcgacgtgtc cagctacctg     180
gaaggccagg ccgccaaaga gtttatcgcc tggctcgtga agggcagagg ctga          234
```

<210> SEQ ID NO 7
<211> LENGTH: 88
<212> TYPE: PRT
<213> ORGANISM: Artificial Sequence
<220> FEATURE:
<223> OTHER INFORMATION: feline protein S propeptide_GLP-1 active

<400> SEQUENCE: 7

```
Met Gly Val Asp Gly Arg Ile Phe Phe Leu Met Pro Ser Met Ala Phe
1               5                   10                  15

Gln Leu Leu Asn Glu Ser Arg Pro Ser Ser Leu Leu Ile Gln Met Phe
                20                  25                  30

Pro Gly Leu Ser Phe Ile Cys Thr Thr Val Leu Ser Lys Gln His Ala
            35                  40                  45

Ser Gln Val Leu Ile Arg Lys Arg Arg His Ala Glu Gly Thr Phe Thr
        50                  55                  60

Ser Asp Val Ser Ser Tyr Leu Glu Gly Gln Ala Ala Lys Glu Phe Ile
65                  70                  75                  80

Ala Trp Leu Val Lys Gly Arg Gly
                85
```

<210> SEQ ID NO 8
<211> LENGTH: 267
<212> TYPE: DNA
<213> ORGANISM: Artificial Sequence
<220> FEATURE:
<223> OTHER INFORMATION: feline protein S propeptide_GLP-1 active

<400> SEQUENCE: 8

```
atgggcgtgg acggccggat attcttcctg atgcccagca tggccttcca gctgctgaac     60
gagagcagac ccagcagcct gctgatccag atgttccccg gcctgagctt catctgcacc   120
accgtgctga gcaagcagca cgccagccag gtgctgatcc ggaagagaag gcacgccgag   180
ggcaccttca ccagcgacgt gtccagctac ctggaaggac aggccgccaa agagtttatc   240
gcctggctcg tgaagggcag aggctga                                        267
```

<210> SEQ ID NO 9
<211> LENGTH: 55
<212> TYPE: PRT
<213> ORGANISM: Artificial Sequence
<220> FEATURE:
<223> OTHER INFORMATION: feline albumin propeptide_GLP-1 active aa

<400> SEQUENCE: 9

```
Met Lys Trp Val Thr Phe Ile Ser Leu Leu Leu Leu Phe Ser Ser Ala
1               5                   10                  15

Tyr Ser Arg Gly Val Thr Arg Arg His Ala Glu Gly Thr Phe Thr Ser
                20                  25                  30

Asp Val Ser Ser Tyr Leu Glu Gly Gln Ala Ala Lys Glu Phe Ile Ala
            35                  40                  45

Trp Leu Val Lys Gly Arg Gly
        50                  55
```

<210> SEQ ID NO 10
<211> LENGTH: 168
<212> TYPE: DNA
<213> ORGANISM: Artificial Sequence
<220> FEATURE:
<223> OTHER INFORMATION: feline albumin propeptide_GLP-1 active DNA

<400> SEQUENCE: 10

```
atgaaatggg tcaccttcat cagcctgctg ctgctgttca gcagcgccta cagcagaggc      60
gtgaccagaa ggcacgccga gggcaccttt accagcgacg tgtccagcta cctggaaggc     120
caggccgcca aagagtttat cgcctggctc gtgaagggca ggggctga                  168
```

<210> SEQ ID NO 11
<211> LENGTH: 466
<212> TYPE: PRT
<213> ORGANISM: Felis catus

<400> SEQUENCE: 11

```
Met Arg Cys Leu Asn Met Ile Met Ala Glu Pro Pro Gly Leu Ile Thr
1               5                   10                  15

Ile Cys Leu Leu Gly Tyr Leu Leu Gly Ala Asp Cys Thr Val Phe Leu
            20                  25                  30

Asp His Glu Asp Ala Thr Lys Val Leu Ser Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ile Cys Lys Asp Asp Ile
            100                 105                 110

Asn Ser Tyr Glu Cys Trp Cys Gln Thr Gly Phe Glu Gly Lys Asn Cys
        115                 120                 125

Glu Leu Asp Val Thr Cys Asn Ile Lys Asn Gly Arg Cys Lys Gln Phe
    130                 135                 140

Cys Lys Leu Asp Ala Asp Asn Lys Val Val Cys Ser Cys Thr Thr Gly
145                 150                 155                 160

Tyr Gln Leu Ala Glu Asp Gln Lys Ser Cys Glu Pro Ala Val Pro Phe
                165                 170                 175

Pro Cys Gly Arg Val Ser Val Pro His Ile Ser Thr Thr His Thr Arg
            180                 185                 190

Ala Glu Thr Leu Phe Leu Asn Met Asp Tyr Glu Asn Ser Thr Thr Asp
        195                 200                 205

Tyr Glu Asn Ser Ala Glu Ala Glu Lys Asn Val Asp Asn Val Thr Gln
    210                 215                 220

Pro Leu Asn Asp Leu Thr Arg Ile Val Gly Gly Lys Thr Ala Lys Pro
225                 230                 235                 240

Gly Gln Phe Pro Trp Gln Val Leu Leu Lys Gly Lys Ile Asp Ala Phe
                245                 250                 255

Cys Gly Gly Ser Ile Ile Asn Glu Lys Trp Val Thr Ala Ala His
            260                 265                 270

Cys Ile Asn Pro Asp Val Glu Ile Thr Val Val Ala Gly Glu His Asn
        275                 280                 285

Thr Glu Glu Thr Glu His Thr Glu Gln Lys Arg Asn Val Ile Arg Thr
```

```
            290                 295                 300
Ile Leu His His Ser Tyr Asn Ala Ser Val Asn Lys Tyr Ser His Asp
305                 310                 315                 320

Ile Ala Leu Leu Glu Leu Asp Glu Pro Leu Thr Leu Asn Ser Tyr Val
                325                 330                 335

Thr Pro Ile Cys Val Ala Asp Arg Glu Tyr Thr Asn Thr Phe Leu Lys
            340                 345                 350

Phe Gly Tyr Gly Tyr Val Ser Gly Trp Gly Lys Val Phe Asn Lys Gly
        355                 360                 365

Arg Pro Ala Thr Ile Leu Gln Tyr Leu Lys Val Pro Leu Val Asp Arg
    370                 375                 380

Ala Thr Cys Leu Arg Ser Thr Lys Phe Thr Ile Tyr Asn Asn Met Phe
385                 390                 395                 400

Cys Ala Gly Phe His Glu Gly Gly Lys Asp Ser Cys Gln Gly Asp Ser
                405                 410                 415

Gly Gly Pro His Val Thr Glu Val Glu Gly Ile Asn Phe Leu Thr Gly
            420                 425                 430

Ile Ile Ser Trp Gly Glu Glu Cys Ala Met Lys Gly Lys Tyr Gly Ile
        435                 440                 445

Tyr Thr Lys Val Ser Arg Tyr Val Asn Trp Ile Lys Glu Lys Thr Lys
    450                 455                 460

Leu Thr
465

<210> SEQ ID NO 12
<211> LENGTH: 452
<212> TYPE: PRT
<213> ORGANISM: Canis familiaris

<400> SEQUENCE: 12

Met Ala Glu Ala Ser Gly Leu Val Thr Val Cys Leu Leu Gly Tyr Leu
1               5                   10                  15

Leu Ser Ala Glu Cys Ala Val Phe Leu Asp Arg Glu Asn Ala Thr Lys
            20                  25                  30

Ile Leu Ser Arg Pro Lys Arg Tyr Asn Ser Gly Lys Leu Glu Glu Phe
        35                  40                  45

Val Arg Gly Asn Leu Glu Arg Glu Cys Ile Glu Glu Lys Cys Ser Phe
    50                  55                  60

Glu Glu Ala Arg Glu Val Phe Glu Asn Thr Lys Thr Thr Glu Phe
65                  70                  75                  80

Trp Lys Gln Tyr Val Asp Gly Asp Gln Cys Glu Ser Asn Pro Cys Leu
                85                  90                  95

Asn Asp Gly Val Cys Lys Asp Asp Ile Asn Ser Tyr Glu Cys Trp Cys
            100                 105                 110

Arg Ala Gly Phe Glu Gly Lys Asn Cys Glu Leu Asp Val Thr Cys Asn
        115                 120                 125

Ile Lys Asn Gly Arg Cys Lys Gln Phe Cys Lys Leu Gly Pro Asp Asn
    130                 135                 140

Lys Val Val Cys Ser Cys Thr Thr Gly Tyr Gln Leu Ala Glu Asp Gln
145                 150                 155                 160

Arg Ser Cys Glu Pro Ala Val Pro Phe Pro Cys Gly Arg Val Ser Val
                165                 170                 175

Pro His Ile Ser Met Thr Arg Thr Arg Ala Glu Thr Leu Phe Ser Asn
            180                 185                 190
```

```
Met Asp Tyr Glu Asn Ser Thr Glu Val Glu Lys Ile Leu Asp Asn Val
        195                 200                 205

Thr Gln Pro Leu Asn Asp Phe Thr Arg Val Val Gly Gly Lys Asp Ala
210                 215                 220

Lys Pro Gly Gln Phe Pro Trp Gln Val Leu Leu Asn Gly Lys Val Asp
225                 230                 235                 240

Ala Phe Cys Gly Gly Ser Ile Ile Asn Glu Lys Trp Val Val Thr Ala
                245                 250                 255

Ala His Cys Ile Glu Pro Asp Val Lys Ile Thr Ile Val Ala Gly Glu
                260                 265                 270

His Asn Thr Glu Lys Arg Glu His Thr Glu Gln Lys Arg Asn Val Ile
            275                 280                 285

Arg Thr Ile Leu His His Ser Tyr Asn Ala Thr Ile Asn Lys Tyr Asn
290                 295                 300

His Asp Ile Ala Leu Leu Glu Leu Asp Glu Pro Leu Thr Leu Asn Ser
305                 310                 315                 320

Tyr Val Thr Pro Ile Cys Ile Ala Asp Arg Glu Tyr Ser Asn Ile Phe
                325                 330                 335

Leu Lys Phe Gly Ser Gly Tyr Val Ser Gly Trp Gly Arg Val Phe Asn
                340                 345                 350

Lys Gly Arg Ser Ala Ser Ile Leu Gln Tyr Leu Lys Val Pro Leu Val
            355                 360                 365

Asp Arg Ala Thr Cys Leu Arg Ser Thr Lys Phe Thr Ile Tyr Asn Asn
        370                 375                 380

Met Phe Cys Ala Gly Phe His Glu Gly Gly Lys Asp Ser Cys Gln Gly
385                 390                 395                 400

Asp Ser Gly Gly Pro His Val Thr Glu Val Glu Gly Ile Ser Phe Leu
                405                 410                 415

Thr Gly Ile Ile Ser Trp Gly Glu Glu Cys Ala Met Lys Gly Lys Tyr
                420                 425                 430

Gly Ile Tyr Thr Lys Val Ser Arg Tyr Val Asn Trp Ile Lys Glu Lys
            435                 440                 445

Thr Lys Leu Thr
    450

<210> SEQ ID NO 13
<211> LENGTH: 70
<212> TYPE: PRT
<213> ORGANISM: Canis familiaris

<400> SEQUENCE: 13

Met Ala Glu Ala Ser Gly Leu Val Thr Val Cys Leu Leu Gly Tyr Leu
1               5                   10                  15

Leu Ser Ala Glu Cys Ala Val Phe Leu Asp Arg Glu Asn Ala Thr Lys
                20                  25                  30

Ile Leu Ser Arg Pro Lys Arg His Ala Glu Gly Thr Phe Thr Ser Asp
            35                  40                  45

Val Ser Ser Tyr Leu Glu Gly Gln Ala Ala Lys Glu Phe Ile Ala Trp
        50                  55                  60

Leu Val Lys Gly Arg Gly
65                  70

<210> SEQ ID NO 14
<211> LENGTH: 462
<212> TYPE: PRT
<213> ORGANISM: Homo sapiens
```

<400> SEQUENCE: 14

| | | | | | | | | | | | | | |
|---|---|---|---|---|---|---|---|---|---|---|---|---|---|
|Met|Gln|Arg|Val|Asn|Met|Ile|Met|Ala|Glu|Ser|Pro|Ser|Leu|Ile|Thr
1||||5||||10||||15|

Ile Cys Leu Leu Gly Tyr Leu Leu Ser Ala Glu Cys Thr Val Phe Leu
        20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
50                  55                  60

Met Glu Glu Lys Cys Ser Phe Glu Glu Pro Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
                100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Pro Thr Glu Ala Glu
        195                 200                 205

Thr Ile Leu Asp Asn Ile Thr Gln Gly Thr Gln Ser Phe Asn Asp Phe
210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ala Ile Pro His His
290                 295                 300

Asn Tyr Asn Ala Ala Ile Asn Lys Tyr Asn His Asp Ile Ala Leu Leu
305                 310                 315                 320

Glu Leu Asp Glu Pro Leu Val Leu Asn Ser Tyr Val Thr Pro Ile Cys
                325                 330                 335

Ile Ala Asp Lys Glu Tyr Thr Asn Ile Phe Leu Lys Phe Gly Ser Gly
            340                 345                 350

Tyr Val Ser Gly Trp Ala Arg Val Phe His Lys Gly Arg Ser Ala Leu
        355                 360                 365

Val Leu Gln Tyr Leu Arg Val Pro Leu Val Asp Arg Ala Thr Cys Leu
370                 375                 380

Arg Ser Thr Lys Phe Thr Ile Tyr Asn Asn Met Phe Cys Ala Gly Phe
385                 390                 395                 400

His Glu Gly Gly Arg Asp Ser Cys Gln Gly Asp Ser Gly Gly Pro His

```
                    405                 410                 415

Val Thr Glu Val Glu Gly Thr Ser Phe Leu Thr Gly Ile Ile Ser Trp
                420                 425                 430

Gly Glu Glu Cys Ala Met Lys Gly Lys Tyr Gly Ile Tyr Thr Lys Val
            435                 440                 445

Ser Arg Tyr Val Asn Trp Ile Lys Glu Lys Thr Lys Leu Thr
        450                 455                 460

<210> SEQ ID NO 15
<211> LENGTH: 77
<212> TYPE: PRT
<213> ORGANISM: Artificial Sequence
<220> FEATURE:
<223> OTHER INFORMATION: constructed sequence

<400> SEQUENCE: 15

Met Gln Arg Val Asn Met Ile Met Ala Glu Ser Pro Ser Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg His Ala
            35                  40                  45

Glu Gly Thr Phe Thr Ser Asp Val Ser Ser Tyr Leu Glu Gly Gln Ala
        50                  55                  60

Ala Lys Glu Phe Ile Ala Trp Leu Val Lys Gly Arg Gly
65                  70                  75

<210> SEQ ID NO 16
<211> LENGTH: 446
<212> TYPE: PRT
<213> ORGANISM: Felis catus

<400> SEQUENCE: 16

Met Val Ser Gly Ser Arg Gly Pro Ala Leu Leu Cys Ser Leu Leu Gly
1               5                   10                  15

Leu Gln Ala Ser Leu Ala Ala Val Phe Leu Thr Gln Glu Glu Ala His
                20                  25                  30

Gly Val Leu Arg Arg His Arg Arg Ala Asn Ser Phe Leu Glu Glu Leu
            35                  40                  45

Arg Ser Gly Ser Leu Glu Arg Glu Cys Gly Glu Glu Arg Cys Ser Phe
        50                  55                  60

Glu Glu Ala Arg Glu Ile Phe Gln Asn Ala Glu Arg Thr Lys Gln Phe
65                  70                  75                  80

Trp Val Ser Tyr Val Asp Gly Asp Gln Cys Ala Ser Asn Pro Cys Gln
                85                  90                  95

Asn Gly Gly Ser Cys Glu Asp Gln Leu Gln Ser Tyr Ile Cys Phe Cys
            100                 105                 110

Leu Asp Asn Phe Glu Gly Arg Asn Cys Glu Thr Asn Lys Lys Asp Gln
        115                 120                 125

Leu Ile Cys Val Asn Glu Asn Gly Gly Cys Glu Gln Tyr Cys Ser Asp
    130                 135                 140

His Ala Glu Thr Arg Arg Ser Cys Arg Cys His Glu Gly Tyr Ala Leu
145                 150                 155                 160

Gln Asp Asp Gly Val Ser Cys Ala Pro Thr Val Glu Tyr Pro Cys Gly
                165                 170                 175

Arg Ile Pro Val Leu Glu Lys Arg Asn Gly Arg Asp Pro Gln Gly Arg
            180                 185                 190
```

```
Ile Val Gly Gly Lys Val Cys Pro Lys Gly Glu Cys Pro Trp Gln Ala
            195                 200                 205

Ala Leu Lys Leu Asp Gly Val Leu Val Cys Gly Gly Ala Leu Leu Asp
    210                 215                 220

Ala Ala Trp Val Val Ser Ala Ala His Cys Phe Asp Arg Ile Arg Asn
225                 230                 235                 240

Trp Glu Asn Leu Thr Val Val Leu Gly Glu His Asp Leu Arg Lys Glu
                245                 250                 255

Glu Gly Glu Glu Gln Glu Arg His Val Ala Gln Ile Ile Pro Asp
                260                 265                 270

Lys Tyr Ile Pro Arg Lys Thr Asn His Asp Ile Ala Leu Leu Arg Leu
            275                 280                 285

Arg Thr Pro Val Ala Phe Thr Asn His Val Val Pro Leu Cys Leu Pro
            290                 295                 300

Glu Lys Ser Phe Ser Glu Arg Thr Leu Ala Phe Ile Arg Phe Ser Thr
305                 310                 315                 320

Val Ser Gly Trp Gly Gln Leu Leu Asp Arg Gly Ile Thr Ala Leu Glu
                325                 330                 335

Leu Met Ala Ile Asp Val Pro Arg Val Met Thr Gln Asp Cys Gln Glu
            340                 345                 350

Gln Ser His Arg Lys Ala Gly Ser Pro Ala Ile Thr Glu Asn Met Phe
            355                 360                 365

Cys Ala Gly Tyr Leu Asp Gly Ser Lys Asp Ala Cys Lys Gly Asp Ser
        370                 375                 380

Gly Gly Pro His Ala Thr Lys Phe Gln Gly Thr Trp Tyr Leu Thr Gly
385                 390                 395                 400

Ile Val Ser Trp Gly Glu Gly Cys Ala Ala Glu Gly His Phe Gly Val
                405                 410                 415

Tyr Thr Arg Val Ser Gln Tyr Ile Glu Trp Leu Arg Arg Leu Met Ser
            420                 425                 430

Gln Ser Pro Thr Ser Gly Gly Leu Leu Arg Ala Pro Leu Pro
            435                 440                 445

<210> SEQ ID NO 17
<211> LENGTH: 71
<212> TYPE: PRT
<213> ORGANISM: Artificial Sequence
<220> FEATURE:
<223> OTHER INFORMATION: constructed sequence

<400> SEQUENCE: 17

Met Val Ser Gly Ser Arg Gly Pro Ala Leu Leu Cys Ser Leu Leu Gly
1               5                   10                  15

Leu Gln Ala Ser Leu Ala Ala Val Phe Leu Thr Gln Glu Glu Ala His
            20                  25                  30

Gly Val Leu Arg Arg His Arg Arg His Ala Glu Gly Thr Phe Thr Ser
        35                  40                  45

Asp Val Ser Ser Tyr Leu Glu Gly Gln Ala Ala Lys Glu Phe Ile Ala
    50                  55                  60

Trp Leu Val Lys Gly Arg Gly
65                  70

<210> SEQ ID NO 18
<211> LENGTH: 446
<212> TYPE: PRT
<213> ORGANISM: Canis familiaris
```

<400> SEQUENCE: 18

```
Met Val Ala Trp Ala Gly Glu Leu Ala Leu Leu Cys Phe Leu Leu Gly
1               5                   10                  15

Leu Gln Gly Ser Leu Ala Ala Val Phe Leu Thr Gln Glu Glu Ala Gln
            20                  25                  30

Gly Val Leu His Arg Gln Arg Ala Asn Ser Phe Leu Glu Glu Leu
        35                  40                  45

Arg Ala Gly Ser Leu Glu Arg Glu Cys Arg Glu Glu Gln Cys Ser Phe
50                  55                  60

Glu Glu Ala Arg Glu Ile Phe Gln Asp Val Asp Arg Thr Arg Gln Phe
65                  70                  75                  80

Trp Ile Ser Tyr Lys Asp Gly Asp Gln Cys Ala Ser Asn Pro Cys Gln
                85                  90                  95

Asn Gly Gly Ser Cys Glu Asp Gln Leu Gln Ser Tyr Ile Cys Phe Cys
                100                 105                 110

Pro Asp Asp Phe Gln Gly Arg Asn Cys Glu Thr Asp Lys Lys Asp Gln
            115                 120                 125

Leu Ile Cys Met Asn Glu Asn Gly Gly Cys Gln Gln Tyr Cys Ser Asp
130                 135                 140

His Ala Glu Ala Arg Arg Ser Cys Trp Cys His Glu Gly Tyr Thr Leu
145                 150                 155                 160

Gln Asp Asp Gly Val Ser Cys Met Pro Ile Val Glu Tyr Pro Cys Gly
                165                 170                 175

Lys Ile Pro Val Leu Glu Lys Arg Ile Gly Ser Asn Pro Gln Gly Arg
            180                 185                 190

Ile Val Gly Gly Lys Val Cys Pro Lys Gly Glu Cys Pro Trp Gln Ala
        195                 200                 205

Ala Val Lys Val Asp Gly Lys Leu Leu Cys Gly Gly Thr Leu Ile Asp
210                 215                 220

Ala Ala Trp Val Val Ser Ala Ala His Cys Phe Glu Arg Ile Lys Asn
225                 230                 235                 240

Trp Lys Asn Leu Thr Val Val Leu Gly Glu His Asp Leu Ser Glu Asp
                245                 250                 255

Asp Gly Asp Glu Gln Glu Arg His Val Ala Arg Val Ile Val Pro Asp
            260                 265                 270

Lys Tyr Ile Pro Leu Lys Thr Asn His Asp Ile Ala Leu Leu His Leu
        275                 280                 285

Arg Thr Pro Val Ala Tyr Thr Asp His Val Val Pro Leu Cys Leu Pro
290                 295                 300

Glu Lys Thr Phe Ser Glu Arg Thr Leu Ala Phe Ile Arg Phe Ser Thr
305                 310                 315                 320

Val Ser Gly Trp Gly Gln Leu Leu Asp Arg Gly Ala Thr Ala Leu Gln
                325                 330                 335

Leu Met Ala Ile Asp Val Pro Arg Val Met Thr Gln Asp Cys Gln Glu
            340                 345                 350

Gln Ser Arg Arg Arg Ser Gly Ser Pro Ala Ile Thr Glu Asn Met Phe
        355                 360                 365

Cys Ala Gly Tyr Leu Asp Gly Ser Lys Asp Ala Cys Gln Gly Asp Ser
370                 375                 380

Gly Gly Pro His Ala Thr Lys Phe Gln Gly Thr Trp Tyr Leu Thr Gly
385                 390                 395                 400

Val Val Ser Trp Gly Glu Gly Cys Ala Ala Glu Gly His Phe Gly Val
```

```
                              405                 410                 415
Tyr Thr Arg Val Ser Gln Tyr Ile Glu Trp Leu Arg Gln Leu Met Val
                420                 425                 430

Ser Ser His Thr Leu Arg Gly Leu Leu Arg Ala Pro Leu Pro
            435                 440                 445

<210> SEQ ID NO 19
<211> LENGTH: 71
<212> TYPE: PRT
<213> ORGANISM: Artificial Sequence
<220> FEATURE:
<223> OTHER INFORMATION: constructed sequence

<400> SEQUENCE: 19

Met Val Ala Trp Ala Gly Glu Leu Ala Leu Leu Cys Phe Leu Leu Gly
1               5                   10                  15

Leu Gln Gly Ser Leu Ala Ala Val Phe Leu Thr Gln Glu Glu Ala Gln
            20                  25                  30

Gly Val Leu His Arg Gln Arg His Ala Glu Gly Thr Phe Thr Ser
        35                  40                  45

Asp Val Ser Ser Tyr Leu Glu Gly Gln Ala Ala Lys Glu Phe Ile Ala
    50                  55                  60

Trp Leu Val Lys Gly Arg Gly
65                  70

<210> SEQ ID NO 20
<211> LENGTH: 466
<212> TYPE: PRT
<213> ORGANISM: Homo sapiens

<400> SEQUENCE: 20

Met Val Ser Gln Ala Leu Arg Leu Leu Cys Leu Leu Leu Gly Leu Gln
1               5                   10                  15

Gly Cys Leu Ala Ala Gly Gly Val Ala Lys Ala Ser Gly Gly Glu Thr
            20                  25                  30

Arg Asp Met Pro Trp Lys Pro Gly Pro His Arg Val Phe Val Thr Gln
        35                  40                  45

Glu Glu Ala His Gly Val Leu His Arg Arg Arg Ala Asn Ala Phe
    50                  55                  60

Leu Glu Glu Leu Arg Pro Gly Ser Leu Glu Arg Glu Cys Lys Glu Glu
65                  70                  75                  80

Gln Cys Ser Phe Glu Glu Ala Arg Glu Ile Phe Lys Asp Ala Glu Arg
                85                  90                  95

Thr Lys Leu Phe Trp Ile Ser Tyr Ser Asp Gly Asp Gln Cys Ala Ser
            100                 105                 110

Ser Pro Cys Gln Asn Gly Gly Ser Cys Lys Asp Gln Leu Gln Ser Tyr
        115                 120                 125

Ile Cys Phe Cys Leu Pro Ala Phe Glu Gly Arg Asn Cys Glu Thr His
    130                 135                 140

Lys Asp Asp Gln Leu Ile Cys Val Asn Glu Asn Gly Gly Cys Glu Gln
145                 150                 155                 160

Tyr Cys Ser Asp His Thr Gly Thr Lys Arg Ser Cys Arg Cys His Glu
                165                 170                 175

Gly Tyr Ser Leu Leu Ala Asp Gly Val Ser Cys Thr Pro Thr Val Glu
            180                 185                 190

Tyr Pro Cys Gly Lys Ile Pro Ile Leu Glu Lys Arg Asn Ala Ser Lys
        195                 200                 205
```

```
Pro Gln Gly Arg Ile Val Gly Gly Lys Val Cys Pro Lys Gly Glu Cys
    210                 215                 220
Pro Trp Gln Val Leu Leu Leu Val Asn Gly Ala Gln Leu Cys Gly Gly
225                 230                 235                 240
Thr Leu Ile Asn Thr Ile Trp Val Val Ser Ala His Cys Phe Asp
        245                 250                 255
Lys Ile Lys Asn Trp Arg Asn Leu Ile Ala Val Leu Gly Glu His Asp
            260                 265                 270
Leu Ser Glu His Asp Gly Asp Glu Gln Ser Arg Arg Val Ala Gln Val
        275                 280                 285
Ile Ile Pro Ser Thr Tyr Val Pro Gly Thr Thr Asn His Asp Ile Ala
    290                 295                 300
Leu Leu Arg Leu His Gln Pro Val Val Leu Thr Asp His Val Val Pro
305                 310                 315                 320
Leu Cys Leu Pro Glu Arg Thr Phe Ser Glu Arg Thr Leu Ala Phe Val
                325                 330                 335
Arg Phe Ser Leu Val Ser Gly Trp Gly Gln Leu Leu Asp Arg Gly Ala
            340                 345                 350
Thr Ala Leu Glu Leu Met Val Leu Asn Val Pro Arg Leu Met Thr Gln
        355                 360                 365
Asp Cys Leu Gln Gln Ser Arg Lys Val Gly Asp Ser Pro Asn Ile Thr
    370                 375                 380
Glu Tyr Met Phe Cys Ala Gly Tyr Ser Asp Gly Ser Lys Asp Ser Cys
385                 390                 395                 400
Lys Gly Asp Ser Gly Gly Pro His Ala Thr His Tyr Arg Gly Thr Trp
                405                 410                 415
Tyr Leu Thr Gly Ile Val Ser Trp Gly Gln Gly Cys Ala Thr Val Gly
            420                 425                 430
His Phe Gly Val Tyr Thr Arg Val Ser Gln Tyr Ile Glu Trp Leu Gln
        435                 440                 445
Lys Leu Met Arg Ser Glu Pro Arg Pro Gly Val Leu Leu Arg Ala Pro
    450                 455                 460
Phe Pro
465

<210> SEQ ID NO 21
<211> LENGTH: 91
<212> TYPE: PRT
<213> ORGANISM: Artificial Sequence
<220> FEATURE:
<223> OTHER INFORMATION: constructed sequence

<400> SEQUENCE: 21

Met Val Ser Gln Ala Leu Arg Leu Leu Cys Leu Leu Leu Gly Leu Gln
1               5                   10                  15
Gly Cys Leu Ala Ala Gly Gly Val Ala Lys Ala Ser Gly Gly Glu Thr
            20                  25                  30
Arg Asp Met Pro Trp Lys Pro Gly Pro His Arg Val Phe Val Thr Gln
        35                  40                  45
Glu Glu Ala His Gly Val Leu His Arg Arg Arg His Ala Glu Gly
    50                  55                  60
Thr Phe Thr Ser Asp Val Ser Ser Tyr Leu Glu Gly Gln Ala Ala Lys
65                  70                  75                  80
Glu Phe Ile Ala Trp Leu Val Lys Gly Arg Gly
                85                  90
```

<210> SEQ ID NO 22
<211> LENGTH: 444
<212> TYPE: PRT
<213> ORGANISM: Homo sapiens

<400> SEQUENCE: 22

```
Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
            20                  25                  30

Leu His Arg Arg Arg Arg Ala Asn Ala Phe Leu Glu Glu Leu Arg Pro
        35                  40                  45

Gly Ser Leu Glu Arg Glu Cys Lys Glu Glu Gln Cys Ser Phe Glu Glu
    50                  55                  60

Ala Arg Glu Ile Phe Lys Asp Ala Glu Arg Thr Lys Leu Phe Trp Ile
65                  70                  75                  80

Ser Tyr Ser Asp Gly Asp Gln Cys Ala Ser Pro Cys Gln Asn Gly
                85                  90                  95

Gly Ser Cys Lys Asp Gln Leu Gln Ser Tyr Ile Cys Phe Cys Leu Pro
            100                 105                 110

Ala Phe Glu Gly Arg Asn Cys Glu Thr His Lys Asp Asp Gln Leu Ile
        115                 120                 125

Cys Val Asn Glu Asn Gly Gly Cys Glu Gln Tyr Cys Ser Asp His Thr
    130                 135                 140

Gly Thr Lys Arg Ser Cys Arg Cys His Glu Gly Tyr Ser Leu Leu Ala
145                 150                 155                 160

Asp Gly Val Ser Cys Thr Pro Thr Val Glu Tyr Pro Cys Gly Lys Ile
                165                 170                 175

Pro Ile Leu Glu Lys Arg Asn Ala Ser Lys Pro Gln Gly Arg Ile Val
            180                 185                 190

Gly Gly Lys Val Cys Pro Lys Gly Glu Cys Pro Trp Gln Val Leu Leu
        195                 200                 205

Leu Val Asn Gly Ala Gln Leu Cys Gly Gly Thr Leu Ile Asn Thr Ile
    210                 215                 220

Trp Val Val Ser Ala Ala His Cys Phe Asp Lys Ile Lys Asn Trp Arg
225                 230                 235                 240

Asn Leu Ile Ala Val Leu Gly Glu His Asp Leu Ser Glu His Asp Gly
                245                 250                 255

Asp Glu Gln Ser Arg Arg Val Ala Gln Val Ile Ile Pro Ser Thr Tyr
            260                 265                 270

Val Pro Gly Thr Thr Asn His Asp Ile Ala Leu Leu Arg Leu His Gln
        275                 280                 285

Pro Val Val Leu Thr Asp His Val Val Pro Leu Cys Leu Pro Glu Arg
    290                 295                 300

Thr Phe Ser Glu Arg Thr Leu Ala Phe Val Arg Phe Ser Leu Val Ser
305                 310                 315                 320

Gly Trp Gly Gln Leu Leu Asp Arg Gly Ala Thr Ala Leu Glu Leu Met
                325                 330                 335

Val Leu Asn Val Pro Arg Leu Met Thr Gln Asp Cys Leu Gln Gln Ser
            340                 345                 350

Arg Lys Val Gly Asp Ser Pro Asn Ile Thr Glu Tyr Met Phe Cys Ala
        355                 360                 365

Gly Tyr Ser Asp Gly Ser Lys Asp Ser Cys Lys Gly Asp Ser Gly Gly
```

```
                370                 375                 380
Pro His Ala Thr His Tyr Arg Gly Thr Trp Tyr Leu Thr Gly Ile Val
385                 390                 395                 400

Ser Trp Gly Gln Gly Cys Ala Thr Val Gly His Phe Gly Val Tyr Thr
                405                 410                 415

Arg Val Ser Gln Tyr Ile Glu Trp Leu Gln Lys Leu Met Arg Ser Glu
                420                 425                 430

Pro Arg Pro Gly Val Leu Leu Arg Ala Pro Phe Pro
            435                 440

<210> SEQ ID NO 23
<211> LENGTH: 69
<212> TYPE: PRT
<213> ORGANISM: Artificial Sequence
<220> FEATURE:
<223> OTHER INFORMATION: constructed sequence

<400> SEQUENCE: 23

Met Val Ser Gln Ala Leu Arg Leu Leu Cys Leu Leu Leu Gly Leu Gln
1               5                   10                  15

Gly Cys Leu Ala Ala Val Phe Val Thr Gln Glu Glu Ala His Gly Val
                20                  25                  30

Leu His Arg Arg Arg His Ala Glu Gly Thr Phe Thr Ser Asp Val
            35                  40                  45

Ser Ser Tyr Leu Glu Gly Gln Ala Ala Lys Glu Phe Ile Ala Trp Leu
        50                  55                  60

Val Lys Gly Arg Gly
65

<210> SEQ ID NO 24
<211> LENGTH: 622
<212> TYPE: PRT
<213> ORGANISM: Felis catus

<400> SEQUENCE: 24

Met Ala His Ile Arg Gly Leu Trp Leu Pro Gly Cys Leu Ala Leu Ala
1               5                   10                  15

Ala Leu Cys Ser Leu Val His Ser Gln His Val Phe Leu Ala Pro Gln
                20                  25                  30

Gln Ala Leu Ser Leu Leu Gln Arg Val Arg Arg Ala Asn Ser Gly Phe
            35                  40                  45

Leu Glu Glu Val Arg Lys Gly Asn Leu Glu Arg Glu Cys Val Glu Glu
        50                  55                  60

Leu Cys Ser Tyr Glu Glu Ala Phe Glu Ala Leu Glu Ser Ser Phe Ala
65              70                  75                  80

Thr Asp Val Phe Trp Ala Lys Tyr Thr Ala Cys Glu Ser Val Arg Lys
                85                  90                  95

Pro Arg Asp Lys Leu Met Glu Cys Leu Glu Gly Asn Cys Ala Glu Gly
            100                 105                 110

Leu Gly Met Asn Tyr Arg Gly Asn Val Asn Phe Thr Arg Ser Gly Ile
        115                 120                 125

Glu Cys Gln Leu Trp Arg Ser Arg Tyr Pro His Lys Pro Glu Ile Asn
    130                 135                 140

Tyr Thr Thr His Pro Gly Ala Asp Leu Lys Glu Asn Phe Cys Arg Asn
145                 150                 155                 160

Pro Asp Gly Ser Thr Thr Gly Pro Trp Cys Tyr Thr Thr Asp Pro Thr
                165                 170                 175
```

```
Val Arg Arg Glu Glu Cys Ser Ile Pro Ile Cys Gly Gln Gly Gly Val
            180                 185                 190

Thr Val Gln Pro Thr Pro Arg Ser Arg Asn Ser Thr Val Asn Leu Pro
        195                 200                 205

Pro Pro Ser Asp Ser Cys Ile Pro Glu Arg Gly Arg Tyr Tyr His Gly
    210                 215                 220

Arg Leu Ala Val Thr Thr His Gly Ser Pro Cys Leu Ala Trp Asp Ser
225                 230                 235                 240

Ser Gln Ala Lys Ala Leu Ser Glu Asn Gln Asp Phe Asn Pro Leu Val
                245                 250                 255

Pro Leu Glu Lys Asn Phe Cys Arg Asn Pro Asp Gly Asp Glu Glu Gly
            260                 265                 270

Val Trp Cys Tyr Val Ser Gly Pro Gly Asp Phe Glu Tyr Cys Asn
        275                 280                 285

Leu Asp Tyr Cys Glu Glu Pro Phe Glu Asp Val Ser Asp Gly Leu Ala
    290                 295                 300

Glu Asp Pro Glu Ala Pro Ile Glu Gly Arg Thr Thr Ala Glu Glu Phe
305                 310                 315                 320

Gln Thr Phe Phe Asn Glu Lys Thr Phe Gly Ala Gly Glu Ala Asp Cys
                325                 330                 335

Gly Leu Arg Pro Leu Phe Glu Lys Lys Ser Leu Lys Asp Lys Thr Glu
            340                 345                 350

Glu Glu Leu Leu Asp Ser Tyr Ile Asp Gly Arg Ile Val Lys Gly Trp
        355                 360                 365

Asp Ala Glu Ile Gly Ile Ala Pro Trp Gln Val Met Leu Phe Arg Lys
    370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Ser Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Leu Lys Leu Lys Lys Pro Ile Ala Phe Ser Ser Tyr Ile His Pro
465                 470                 475                 480

Val Cys Leu Pro Asp Lys Ala Thr Val Ala Arg Leu Ile Gln Thr Gly
                485                 490                 495

Tyr Lys Gly Arg Val Thr Gly Trp Gly Asn Leu Lys Glu Thr Trp Thr
            500                 505                 510

Thr Ser Val Gly Glu Val Gln Pro Ser Val Leu Gln Val Val Asn Leu
        515                 520                 525

Pro Leu Val Glu Gln Pro Val Cys Arg Ala Ser Thr Arg Ile Arg Ile
    530                 535                 540

Thr Asp Asn Met Phe Cys Ala Gly Tyr Lys Pro Asn Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590
```

Gly Cys Asp Arg Asp Gly Lys Tyr Gly Phe Tyr Thr His Val Phe Arg
            595                 600                 605

Leu Lys Lys Trp Ile Arg Lys Val Ile Asp Gln Ser Gly Ser
        610                 615                 620

<210> SEQ ID NO 25
<211> LENGTH: 74
<212> TYPE: PRT
<213> ORGANISM: Artificial Sequence
<220> FEATURE:
<223> OTHER INFORMATION: constructed sequence

<400> SEQUENCE: 25

Met Ala His Ile Arg Gly Leu Trp Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Leu Ser Leu Leu Gln Arg Val Arg Arg His Ala Glu Gly Thr
        35                  40                  45

Phe Thr Ser Asp Val Ser Ser Tyr Leu Glu Gly Gln Ala Ala Lys Glu
    50                  55                  60

Phe Ile Ala Trp Leu Val Lys Gly Arg Gly
65                  70

<210> SEQ ID NO 26
<211> LENGTH: 621
<212> TYPE: PRT
<213> ORGANISM: Canis familiaris

<400> SEQUENCE: 26

Met Ala His Ile Arg Gly Leu Trp Leu Pro Gly Cys Leu Val Ile Leu
1               5                   10                  15

Phe Ser Leu Ala His Ser Gln His Val Phe Leu Asp Pro Gln Gln Ala
            20                  25                  30

Leu Ser Leu Leu His Arg Val Arg Arg Ala Asn Ser Gly Phe Leu Glu
        35                  40                  45

Glu Leu Arg Lys Gly Asn Leu Glu Arg Glu Cys Val Glu Glu Gln Cys
    50                  55                  60

Asn Tyr Glu Glu Ala Phe Glu Ala Leu Glu Ser Ser Thr Ala Thr Asp
65                  70                  75                  80

Val Phe Trp Ser Lys Tyr Thr Ala Cys Glu Pro Val Arg Lys Pro Arg
            85                  90                  95

Glu Lys Leu Val Glu Cys Leu Glu Gly Ser Cys Ala Glu Gly Leu Gly
            100                 105                 110

Met Asn Tyr Arg Gly Asn Val Ser Phe Thr Arg Ser Gly Ile Glu Cys
        115                 120                 125

Gln Leu Trp Arg Ser Arg Tyr Pro His Lys Pro Glu Ile Asn Ser Thr
    130                 135                 140

Thr His Pro Gly Ala Asp Leu Gln Glu Asn Phe Cys Arg Asn Pro Asp
145                 150                 155                 160

Gly Ser Thr Thr Gly Pro Trp Cys Tyr Thr Ile Asp Pro Thr Val Arg
            165                 170                 175

Arg Glu Glu Cys Ser Ile Ser Leu Cys Gly Gln Gly Gly Val Thr
            180                 185                 190

Val Pro Leu Thr Pro Arg Ser Gly Gly Pro Thr Val Asn Leu Ser Pro
        195                 200                 205

Pro Ser Glu His Cys Ile Pro Glu Arg Gly Arg Tyr Tyr Gln Gly Arg

```
            210                 215                 220
Leu Ala Val Thr Thr His Gly Ser Pro Cys Leu Ala Trp Ala Ser Arg
225                 230                 235                 240

Gln Ala Lys Ala Leu Ser Lys Asp Gln Asp Phe Asn Pro Ala Val Pro
                245                 250                 255

Leu Val Glu Asn Phe Cys Arg Asn Pro Asp Gly Asp Glu Glu Gly Ala
                260                 265                 270

Trp Cys Tyr Val Ser Glu Glu Pro Gly Gly Phe Glu Tyr Cys Asp Leu
                275                 280                 285

Asp Tyr Cys Glu Glu Pro Val Glu Glu Val Gly Asp Gly Leu Ala Glu
            290                 295                 300

Asp Gln Asp Thr Ala Ile Glu Gly Arg Thr Thr Ala Glu Glu Phe Gln
305                 310                 315                 320

Pro Phe Phe Asn Glu Lys Thr Phe Gly Ala Gly Glu Ala Asp Cys Gly
                325                 330                 335

Leu Arg Pro Leu Phe Glu Lys Arg Ser Val Lys Asp Lys Thr Glu Gly
                340                 345                 350

Glu Leu Leu Glu Ser Tyr Ile Asp Gly Arg Ile Val Glu Gly Trp Asp
                355                 360                 365

Ala Glu Ile Gly Leu Ala Pro Trp Gln Val Met Leu Phe Arg Lys Ser
370                 375                 380

Pro Gln Glu Leu Leu Cys Gly Ala Ser Leu Ile Ser Asp Arg Trp Val
385                 390                 395                 400

Leu Thr Ala Ala His Cys Leu Leu Tyr Pro Pro Trp Asp Lys Asn Phe
                405                 410                 415

Thr Glu Asn Asp Leu Leu Val Arg Ile Gly Lys His Ser Arg Thr Arg
                420                 425                 430

Tyr Glu Arg Ser Ile Glu Lys Ile Ser Met Leu Glu Lys Ile Tyr Ile
                435                 440                 445

His Pro Arg Tyr Asn Trp Arg Glu Asn Leu Asp Arg Asp Ile Ala Leu
                450                 455                 460

Leu Lys Leu Lys Lys Pro Val Asn Phe Ser Asn Tyr Ile His Pro Val
465                 470                 475                 480

Cys Leu Pro Asp Arg Asp Thr Ala Thr Arg Leu Leu Gln Ala Gly Tyr
                485                 490                 495

Lys Gly Arg Val Thr Gly Trp Gly Asn Leu Arg Glu Thr Trp Thr Ser
                500                 505                 510

Ser Ile Gly Glu Val Gln Pro Arg Val Leu Gln Val Val Asn Leu Pro
            515                 520                 525

Ile Val Asp Arg Gln Val Cys Lys Ala Ser Thr Arg Ile Arg Ile Thr
530                 535                 540

Asp Asn Met Phe Cys Ala Gly Tyr Lys Pro Asn Glu Gly Lys Arg Gly
545                 550                 555                 560

Asp Ala Cys Glu Gly Asp Ser Gly Gly Pro Phe Val Met Lys Ser Pro
                565                 570                 575

Phe Asn Asn Arg Trp Tyr Gln Met Gly Ile Val Ser Trp Gly Glu Gly
                580                 585                 590

Cys Asp Arg Asp Gly Lys Tyr Gly Phe Tyr Thr His Val Phe Arg Leu
                595                 600                 605

Lys Lys Trp Ile Gln Lys Val Ile Glu Lys Ser Gly Gly
610                 615                 620
```

<210> SEQ ID NO 27

```
<211> LENGTH: 72
<212> TYPE: PRT
<213> ORGANISM: Artificial Sequence
<220> FEATURE:
<223> OTHER INFORMATION: constructed sequence

<400> SEQUENCE: 27

Met Ala His Ile Arg Gly Leu Trp Leu Pro Gly Cys Leu Val Ile Leu
1               5                   10                  15

Phe Ser Leu Ala His Ser Gln His Val Phe Leu Asp Pro Gln Gln Ala
            20                  25                  30

Leu Ser Leu Leu His Arg Val Arg Arg His Ala Glu Gly Thr Phe Thr
        35                  40                  45

Ser Asp Val Ser Ser Tyr Leu Glu Gly Gln Ala Ala Lys Glu Phe Ile
    50                  55                  60

Ala Trp Leu Val Lys Gly Arg Gly
65                  70

<210> SEQ ID NO 28
<211> LENGTH: 622
<212> TYPE: PRT
<213> ORGANISM: Homo sapiens

<400> SEQUENCE: 28

Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg Ala Asn Thr Phe Leu
        35                  40                  45

Glu Glu Val Arg Lys Gly Asn Leu Glu Arg Glu Cys Val Glu Glu Thr
    50                  55                  60

Cys Ser Tyr Glu Glu Ala Phe Glu Ala Leu Glu Ser Ser Thr Ala Thr
65                  70                  75                  80

Asp Val Phe Trp Ala Lys Tyr Thr Ala Cys Glu Thr Ala Arg Thr Pro
                85                  90                  95

Arg Asp Lys Leu Ala Ala Cys Leu Glu Gly Asn Cys Ala Glu Gly Leu
            100                 105                 110

Gly Thr Asn Tyr Arg Gly His Val Asn Ile Thr Arg Ser Gly Ile Glu
        115                 120                 125

Cys Gln Leu Trp Arg Ser Arg Tyr Pro His Lys Pro Glu Ile Asn Ser
    130                 135                 140

Thr Thr His Pro Gly Ala Asp Leu Gln Glu Asn Phe Cys Arg Asn Pro
145                 150                 155                 160

Asp Ser Ser Thr Thr Gly Pro Trp Cys Tyr Thr Thr Asp Pro Thr Val
                165                 170                 175

Arg Arg Gln Glu Cys Ser Ile Pro Val Cys Gly Gln Asp Gln Val Thr
            180                 185                 190

Val Ala Met Thr Pro Arg Ser Glu Gly Ser Ser Val Asn Leu Ser Pro
        195                 200                 205

Pro Leu Glu Gln Cys Val Pro Asp Arg Gly Gln Gln Tyr Gln Gly Arg
    210                 215                 220

Leu Ala Val Thr Thr His Gly Leu Pro Cys Leu Ala Trp Ala Ser Ala
225                 230                 235                 240

Gln Ala Lys Ala Leu Ser Lys His Gln Asp Phe Asn Ser Ala Val Gln
                245                 250                 255
```

Leu Val Glu Asn Phe Cys Arg Asn Pro Asp Gly Asp Glu Glu Gly Val
            260                 265                 270

Trp Cys Tyr Val Ala Gly Lys Pro Gly Asp Phe Gly Tyr Cys Asp Leu
        275                 280                 285

Asn Tyr Cys Glu Glu Ala Val Glu Glu Glu Thr Gly Asp Gly Leu Asp
        290                 295                 300

Glu Asp Ser Asp Arg Ala Ile Glu Gly Arg Thr Ala Thr Ser Glu Tyr
305                 310                 315                 320

Gln Thr Phe Phe Asn Pro Arg Thr Phe Gly Ser Gly Glu Ala Asp Cys
                325                 330                 335

Gly Leu Arg Pro Leu Phe Glu Lys Lys Ser Leu Glu Asp Lys Thr Glu
            340                 345                 350

Arg Glu Leu Leu Glu Ser Tyr Ile Asp Gly Arg Ile Val Glu Gly Ser
            355                 360                 365

Asp Ala Glu Ile Gly Met Ser Pro Trp Gln Val Met Leu Phe Arg Lys
        370                 375                 380

Ser Pro Gln Glu Leu Leu Cys Gly Ala Ser Leu Ile Ser Asp Arg Trp
385                 390                 395                 400

Val Leu Thr Ala Ala His Cys Leu Leu Tyr Pro Pro Trp Asp Lys Asn
                405                 410                 415

Phe Thr Glu Asn Asp Leu Leu Val Arg Ile Gly Lys His Ser Arg Thr
            420                 425                 430

Arg Tyr Glu Arg Asn Ile Glu Lys Ile Ser Met Leu Glu Lys Ile Tyr
        435                 440                 445

Ile His Pro Arg Tyr Asn Trp Arg Glu Asn Leu Asp Arg Asp Ile Ala
    450                 455                 460

Leu Met Lys Leu Lys Lys Pro Val Ala Phe Ser Asp Tyr Ile His Pro
465                 470                 475                 480

Val Cys Leu Pro Asp Arg Glu Thr Ala Ala Ser Leu Leu Gln Ala Gly
                485                 490                 495

Tyr Lys Gly Arg Val Thr Gly Trp Gly Asn Leu Lys Glu Thr Trp Thr
            500                 505                 510

Ala Asn Val Gly Lys Gly Gln Pro Ser Val Leu Gln Val Val Asn Leu
        515                 520                 525

Pro Ile Val Glu Arg Pro Val Cys Lys Asp Ser Thr Arg Ile Arg Ile
530                 535                 540

Thr Asp Asn Met Phe Cys Ala Gly Tyr Lys Pro Asp Glu Gly Lys Arg
545                 550                 555                 560

Gly Asp Ala Cys Glu Gly Asp Ser Gly Gly Pro Phe Val Met Lys Ser
                565                 570                 575

Pro Phe Asn Asn Arg Trp Tyr Gln Met Gly Ile Val Ser Trp Gly Glu
            580                 585                 590

Gly Cys Asp Arg Asp Gly Lys Tyr Gly Phe Tyr Thr His Val Phe Arg
        595                 600                 605

Leu Lys Lys Trp Ile Gln Lys Val Ile Asp Gln Phe Gly Glu
    610                 615                 620

<210> SEQ ID NO 29
<211> LENGTH: 74
<212> TYPE: PRT
<213> ORGANISM: Artificial Sequence
<220> FEATURE:
<223> OTHER INFORMATION: constructed sequence

<400> SEQUENCE: 29

```
Met Ala His Val Arg Gly Leu Gln Leu Pro Gly Cys Leu Ala Leu Ala
1               5                   10                  15

Ala Leu Cys Ser Leu Val His Ser Gln His Val Phe Leu Ala Pro Gln
            20                  25                  30

Gln Ala Arg Ser Leu Leu Gln Arg Val Arg Arg His Ala Glu Gly Thr
            35                  40                  45

Phe Thr Ser Asp Val Ser Ser Tyr Leu Glu Gly Gln Ala Ala Lys Glu
            50                  55                  60

Phe Ile Ala Trp Leu Val Lys Gly Arg Gly
65                  70

<210> SEQ ID NO 30
<211> LENGTH: 466
<212> TYPE: PRT
<213> ORGANISM: Felis catus

<400> SEQUENCE: 30

Met Arg Cys Leu Asn Met Ile Met Ala Glu Pro Gly Leu Ile Thr
1               5                   10                  15

Ile Cys Leu Leu Gly Tyr Leu Leu Gly Ala Asp Cys Thr Val Phe Leu
            20                  25                  30

Asp His Glu Asp Ala Thr Lys Val Leu Ser Arg Pro Lys Arg Tyr Asn
            35                  40                  45

Ser Gly Lys Leu Glu Glu Phe Val Gln Gly Asn Leu Glu Arg Glu Cys
            50                  55                  60

Met Glu Glu Lys Cys Ser Phe Glu Glu Ala Arg Glu Val Phe Glu Asn
65                  70                  75                  80

Thr Glu Lys Thr Thr Glu Phe Trp Lys Gln Tyr Val Asp Gly Asp Gln
                85                  90                  95

Cys Glu Ser Asn Pro Cys Leu Asn Gly Gly Ile Cys Lys Asp Asp Ile
            100                 105                 110

Asn Ser Tyr Glu Cys Trp Cys Gln Thr Gly Phe Glu Gly Lys Asn Cys
            115                 120                 125

Glu Leu Asp Val Thr Cys Asn Ile Lys Asn Gly Arg Cys Lys Gln Phe
130                 135                 140

Cys Lys Leu Asp Ala Asp Asn Lys Val Val Cys Ser Cys Thr Thr Gly
145                 150                 155                 160

Tyr Gln Leu Ala Glu Asp Gln Lys Ser Cys Glu Pro Ala Val Pro Phe
                165                 170                 175

Pro Cys Gly Arg Val Ser Val Pro His Ile Ser Thr Thr His Thr Arg
            180                 185                 190

Ala Glu Thr Leu Phe Leu Asn Met Asp Tyr Glu Asn Ser Thr Thr Asp
            195                 200                 205

Tyr Glu Asn Ser Ala Glu Ala Lys Asn Val Asp Asn Val Thr Gln
    210                 215                 220

Pro Leu Asn Asp Leu Thr Arg Ile Val Gly Gly Lys Thr Ala Lys Pro
225                 230                 235                 240

Gly Gln Phe Pro Trp Gln Val Leu Leu Lys Gly Lys Ile Asp Ala Phe
                245                 250                 255

Cys Gly Gly Ser Ile Ile Asn Glu Lys Trp Val Val Thr Ala Ala His
            260                 265                 270

Cys Ile Asn Pro Asp Val Glu Ile Thr Val Val Ala Gly Glu His Asn
            275                 280                 285

Thr Glu Glu Thr Glu His Thr Glu Gln Lys Arg Asn Val Ile Arg Thr
            290                 295                 300
```

Ile Leu His His Ser Tyr Asn Ala Ser Val Asn Lys Tyr Ser His Asp
305                 310                 315                 320

Ile Ala Leu Leu Glu Leu Asp Glu Pro Leu Thr Leu Asn Ser Tyr Val
            325                 330                 335

Thr Pro Ile Cys Val Ala Asp Arg Glu Tyr Thr Asn Thr Phe Leu Lys
        340                 345                 350

Phe Gly Tyr Gly Tyr Val Ser Gly Trp Gly Lys Val Phe Asn Lys Gly
    355                 360                 365

Arg Pro Ala Thr Ile Leu Gln Tyr Leu Lys Val Pro Leu Val Asp Arg
370                 375                 380

Ala Thr Cys Leu Arg Ser Thr Lys Phe Thr Ile Tyr Asn Asn Met Phe
385                 390                 395                 400

Cys Ala Gly Phe His Glu Gly Gly Lys Asp Ser Cys Gln Gly Asp Ser
            405                 410                 415

Gly Gly Pro His Val Thr Glu Val Glu Gly Ile Asn Phe Leu Thr Gly
        420                 425                 430

Ile Ile Ser Trp Gly Glu Glu Cys Ala Met Lys Gly Lys Tyr Gly Ile
    435                 440                 445

Tyr Thr Lys Val Ser Arg Tyr Val Asn Trp Ile Lys Glu Lys Thr Lys
450                 455                 460

Leu Thr
465

<210> SEQ ID NO 31
<211> LENGTH: 77
<212> TYPE: PRT
<213> ORGANISM: Artificial Sequence
<220> FEATURE:
<223> OTHER INFORMATION: constructed sequence

<400> SEQUENCE: 31

Met Arg Cys Leu Asn Met Ile Met Ala Glu Pro Pro Gly Leu Ile Thr
1               5                   10                  15

Ile Cys Leu Leu Gly Tyr Leu Leu Gly Ala Asp Cys Thr Val Phe Leu
            20                  25                  30

Asp His Glu Asp Ala Thr Lys Val Leu Ser Arg Pro Lys Arg His Ala
        35                  40                  45

Glu Gly Thr Phe Thr Ser Asp Val Ser Ser Tyr Leu Glu Gly Gln Ala
    50                  55                  60

Ala Lys Glu Phe Ile Ala Trp Leu Val Lys Gly Arg Gly
65                  70                  75

<210> SEQ ID NO 32
<211> LENGTH: 452
<212> TYPE: PRT
<213> ORGANISM: Canis familiaris

<400> SEQUENCE: 32

Met Ala Glu Ala Ser Gly Leu Val Thr Val Cys Leu Leu Gly Tyr Leu
1               5                   10                  15

Leu Ser Ala Glu Cys Ala Val Phe Leu Asp Arg Glu Asn Ala Thr Lys
            20                  25                  30

Ile Leu Ser Arg Pro Lys Arg Tyr Asn Ser Gly Lys Leu Glu Glu Phe
        35                  40                  45

Val Arg Gly Asn Leu Glu Arg Glu Cys Ile Glu Glu Lys Cys Ser Phe
    50                  55                  60

```
Glu Glu Ala Arg Glu Val Phe Glu Asn Thr Lys Thr Thr Glu Phe
 65                  70                  75                  80

Trp Lys Gln Tyr Val Asp Gly Asp Gln Cys Glu Ser Asn Pro Cys Leu
                 85                  90                  95

Asn Asp Gly Val Cys Lys Asp Ile Asn Ser Tyr Glu Cys Trp Cys
                100                 105                 110

Arg Ala Gly Phe Glu Gly Lys Asn Cys Glu Leu Asp Val Thr Cys Asn
                115                 120                 125

Ile Lys Asn Gly Arg Cys Lys Gln Phe Cys Lys Leu Gly Pro Asp Asn
130                 135                 140

Lys Val Val Cys Ser Cys Thr Thr Gly Tyr Gln Leu Ala Glu Asp Gln
145                 150                 155                 160

Arg Ser Cys Glu Pro Ala Val Pro Phe Pro Cys Gly Arg Val Ser Val
                165                 170                 175

Pro His Ile Ser Met Thr Arg Thr Arg Ala Glu Thr Leu Phe Ser Asn
                180                 185                 190

Met Asp Tyr Glu Asn Ser Thr Glu Val Glu Lys Ile Leu Asp Asn Val
                195                 200                 205

Thr Gln Pro Leu Asn Asp Phe Thr Arg Val Val Gly Gly Lys Asp Ala
210                 215                 220

Lys Pro Gly Gln Phe Pro Trp Gln Val Leu Leu Asn Gly Lys Val Asp
225                 230                 235                 240

Ala Phe Cys Gly Gly Ser Ile Ile Asn Glu Lys Trp Val Val Thr Ala
                245                 250                 255

Ala His Cys Ile Glu Pro Asp Val Lys Ile Thr Ile Val Ala Gly Glu
                260                 265                 270

His Asn Thr Glu Lys Arg Glu His Thr Glu Gln Lys Arg Asn Val Ile
                275                 280                 285

Arg Thr Ile Leu His His Ser Tyr Asn Ala Thr Ile Asn Lys Tyr Asn
290                 295                 300

His Asp Ile Ala Leu Leu Glu Leu Asp Glu Pro Leu Thr Leu Asn Ser
305                 310                 315                 320

Tyr Val Thr Pro Ile Cys Ile Ala Asp Arg Glu Tyr Ser Asn Ile Phe
                325                 330                 335

Leu Lys Phe Gly Ser Gly Tyr Val Ser Gly Trp Gly Arg Val Phe Asn
                340                 345                 350

Lys Gly Arg Ser Ala Ser Ile Leu Gln Tyr Leu Lys Val Pro Leu Val
                355                 360                 365

Asp Arg Ala Thr Cys Leu Arg Ser Thr Lys Phe Thr Ile Tyr Asn Asn
370                 375                 380

Met Phe Cys Ala Gly Phe His Glu Gly Gly Lys Asp Ser Cys Gln Gly
385                 390                 395                 400

Asp Ser Gly Gly Pro His Val Thr Glu Val Glu Gly Ile Ser Phe Leu
                405                 410                 415

Thr Gly Ile Ile Ser Trp Gly Glu Glu Cys Ala Met Lys Gly Lys Tyr
                420                 425                 430

Gly Ile Tyr Thr Lys Val Ser Arg Tyr Val Asn Trp Ile Lys Glu Lys
                435                 440                 445

Thr Lys Leu Thr
    450

<210> SEQ ID NO 33
<211> LENGTH: 70
<212> TYPE: PRT
```

-continued

<213> ORGANISM: Artificial Sequence
<220> FEATURE:
<223> OTHER INFORMATION: constructed sequence

<400> SEQUENCE: 33

Met Ala Glu Ala Ser Gly Leu Val Thr Val Cys Leu Leu Gly Tyr Leu
1               5                   10                  15

Leu Ser Ala Glu Cys Ala Val Phe Leu Asp Arg Glu Asn Ala Thr Lys
            20                  25                  30

Ile Leu Ser Arg Pro Lys Arg His Ala Glu Gly Thr Phe Thr Ser Asp
        35                  40                  45

Val Ser Ser Tyr Leu Glu Gly Gln Ala Ala Lys Glu Phe Ile Ala Trp
    50                  55                  60

Leu Val Lys Gly Arg Gly
65                  70

<210> SEQ ID NO 34
<211> LENGTH: 461
<212> TYPE: PRT
<213> ORGANISM: Homo sapiens

<400> SEQUENCE: 34

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

```
Val Lys Ile Thr Val Val Ala Gly Glu His Asn Ile Glu Glu Thr Glu
        275                 280                 285

His Thr Glu Gln Lys Arg Asn Val Ile Arg Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
    450                 455                 460

<210> SEQ ID NO 35
<211> LENGTH: 77
<212> TYPE: PRT
<213> ORGANISM: Artificial Sequence
<220> FEATURE:
<223> OTHER INFORMATION: constructed sequence

<400> SEQUENCE: 35

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg His Ala
            35                  40                  45

Glu Gly Thr Phe Thr Ser Asp Val Ser Ser Tyr Leu Glu Gly Gln Ala
        50                  55                  60

Ala Lys Glu Phe Ile Ala Trp Leu Val Lys Gly Arg Gly
65                  70                  75

<210> SEQ ID NO 36
<211> LENGTH: 670
<212> TYPE: PRT
<213> ORGANISM: Felis catus

<400> SEQUENCE: 36

Gly Arg Cys Gly Ala Leu Leu Ala Cys Leu Val Leu Val Leu Pro Val
1               5                   10                  15

Ser Glu Ala Asn Phe Leu Ser Lys Gln His Ala Ser Gln Val Leu Ile
                20                  25                  30

Arg Lys Arg Arg Ala Asn Ser Met Phe Glu Glu Thr Lys Lys Gly Asn
            35                  40                  45
```

```
Leu Glu Arg Glu Cys Ile Glu Leu Cys Asn Lys Glu Ala Arg
    50              55                  60

Glu Ile Phe Glu Asn Asn Pro Glu Thr Asp Tyr Phe Tyr Pro Lys Tyr
65              70                  75                  80

Leu Asp Cys Leu Gly Ser Phe Arg Ala Gly Leu Phe Thr Ala Ala Arg
                85                  90                  95

Gln Ser Thr Asp Ala Tyr Pro Asp Leu Arg Ser Cys Val Thr Ala Ile
            100                 105                 110

Pro Asp Gln Cys Ser Pro Leu Pro Cys Asn Glu Asp Gly Tyr Met Ser
        115                 120                 125

Cys Lys Asp Gly Gln Ala Thr Phe Thr Cys Val Cys Lys Ser Gly Trp
130                 135                 140

Gln Gly Asp Lys Cys Glu Tyr Asp Ile Asn Glu Cys Lys Asp Pro Ser
145                 150                 155                 160

Asn Val Asn Gly Gly Cys Ser Gln Ile Cys Asp Asn Thr Pro Gly Ser
                165                 170                 175

Tyr His Cys Ser Cys Lys Ser Gly Phe Val Met Leu Ser Asn Lys Lys
            180                 185                 190

Asp Cys Lys Asp Val Asp Glu Cys Ser Met Lys Pro Asp Ile Cys Gly
        195                 200                 205

Thr Ala Val Cys Lys Asn Ile Pro Gly Asp Phe Glu Cys Glu Cys Ala
210                 215                 220

Glu Gly Tyr Arg Tyr Asn Pro Thr Leu Lys Ser Cys Glu Asp Val Asp
225                 230                 235                 240

Glu Cys Ser Glu Asn Met Cys Ala Gln Leu Cys Val Asn Tyr Pro Gly
                245                 250                 255

Gly Tyr Tyr Cys Tyr Cys Asp Gly Lys Lys Gly Phe Lys Leu Ala Gln
            260                 265                 270

Asp His Arg Ser Cys Glu Ala Val Pro Val Cys Leu Pro Leu Asn Leu
        275                 280                 285

Asp Lys Asn Tyr Glu Leu Leu Tyr Leu Ala Glu Gln Phe Val Gly Val
290                 295                 300

Val Leu Tyr Leu Lys Phe Arg Leu Pro Glu Ile Thr Arg Phe Ser Ala
305                 310                 315                 320

Glu Phe Asp Phe Arg Thr Tyr Asp Ser Glu Gly Val Ile Leu Tyr Ala
                325                 330                 335

Glu Ser Leu Asp His Ser Cys Trp Phe Leu Ile Ala Leu Arg Asp Gly
            340                 345                 350

Lys Ile Glu Ile Gln Phe Lys Asn Glu Tyr Ala Thr Lys Ile Thr Thr
        355                 360                 365

Gly Gly Lys Val Ile Asn Asn Gly Leu Trp Asn Thr Val Ser Val Glu
370                 375                 380

Glu Leu Glu Tyr Ser Ile Ser Val Lys Ile Ala Lys Glu Ala Val Met
385                 390                 395                 400

Asn Ile Asn Lys Pro Arg Ser Leu Phe Lys Pro Ala Asn Gly Phe Leu
                405                 410                 415

Glu Thr Lys Val Tyr Phe Ala Gly Leu Pro Arg Lys Gly Glu Asn Val
            420                 425                 430

Leu Ile Lys Pro Ile Asn Pro Arg Leu Asp Gly Cys Ile Arg Gly Trp
        435                 440                 445

Asn Leu Met Asn Gln Gly Ala Ser Gly Val Lys Glu Ile Ile Gln Glu
450                 455                 460

Lys Gln Asn Lys His Cys Leu Val Thr Val Glu Lys Gly Ser Tyr Tyr
```

```
                        465                 470                 475                 480

Pro Gly Ser Gly Val Ala Leu Phe Ser Ile Asp Tyr Asn Asn Ile Ser
                            485                 490                 495

Asn Ala Glu Gly Trp Gln Val Asn Val Ser Leu Asn Ile Arg Pro Ser
                        500                 505                 510

Ala Gly Thr Gly Val Met Phe Ala Leu Val Ser Gly Tyr Thr Val Pro
                    515                 520                 525

Phe Ala Leu Ser Leu Val Asp Ser Ala Ser Glu Lys Leu Gln Asp Ile
                530                 535                 540

Leu Val Ser Val Glu Asn Met Val Val Ser Arg Val Glu Ala Ile Ser
            545                 550                 555                 560

Leu Cys Ser Asn Glu Gln Phe His Leu Glu Val Arg Val Asn Arg Thr
                            565                 570                 575

Ser Leu Glu Leu Leu Thr Pro Leu Lys Lys Asp Ile Ile Tyr Ser Glu
                        580                 585                 590

Asp Leu Gln Ser Gln Leu Ala Ile Leu Asp Ile Ala Met Lys Glu Arg
                    595                 600                 605

Val Ser Thr Tyr Leu Gly Gly Leu Pro Asp Ile Pro Phe Ser Ala Thr
                610                 615                 620

Pro Val Asn Ala Phe Tyr Asn Gly Cys Met Glu Met Ser Ile Asn Gly
            625                 630                 635                 640

Val Gln Leu Asp Leu Asp Glu Ala Ile Ser Lys His Asn Asp Ile Arg
                            645                 650                 655

Ala His Ser Cys Pro Ser Val Leu Lys Lys Thr Lys Asn Ser
                        660                 665                 670

<210> SEQ ID NO 37
<211> LENGTH: 67
<212> TYPE: PRT
<213> ORGANISM: Artificial Sequence
<220> FEATURE:
<223> OTHER INFORMATION: constructed sequence

<400> SEQUENCE: 37

Gly Arg Cys Gly Ala Leu Leu Ala Cys Leu Val Leu Val Leu Pro Val
1               5                   10                  15

Ser Glu Ala Asn Phe Leu Ser Lys Gln His Ala Ser Gln Val Leu Ile
            20                  25                  30

Arg Lys Arg Arg His Ala Glu Gly Thr Phe Thr Ser Asp Val Ser Ser
        35                  40                  45

Tyr Leu Glu Gly Gln Ala Ala Lys Glu Phe Ile Ala Trp Leu Val Lys
    50                  55                  60

Gly Arg Gly
65

<210> SEQ ID NO 38
<211> LENGTH: 1077
<212> TYPE: PRT
<213> ORGANISM: Canis familiaris

<400> SEQUENCE: 38

Met Arg Leu Leu Ala Gly Arg Cys Gly Ala Leu Leu Ala Cys Leu Val
1               5                   10                  15

Leu Val Leu Pro Val Ser Glu Ala Asn Phe Leu Ser Lys Glu His Ala
            20                  25                  30

Ser Gln Val Leu Val Arg Lys Arg Arg Ala Asn Ser Met Phe Glu Glu
        35                  40                  45
```

-continued

```
Thr Lys Lys Gly Asn Leu Glu Arg Glu Cys Ile Glu Glu Leu Cys Asn
 50                  55                  60
Lys Glu Glu Ala Arg Glu Ile Phe Glu Asn Asp Pro Glu Thr Asp Tyr
 65                  70                  75                  80
Phe Tyr Pro Lys Tyr Leu Gly Cys Leu Gly Ser Phe Arg Ala Gly Leu
                 85                  90                  95
Phe Thr Ala Ala Arg Leu Ser Thr Asp Ala Tyr Pro Asp Leu Arg Ser
                100                 105                 110
Cys Val Thr Ala Ile Pro Asp Gln Cys Ser Pro Leu Pro Cys Asn Glu
            115                 120                 125
Asp Gly Tyr Lys Thr Cys Arg Asp Gly Gln Ala Thr Phe Thr Cys Ile
        130                 135                 140
Cys Lys Pro Gly Trp Gln Gly Asp Arg Cys Glu Tyr Asp Ile Asn Glu
145                 150                 155                 160
Cys Lys Asp Pro Ser Asn Ile Asn Gly Gly Cys Ser Gln Met Cys Asp
                165                 170                 175
Asn Thr Pro Gly Ser Tyr His Cys Ser Cys Lys Ser Gly Phe Val Met
                180                 185                 190
Leu Leu Asn Lys Lys Asp Cys Lys Asp Val Asp Glu Cys Ser Ile Met
            195                 200                 205
Pro Asp Ile Cys Gly Ala Ala Val Cys Lys Asn Ile Pro Gly Asp Tyr
        210                 215                 220
Glu Cys Glu Cys Ala Glu Gly Tyr Arg Tyr Asn Pro Ala Leu Lys Ser
225                 230                 235                 240
Cys Glu Asp Val Asp Glu Cys Ser Glu Asn Leu Cys Ala Gln Leu Cys
                245                 250                 255
Val Asn Tyr Pro Gly Gly Tyr Ser Cys Tyr Cys Asp Gly Arg Lys Gly
                260                 265                 270
Phe Lys Leu Ala Gln Asp His Lys Ser Cys Glu Ala Val Pro Val Cys
            275                 280                 285
Leu Pro Leu Asn Leu Asp Lys Asn Tyr Glu Leu Leu Tyr Leu Ala Glu
        290                 295                 300
Gln Phe Val Gly Val Leu Tyr Leu Lys Phe Arg Leu Pro Glu Ile
305                 310                 315                 320
Thr Arg Phe Ser Ala Glu Phe Asp Phe Arg Thr Tyr Asp Ser Glu Gly
                325                 330                 335
Val Ile Leu Tyr Ala Glu Ser Leu Asp Arg Ser Ala Trp Phe Leu Ile
                340                 345                 350
Ala Leu Arg Asp Gly Lys Ile Glu Ile Gln Phe Lys Asn Glu Phe Thr
            355                 360                 365
Thr Lys Ile Thr Thr Gly Gly Lys Ala Ile Asn Asn Gly Leu Trp Asn
        370                 375                 380
Thr Val Ser Val Glu Glu Leu Glu Tyr Ser Ile Ser Ile Lys Ile Ala
385                 390                 395                 400
Lys Glu Ala Val Met Asn Ile Asn Lys Pro Gly Arg Leu Phe Lys Pro
                405                 410                 415
Ser Asn Gly Phe Leu Glu Thr Lys Val Tyr Phe Ala Gly Leu Pro Arg
                420                 425                 430
Lys Val Glu Asn Val Leu Ile Arg Pro Ile Asn Pro Arg Leu Asp Gly
            435                 440                 445
Cys Ile Arg Gly Trp Asn Leu Met Asn Gln Gly Ala Ser Gly Val Lys
        450                 455                 460
```

```
Glu Ile Ile Gln Glu Lys Gln Asn Lys His Cys Leu Val Thr Val Glu
465                 470                 475                 480

Lys Gly Ser Tyr Tyr Pro Gly Ser Gly Val Ala Val Phe Gly Ile Asp
            485                 490                 495

Tyr Lys Gly Gln Tyr Leu Arg Leu Arg Asp Cys Phe Val Pro Pro Pro
        500                 505                 510

Pro Ala Ala Phe Pro Gly Phe Leu Arg Thr Ala Arg Leu Trp Phe Gly
    515                 520                 525

Gly Gln Arg Pro Gly Arg Ala Ala Glu Arg Pro Ser Leu Gly Gly
    530                 535                 540

Arg Gly Val Ser Ala Gly Gly Glu Ser Arg Gln Leu Gly Gly Cys Glu
545                 550                 555                 560

Leu Phe Ile Ala Pro Ser Gln Pro Ala Gly Gly Gly Gly
                565                 570                 575

Gly Gly Gly Gly Asp Leu Met Leu Arg Thr Gln Asp Val Phe Leu Leu
            580                 585                 590

Leu Leu Gly Lys Gly Gln Leu Val Gly Trp Leu Val Leu Pro Arg Phe
    595                 600                 605

Pro Ala Leu Ser Met Tyr Arg Val Ser Ala Gly Val Pro Arg Ala Thr
    610                 615                 620

Gly Phe Val Ala Phe Arg Pro Ser Lys Ala Leu Leu Pro Arg Glu
625                 630                 635                 640

Gly Thr Arg Arg His Gly Ser Asn Gly Leu Cys Thr Ser Cys Gly Leu
                645                 650                 655

Arg Ser Ser Pro Gln Ala Ala Gly Arg Gly Gly Tyr Thr Arg Gly Pro
        660                 665                 670

Arg Gly Gly Ala Gly Gly Ile Lys Leu Leu Trp Lys Pro Ile Asn Ser
    675                 680                 685

Ser Ile Cys Arg Val Thr Ser Val Glu Asn Lys Gly Val Pro Glu Ala
    690                 695                 700

Arg Arg Val Cys Thr Pro Gly Gly Gly Thr Val Ser Pro Val Ala Arg
705                 710                 715                 720

Lys Arg Asp Glu Lys Gln Gly Arg Gly Glu Lys Asp Cys Asp Glu Ala
            725                 730                 735

Gln Arg Pro Arg Lys Glu Ser Ala Ala Gly Ala Ala Gly Trp Ala
        740                 745                 750

Cys Gly Glu Met Pro Val Gly Arg Ala Arg Ala Ala Glu Pro Asn Ala
            755                 760                 765

Pro Ser Glu Ala Pro Ser Glu Ala Glu Ala Leu Arg Arg Val
    770                 775                 780

Trp Ala Pro Pro Arg Arg Gly Pro Gly Ala Ala Pro Ala Pro Arg Leu
785                 790                 795                 800

Ala Gly Gly Gly Arg Gly Trp Ala Glu Ala Pro Gly Lys Pro Cys Glu
            805                 810                 815

His Gln Arg Gly Lys Pro Leu Val Ser Ala Pro Val Gln Arg Pro Arg
            820                 825                 830

Arg Arg Ala Gly Pro Ala Pro Ser Arg Ala Ser Arg Arg Pro Val Pro
        835                 840                 845

Arg Arg Ser Gln Arg Ser Arg Ser Gln Glu Val Thr Ala Gly His
        850                 855                 860

Ser Arg His Ser Arg His Ser Gly Leu Gln Gln Val Thr Ala Val Thr
865                 870                 875                 880

Ala Val Thr Ala Gly His Ser Arg Ser Gln Pro Ala Gln Arg Val Ala
```

```
                885                 890                 895
Ala Gly His Ser Gly Leu Gln Gln Val Ala Thr Gly His Ser Gly His
                900                 905                 910

Cys Ala Gln Gln Val Ala Ala Gly Cys Asn Arg Ser Gln Arg Val Thr
            915                 920                 925

Ala Gly His Ser Ser His Ser Gly Ser Gln Gln Val Thr Ala Ser His
        930                 935                 940

Ser Gly Ser Gln Gln Asp Ile Leu Val Ser Val Glu Asn Ile Val Ile
945                 950                 955                 960

Ser Arg Ile Glu Ala Val Asn Leu Cys Ser Asn Gln Gln Val His Leu
                965                 970                 975

Glu Leu Lys Val Asn Arg Asn Asn Leu Glu Leu Ser Thr Pro Val Lys
            980                 985                 990

Lys Asp Thr Ile Ser Ser Glu Asp Leu Pro Gln Gln Phe Ala Ser Leu
        995                1000                1005

Asp Lys Ala Met Lys Gly Thr Val Thr Thr Tyr Leu Gly Gly Leu
    1010                1015                1020

Pro Asp Ile Pro Phe Gly Ala Thr Pro Val Asn Val Phe Tyr Asn
    1025                1030                1035

Gly Cys Met Glu Val Asn Ile Asn Gly Val Gln Leu Asp Leu Asp
    1040                1045                1050

Glu Ala Ile Ser Lys His Asn Asp Ile Arg Ala His Ser Cys Pro
    1055                1060                1065

Ser Val Leu Lys Ser Thr Lys Asn Ser
    1070                1075

<210> SEQ ID NO 39
<211> LENGTH: 72
<212> TYPE: PRT
<213> ORGANISM: Artificial Sequence
<220> FEATURE:
<223> OTHER INFORMATION: constructed sequence

<400> SEQUENCE: 39

Met Arg Leu Leu Ala Gly Arg Cys Gly Ala Leu Leu Ala Cys Leu Val
1               5                   10                  15

Leu Val Leu Pro Val Ser Glu Ala Asn Phe Leu Ser Lys Glu His Ala
            20                  25                  30

Ser Gln Val Leu Val Arg Lys Arg Arg His Ala Glu Gly Thr Phe Thr
        35                  40                  45

Ser Asp Val Ser Ser Tyr Leu Glu Gly Gln Ala Ala Lys Glu Phe Ile
    50                  55                  60

Ala Trp Leu Val Lys Gly Arg Gly
65                  70

<210> SEQ ID NO 40
<211> LENGTH: 676
<212> TYPE: PRT
<213> ORGANISM: Homo sapiens

<400> SEQUENCE: 40

Met Arg Val Leu Gly Gly Arg Cys Gly Ala Leu Leu Ala Cys Leu Leu
1               5                   10                  15

Leu Val Leu Pro Val Ser Glu Ala Asn Phe Leu Ser Lys Gln Gln Ala
            20                  25                  30

Ser Gln Val Leu Val Arg Lys Arg Arg Ala Asn Ser Leu Leu Glu Glu
        35                  40                  45
```

-continued

Thr Lys Gln Gly Asn Leu Glu Arg Glu Cys Ile Glu Glu Leu Cys Asn
 50                  55                  60

Lys Glu Glu Ala Arg Glu Val Phe Glu Asn Asp Pro Glu Thr Asp Tyr
 65                  70                  75                  80

Phe Tyr Pro Lys Tyr Leu Val Cys Leu Arg Ser Phe Gln Thr Gly Leu
                 85                  90                  95

Phe Thr Ala Ala Arg Gln Ser Thr Asn Ala Tyr Pro Asp Leu Arg Ser
             100                 105                 110

Cys Val Asn Ala Ile Pro Asp Gln Cys Ser Pro Leu Pro Cys Asn Glu
         115                 120                 125

Asp Gly Tyr Met Ser Cys Lys Asp Gly Lys Ala Ser Phe Thr Cys Thr
     130                 135                 140

Cys Lys Pro Gly Trp Gln Gly Glu Lys Cys Glu Phe Asp Ile Asn Glu
145                 150                 155                 160

Cys Lys Asp Pro Ser Asn Ile Asn Gly Gly Cys Ser Gln Ile Cys Asp
                165                 170                 175

Asn Thr Pro Gly Ser Tyr His Cys Ser Cys Lys Asn Gly Phe Val Met
            180                 185                 190

Leu Ser Asn Lys Lys Asp Cys Lys Asp Val Asp Glu Cys Ser Leu Lys
        195                 200                 205

Pro Ser Ile Cys Gly Thr Ala Val Cys Lys Asn Ile Pro Gly Asp Phe
    210                 215                 220

Glu Cys Glu Cys Pro Glu Gly Tyr Arg Tyr Asn Leu Lys Ser Lys Ser
225                 230                 235                 240

Cys Glu Asp Ile Asp Glu Cys Ser Glu Asn Met Cys Ala Gln Leu Cys
                245                 250                 255

Val Asn Tyr Pro Gly Gly Tyr Thr Cys Tyr Cys Asp Gly Lys Lys Gly
            260                 265                 270

Phe Lys Leu Ala Gln Asp Gln Lys Ser Cys Glu Val Val Ser Val Cys
        275                 280                 285

Leu Pro Leu Asn Leu Asp Thr Lys Tyr Glu Leu Leu Tyr Leu Ala Glu
    290                 295                 300

Gln Phe Ala Gly Val Val Leu Tyr Leu Lys Phe Arg Leu Pro Glu Ile
305                 310                 315                 320

Ser Arg Phe Ser Ala Glu Phe Asp Phe Arg Thr Tyr Asp Ser Glu Gly
                325                 330                 335

Val Ile Leu Tyr Ala Glu Ser Ile Asp His Ser Ala Trp Leu Leu Ile
            340                 345                 350

Ala Leu Arg Gly Gly Lys Ile Glu Val Gln Leu Lys Asn Glu His Thr
        355                 360                 365

Ser Lys Ile Thr Thr Gly Gly Asp Val Ile Asn Asn Gly Leu Trp Asn
    370                 375                 380

Met Val Ser Val Glu Glu Leu Glu His Ser Ile Ser Ile Lys Ile Ala
385                 390                 395                 400

Lys Glu Ala Val Met Asp Ile Asn Lys Pro Gly Pro Leu Phe Lys Pro
                405                 410                 415

Glu Asn Gly Leu Leu Glu Thr Lys Val Tyr Phe Ala Gly Phe Pro Arg
            420                 425                 430

Lys Val Glu Ser Glu Leu Ile Lys Pro Ile Asn Pro Arg Leu Asp Gly
        435                 440                 445

Cys Ile Arg Ser Trp Asn Leu Met Lys Gln Gly Ala Ser Gly Ile Lys
    450                 455                 460

-continued

```
Glu Ile Ile Gln Glu Lys Gln Asn Lys His Cys Leu Val Thr Val Glu
465                 470                 475                 480

Lys Gly Ser Tyr Tyr Pro Gly Ser Gly Ile Ala Gln Phe His Ile Asp
            485                 490                 495

Tyr Asn Asn Val Ser Ser Ala Glu Gly Trp His Val Asn Val Thr Leu
        500                 505                 510

Asn Ile Arg Pro Ser Thr Gly Thr Gly Val Met Leu Ala Leu Val Ser
    515                 520                 525

Gly Asn Asn Thr Val Pro Phe Ala Val Ser Leu Val Asp Ser Thr Ser
530                 535                 540

Glu Lys Ser Gln Asp Ile Leu Leu Ser Val Glu Asn Thr Val Ile Tyr
545                 550                 555                 560

Arg Ile Gln Ala Leu Ser Leu Cys Ser Asp Gln Gln Ser His Leu Glu
                565                 570                 575

Phe Arg Val Asn Arg Asn Asn Leu Glu Leu Ser Thr Pro Leu Lys Ile
            580                 585                 590

Glu Thr Ile Ser His Glu Asp Leu Gln Arg Gln Leu Ala Val Leu Asp
        595                 600                 605

Lys Ala Met Lys Ala Lys Val Ala Thr Tyr Leu Gly Gly Leu Pro Asp
610                 615                 620

Val Pro Phe Ser Ala Thr Pro Val Asn Ala Phe Tyr Asn Gly Cys Met
625                 630                 635                 640

Glu Val Asn Ile Asn Gly Val Gln Leu Asp Leu Asp Glu Ala Ile Ser
                645                 650                 655

Lys His Asn Asp Ile Arg Ala His Ser Cys Pro Ser Val Trp Lys Lys
            660                 665                 670

Thr Lys Asn Ser
        675

<210> SEQ ID NO 41
<211> LENGTH: 72
<212> TYPE: PRT
<213> ORGANISM: Artificial Sequence
<220> FEATURE:
<223> OTHER INFORMATION: constructed sequence

<400> SEQUENCE: 41

Met Arg Val Leu Gly Gly Arg Cys Gly Ala Leu Leu Ala Cys Leu Leu
1               5                   10                  15

Leu Val Leu Pro Val Ser Glu Ala Asn Phe Leu Ser Lys Gln Gln Ala
            20                  25                  30

Ser Gln Val Leu Val Arg Lys Arg Arg His Ala Glu Gly Thr Phe Thr
        35                  40                  45

Ser Asp Val Ser Ser Tyr Leu Glu Gly Gln Ala Ala Lys Glu Phe Ile
    50                  55                  60

Ala Trp Leu Val Lys Gly Arg Gly
65                  70

<210> SEQ ID NO 42
<211> LENGTH: 422
<212> TYPE: PRT
<213> ORGANISM: Homo sapiens

<400> SEQUENCE: 42

Met Ala Gly Cys Val Pro Leu Leu Gln Gly Leu Val Leu Val Leu Ala
1               5                   10                  15

Leu His Arg Val Glu Pro Ser Ala Thr Ser Leu Lys Glu Arg His Gly
```

```
                20                  25                  30
Leu His Ser Asp Ser Ala Cys Thr Gly Val Gln Glu Ser Leu Phe Leu
            35                  40                  45
Pro Ala Ser Lys Ala Asn Asp Val Leu Val Arg Trp Lys Arg Ala Gly
 50                  55                  60
Ser Tyr Leu Leu Glu Glu Leu Phe Glu Gly Asn Leu Glu Lys Glu Cys
 65                  70                  75                  80
Tyr Glu Glu Ile Cys Val Tyr Glu Glu Ala Arg Glu Val Phe Glu Asn
                85                  90                  95
Glu Val Val Thr Asp Glu Phe Trp Arg Arg Tyr Lys Gly Gly Ser Pro
            100                 105                 110
Cys Ile Ser Gln Pro Cys Leu His Asn Gly Ser Cys Gln Asp Ser Ile
            115                 120                 125
Trp Gly Tyr Thr Cys Thr Cys Ser Pro Gly Tyr Glu Gly Ser Asn Cys
            130                 135                 140
Glu Leu Ala Lys Asn Glu Cys His Pro Glu Arg Thr Asp Gly Cys Gln
145                 150                 155                 160
His Phe Cys Leu Pro Gly Gln Glu Ser Tyr Thr Cys Ser Cys Ala Gln
                165                 170                 175
Gly Tyr Arg Leu Gly Glu Asp His Lys Gln Cys Val Pro His Asp Gln
            180                 185                 190
Cys Ala Cys Gly Val Leu Thr Ser Glu Lys Arg Ala Pro Asp Leu Gln
            195                 200                 205
Asp Leu Pro Trp Gln Val Lys Leu Thr Asn Ser Glu Gly Lys Asp Phe
            210                 215                 220
Cys Gly Gly Val Ile Ile Arg Glu Asn Phe Val Leu Thr Thr Ala Lys
225                 230                 235                 240
Cys Ser Leu Leu His Arg Asn Ile Thr Val Lys Thr Tyr Phe Asn Arg
                245                 250                 255
Thr Ser Gln Asp Pro Leu Met Ile Lys Ile Thr His Val His Val His
            260                 265                 270
Met Arg Tyr Asp Ala Asp Ala Gly Glu Asn Asp Leu Ser Leu Leu Glu
            275                 280                 285
Leu Glu Trp Pro Ile Gln Cys Pro Gly Ala Gly Leu Pro Val Cys Thr
            290                 295                 300
Pro Glu Lys Asp Phe Ala Glu His Leu Leu Ile Pro Arg Thr Arg Gly
305                 310                 315                 320
Leu Leu Ser Gly Trp Ala Arg Asn Gly Thr Asp Leu Gly Asn Ser Leu
                325                 330                 335
Thr Thr Arg Pro Val Thr Leu Val Glu Gly Glu Cys Gly Gln Val
            340                 345                 350
Leu Asn Val Thr Val Thr Thr Arg Thr Tyr Cys Glu Arg Ser Ser Val
            355                 360                 365
Ala Ala Met His Trp Met Asp Gly Ser Val Val Thr Arg Glu His Arg
            370                 375                 380
Gly Ser Trp Phe Leu Thr Gly Val Leu Gly Ser Gln Pro Val Gly Gly
385                 390                 395                 400
Gln Ala His Met Val Leu Val Thr Lys Val Ser Arg Tyr Ser Leu Trp
                405                 410                 415
Phe Lys Gln Ile Met Asn
            420

<210> SEQ ID NO 43
```

```
<211> LENGTH: 93
<212> TYPE: PRT
<213> ORGANISM: Artificial Sequence
<220> FEATURE:
<223> OTHER INFORMATION: constructed sequence

<400> SEQUENCE: 43

Met Ala Gly Cys Val Pro Leu Leu Gln Gly Leu Val Leu Val Leu Ala
1               5                   10                  15

Leu His Arg Val Glu Pro Ser Ala Thr Ser Leu Lys Glu Arg His Gly
            20                  25                  30

Leu His Ser Asp Ser Ala Cys Thr Gly Val Gln Glu Ser Leu Phe Leu
        35                  40                  45

Pro Ala Ser Lys Ala Asn Asp Val Leu Val Arg Trp Lys Arg His Ala
    50                  55                  60

Glu Gly Thr Phe Thr Ser Asp Val Ser Ser Tyr Leu Glu Gly Gln Ala
65                  70                  75                  80

Ala Lys Glu Phe Ile Ala Trp Leu Val Lys Gly Arg Gly
                85                  90

<210> SEQ ID NO 44
<211> LENGTH: 411
<212> TYPE: PRT
<213> ORGANISM: Felis catus

<400> SEQUENCE: 44

Met Trp Gln Leu Ser Ser Leu Phe Leu Leu Val Thr Ile Trp Gly Thr
1               5                   10                  15

Ser Ala Thr Pro Ala Pro Pro Asp Ser Val Phe Ser Ser Arg Glu Leu
            20                  25                  30

Ser His Arg Val Leu Arg Ile Arg Lys Arg Ala Asn Thr Phe Leu Glu
        35                  40                  45

Glu Leu Arg Ala Gly Ser Leu Glu Arg Glu Cys Val Glu Glu Ile Cys
    50                  55                  60

Asp Leu Glu Glu Ala Gln Glu Ile Phe Gln Asn Val Asp Asp Thr Leu
65                  70                  75                  80

Ala Phe Trp Ala Lys Tyr Ile Asp Glu Asp Gln Cys Ala Ala Pro Pro
                85                  90                  95

Pro Asp His Pro Cys Asp Ser Pro Cys Cys Gly His Gly Asn Cys Ile
            100                 105                 110

Asp Gly Ile Ser Ala Phe Arg Cys Asp Cys Asp Pro Gly Trp Glu Gly
        115                 120                 125

Arg Phe Cys Leu Tyr Val Lys Phe Pro Cys Gly Arg Pro Gly Arg Arg
    130                 135                 140

Met Glu Lys Lys Arg Lys Thr Val Lys Arg Asp Thr Ser Gln Ala Asp
145                 150                 155                 160

Gln Ile Asp Pro Arg Leu Val Asn Gly Lys Leu Ser Gly Trp Gly Glu
                165                 170                 175

Ser Pro Trp Gln Val Ile Leu Leu Asp Ser Lys Lys Leu Ala Cys
            180                 185                 190

Gly Ala Val Leu Ile His Thr Ser Trp Val Leu Thr Ala Ala His Cys
        195                 200                 205

Met Glu Asp Ser Lys Lys Leu Met Val Arg Leu Gly Glu Tyr Asp Leu
    210                 215                 220

Arg Arg Arg Glu Lys Trp Glu Leu Asp Leu Asp Ile Lys Glu Val Leu
225                 230                 235                 240
```

```
Met His Pro Asn Tyr Ser Arg Ser Thr Ser Asp Asn Asp Ile Ala Leu
            245                 250                 255

Leu Arg Leu Ala Gln Pro Ala Ile Leu Ser Gln Thr Ile Val Pro Ile
        260                 265                 270

Cys Leu Pro Asp Ser Gly Leu Ala Glu Arg Glu Leu Thr Gln Ala Gly
        275                 280                 285

Gln Glu Thr Val Val Thr Gly Trp Gly His Arg Ser Glu Ala Lys Arg
        290                 295                 300

Asn Arg Thr Phe Val Leu Asn Phe Ile Lys Val Pro Val Val Pro Gln
305                 310                 315                 320

Asn Glu Cys Ile Asn Ala Met His Asn Met Ile Ser Glu Asn Met Leu
                325                 330                 335

Cys Ala Gly Ile Leu Gly Asp Ser Gln Asp Ala Cys Glu Gly Asp Ser
                340                 345                 350

Gly Gly Pro Met Val Ala Ser Phe Arg Gly Thr Ser Phe Leu Val Gly
            355                 360                 365

Leu Val Ser Trp Gly Glu Gly Cys Gly Arg Leu His Asn Tyr Gly Val
        370                 375                 380

Tyr Thr Lys Val Ser Arg Tyr Leu Asp Trp Ile His Ser His Ile Arg
385                 390                 395                 400

Ala Glu Glu Ala Ser Leu Glu Gly Gln Val Pro
                405                 410

<210> SEQ ID NO 45
<211> LENGTH: 73
<212> TYPE: PRT
<213> ORGANISM: Artificial Sequence
<220> FEATURE:
<223> OTHER INFORMATION: constructed sequence

<400> SEQUENCE: 45

Met Trp Gln Leu Ser Ser Leu Phe Leu Leu Val Thr Ile Trp Gly Thr
1               5                   10                  15

Ser Ala Thr Pro Ala Pro Pro Asp Ser Val Phe Ser Ser Arg Glu Leu
            20                  25                  30

Ser His Arg Val Leu Arg Ile Arg Lys Arg His Ala Glu Gly Thr Phe
        35                  40                  45

Thr Ser Asp Val Ser Ser Tyr Leu Glu Gly Gln Ala Ala Lys Glu Phe
    50                  55                  60

Ile Ala Trp Leu Val Lys Gly Arg Gly
65                  70

<210> SEQ ID NO 46
<211> LENGTH: 456
<212> TYPE: PRT
<213> ORGANISM: Canis familiaris

<400> SEQUENCE: 46

Met Trp Gln Leu Ala Ser Leu Ser Leu Leu Thr Ile Cys Gly Thr
1               5                   10                  15

Cys Ser Thr Ala Ala Pro Pro Gly Ser Val Phe Ser Ser Ser Glu Ser
            20                  25                  30

Ala His Gln Val Leu Arg Ile Arg Lys Arg Ala Asn Ser Phe Leu Glu
        35                  40                  45

Glu Ile Arg Ala Gly Ser Leu Glu Arg Glu Cys Met Glu Glu Ile Cys
    50                  55                  60

Asp Phe Glu Glu Ala Lys Glu Ile Phe Gln Asn Val Asp Asp Thr Leu
```

```
                65                  70                  75                  80
        Ala Tyr Trp Ser Lys Tyr Val Asp Gly Asp Gln Cys Ala Ala Leu Pro
                            85                  90                  95

Pro Glu His Ala Cys Asp Ser Pro Cys Cys Gly His Gly Ser Cys Ile
                           100                 105                 110

Asp Gly Ile Gly Ala Phe His Cys Asp Cys Gly Arg Gly Trp Glu Gly
                           115                 120                 125

Arg Phe Cys Gln His Glu Val Ser Tyr Ile Asn Cys Ser Leu Asp Asn
                           130                 135                 140

Gly Gly Cys Ser His Tyr Cys Leu Glu Glu Gly Arg His Cys
        145                 150                 155                 160

Ser Cys Ala Pro Gly Tyr Arg Leu Gly Asp His Leu Gln Cys Gln
                           165                 170                 175

Pro Ala Val Lys Phe Pro Cys Gly Arg Pro Gly Lys Gln Met Glu Lys
                           180                 185                 190

Lys Arg Lys His Leu Lys Arg Asp Thr Asn Gln Thr Asp Gln Ile Asp
                           195                 200                 205

Pro Arg Leu Val Asn Gly Lys Val Thr Arg Arg Gly Glu Ser Pro Trp
                           210                 215                 220

Gln Val Val Leu Leu Asp Ser Lys Lys Lys Leu Ala Cys Gly Ala Val
        225                 230                 235                 240

Leu Ile His Thr Ser Trp Val Leu Thr Ala Ala His Cys Met Glu Asp
                           245                 250                 255

Ser Lys Lys Leu Ile Val Arg Leu Gly Glu Tyr Asp Leu Arg Arg Trp
                           260                 265                 270

Glu Lys Gly Glu Met Asp Val Asp Ile Lys Glu Val Leu Ile His Pro
                           275                 280                 285

Asn Tyr Ser Lys Ser Thr Thr Asp Asn Asp Ile Ala Leu Leu His Leu
                           290                 295                 300

Ala Gln Pro Ala Ile Phe Ser Gln Thr Ile Val Pro Ile Cys Leu Pro
        305                 310                 315                 320

Asp Ser Gly Leu Ala Glu Arg Glu Leu Thr Gln Val Gly Gln Glu Thr
                           325                 330                 335

Val Val Thr Gly Trp Gly Tyr Arg Ser Glu Thr Lys Arg Asn Arg Thr
                           340                 345                 350

Phe Val Leu Asn Phe Ile Asn Ile Pro Val Ala Pro His Asn Glu Cys
                           355                 360                 365

Ile Gln Ala Met Tyr Asn Met Ile Ser Glu Asn Met Leu Cys Ala Gly
        370                 375                 380

Ile Leu Gly Asp Ser Arg Asp Ala Cys Glu Gly Asp Ser Gly Gly Pro
        385                 390                 395                 400

Met Val Thr Ser Phe Arg Gly Thr Trp Phe Leu Val Gly Leu Val Ser
                           405                 410                 415

Trp Gly Glu Gly Cys Gly Arg Leu His Asn Tyr Gly Ile Tyr Thr Lys
                           420                 425                 430

Val Ser Arg Tyr Leu Asp Trp Ile His Ser His Ile Arg Gly Glu Glu
                           435                 440                 445

Ala Ser Leu Glu Asn Gln Val Pro
                           450                 455

<210> SEQ ID NO 47
<211> LENGTH: 73
<212> TYPE: PRT
<213> ORGANISM: Artificial Sequence
```

```
<220> FEATURE:
<223> OTHER INFORMATION: constructed sequence

<400> SEQUENCE: 47

Met Trp Gln Leu Ala Ser Leu Ser Leu Leu Thr Ile Cys Gly Thr
1               5                   10                  15

Cys Ser Thr Ala Ala Pro Pro Gly Ser Val Phe Ser Ser Glu Ser
            20                  25                  30

Ala His Gln Val Leu Arg Ile Arg Lys Arg His Ala Glu Gly Thr Phe
        35                  40                  45

Thr Ser Asp Val Ser Ser Tyr Leu Glu Gly Gln Ala Ala Lys Glu Phe
    50                  55                  60

Ile Ala Trp Leu Val Lys Gly Arg Gly
65                  70

<210> SEQ ID NO 48
<211> LENGTH: 461
<212> TYPE: PRT
<213> ORGANISM: Homo sapiens

<400> SEQUENCE: 48

Met Trp Gln Leu Thr Ser Leu Leu Leu Phe Val Ala Thr Trp Gly Ile
1               5                   10                  15

Ser Gly Thr Pro Ala Pro Leu Asp Ser Val Phe Ser Ser Ser Glu Arg
            20                  25                  30

Ala His Gln Val Leu Arg Ile Arg Lys Arg Ala Asn Ser Phe Leu Glu
        35                  40                  45

Glu Leu Arg His Ser Ser Leu Glu Arg Glu Cys Ile Glu Glu Ile Cys
    50                  55                  60

Asp Phe Glu Glu Ala Lys Glu Ile Phe Gln Asn Val Asp Asp Thr Leu
65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
            100                 105                 110

Asp Gly Ile Gly Ser Phe Ser Cys Asp Cys Arg Ser Gly Trp Glu Gly
        115                 120                 125

Arg Phe Cys Gln Arg Glu Val Ser Phe Leu Asn Cys Ser Leu Asp Asn
130                 135                 140

Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
            180                 185                 190

Lys Arg Ser His Leu Lys Arg Asp Thr Glu Asp Gln Glu Asp Gln Val
        195                 200                 205

Asp Pro Arg Leu Ile Asp Gly Lys Met Thr Arg Arg Gly Asp Ser Pro
    210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Arg Leu Gly Glu Tyr Asp Leu Arg Arg
            260                 265                 270
```

```
Trp Glu Lys Trp Glu Leu Asp Leu Asp Ile Lys Glu Val Phe Val His
            275                 280                 285

Pro Asn Tyr Ser Lys Ser Thr Thr Asp Asn Asp Ile Ala Leu Leu His
        290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335

Thr Leu Val Thr Gly Trp Gly Tyr His Ser Ser Arg Glu Lys Glu Ala
                340                 345                 350

Lys Arg Asn Arg Thr Phe Val Leu Asn Phe Ile Lys Ile Pro Val Val
            355                 360                 365

Pro His Asn Glu Cys Ser Glu Val Met Ser Asn Met Val Ser Glu Asn
        370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                405                 410                 415

Val Gly Leu Val Ser Trp Gly Glu Gly Cys Gly Leu Leu His Asn Tyr
            420                 425                 430

Gly Val Tyr Thr Lys Val Ser Arg Tyr Leu Asp Trp Ile His Gly His
        435                 440                 445

Ile Arg Asp Lys Glu Ala Pro Gln Lys Ser Trp Ala Pro
    450                 455                 460

<210> SEQ ID NO 49
<211> LENGTH: 73
<212> TYPE: PRT
<213> ORGANISM: Artificial Sequence
<220> FEATURE:
<223> OTHER INFORMATION: constructed sequence

<400> SEQUENCE: 49

Met Trp Gln Leu Thr Ser Leu Leu Leu Phe Val Ala Thr Trp Gly Ile
1               5                   10                  15

Ser Gly Thr Pro Ala Pro Leu Asp Ser Val Phe Ser Ser Glu Arg
            20                  25                  30

Ala His Gln Val Leu Arg Ile Arg Lys Arg His Ala Glu Gly Thr Phe
        35                  40                  45

Thr Ser Asp Val Ser Ser Tyr Leu Glu Gly Gln Ala Ala Lys Glu Phe
    50                  55                  60

Ile Ala Trp Leu Val Lys Gly Arg Gly
65                  70

<210> SEQ ID NO 50
<211> LENGTH: 608
<212> TYPE: PRT
<213> ORGANISM: Felis catus

<400> SEQUENCE: 50

Met Lys Trp Val Thr Phe Ile Ser Leu Leu Leu Phe Ser Ser Ala
1               5                   10                  15

Tyr Ser Arg Gly Val Thr Arg Arg Glu Ala His Gln Ser Glu Ile Ala
            20                  25                  30

His Arg Phe Asn Asp Leu Gly Glu Glu His Phe Arg Gly Leu Val Leu
        35                  40                  45

Val Ala Phe Ser Gln Tyr Leu Gln Gln Cys Pro Phe Glu Asp His Val
```

```
            50                  55                  60
Lys Leu Val Asn Glu Val Thr Glu Phe Ala Lys Gly Cys Val Ala Asp
 65                  70                  75                  80

Gln Ser Ala Ala Asn Cys Glu Lys Ser Leu His Glu Leu Leu Gly Asp
                 85                  90                  95

Lys Leu Cys Thr Val Ala Ser Leu Arg Asp Lys Tyr Gly Glu Met Ala
            100                 105                 110

Asp Cys Cys Glu Lys Lys Glu Pro Glu Arg Asn Glu Cys Phe Leu Gln
        115                 120                 125

His Lys Asp Asp Asn Pro Gly Phe Gly Gln Leu Val Thr Pro Glu Ala
    130                 135                 140

Asp Ala Met Cys Thr Ala Phe His Glu Asn Glu Gln Arg Phe Leu Gly
145                 150                 155                 160

Lys Tyr Leu Tyr Glu Ile Ala Arg Arg His Pro Tyr Phe Tyr Ala Pro
                165                 170                 175

Glu Leu Leu Tyr Tyr Ala Glu Glu Tyr Lys Gly Val Phe Thr Glu Cys
            180                 185                 190

Cys Glu Ala Ala Asp Lys Ala Ala Cys Leu Thr Pro Lys Val Asp Ala
        195                 200                 205

Leu Arg Glu Lys Val Leu Ala Ser Ser Ala Lys Glu Arg Leu Lys Cys
210                 215                 220

Ala Ser Leu Gln Lys Phe Gly Glu Arg Ala Phe Lys Ala Trp Ser Val
225                 230                 235                 240

Ala Arg Leu Ser Gln Lys Phe Pro Lys Ala Glu Phe Ala Glu Ile Ser
                245                 250                 255

Lys Leu Val Thr Asp Leu Ala Lys Ile His Lys Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Thr Lys Leu Lys Glu Cys Cys Gly
    290                 295                 300

Lys Pro Val Leu Glu Lys Ser His Cys Ile Ser Glu Val Glu Arg Asp
305                 310                 315                 320

Glu Leu Pro Ala Asp Leu Pro Pro Leu Ala Val Asp Phe Val Glu Asp
                325                 330                 335

Lys Glu Val Cys Lys Asn Tyr Gln Glu Ala Lys Asp Val Phe Leu Gly
            340                 345                 350

Thr Phe Leu Tyr Glu Tyr Ser Arg Arg His Pro Glu Tyr Ser Val Ser
        355                 360                 365

Leu Leu Leu Arg Leu Ala Lys Glu Tyr Glu Ala Thr Leu Glu Lys Cys
    370                 375                 380

Cys Ala Thr Asp Asp Pro Pro Ala Cys Tyr Ala His Val Phe Asp Glu
385                 390                 395                 400

Phe Lys Pro Leu Val Glu Glu Pro His Asn Leu Val Lys Thr Asn Cys
                405                 410                 415

Glu Leu Phe Glu Lys Leu Gly Glu Tyr Gly Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Ser Leu Gly Lys Val Gly Ser Lys Cys Cys Thr His
    450                 455                 460

Pro Glu Ala Glu Arg Leu Ser Cys Ala Glu Asp Tyr Leu Ser Val Val
465                 470                 475                 480
```

```
Leu Asn Arg Leu Cys Val Leu His Glu Lys Thr Pro Val Ser Glu Arg
            485                 490                 495

Val Thr Lys Cys Cys Thr Glu Ser Leu Val Asn Arg Arg Pro Cys Phe
            500                 505                 510

Ser Ala Leu Gln Val Asp Glu Thr Tyr Val Pro Lys Glu Phe Ser Ala
            515                 520                 525

Glu Thr Phe Thr Phe His Ala Asp Leu Cys Thr Leu Pro Glu Ala Glu
            530                 535                 540

Lys Gln Ile Lys Lys Gln Ser Ala Leu Val Glu Leu Leu Lys His Lys
545                 550                 555                 560

Pro Lys Ala Thr Glu Glu Gln Leu Lys Thr Val Met Gly Asp Phe Gly
            565                 570                 575

Ser Phe Val Asp Lys Cys Cys Ala Ala Glu Asp Lys Glu Ala Cys Phe
            580                 585                 590

Ala Glu Glu Gly Pro Lys Leu Val Ala Ala Gln Ala Ala Leu Ala
            595                 600                 605

<210> SEQ ID NO 51
<211> LENGTH: 608
<212> TYPE: PRT
<213> ORGANISM: Canis familiaris

<400> SEQUENCE: 51

Met Lys Trp Val Thr Phe Ile Ser Leu Phe Phe Leu Phe Ser Ser Ala
1               5                   10                  15

Tyr Ser Arg Gly Leu Val Arg Arg Glu Ala Tyr Lys Ser Glu Ile Ala
            20                  25                  30

His Arg Tyr Asn Asp Leu Gly Glu Glu His Phe Arg Gly Leu Val Leu
            35                  40                  45

Val Ala Phe Ser Gln Tyr Leu Gln Gln Cys Pro Phe Glu Asp His Val
        50                  55                  60

Lys Leu Ala Lys Glu Val Thr Glu Phe Ala Lys Ala Cys Ala Ala Glu
65                  70                  75                  80

Glu Ser Gly Ala Asn Cys Asp Lys Ser Leu His Thr Leu Phe Gly Asp
                85                  90                  95

Lys Leu Cys Thr Val Ala Ser Leu Arg Asp Lys Tyr Gly Asp Met Ala
            100                 105                 110

Asp Cys Cys Glu Lys Gln Glu Pro Asp Arg Asn Glu Cys Phe Leu Ala
            115                 120                 125

His Lys Asp Asp Asn Pro Gly Phe Pro Pro Leu Val Ala Pro Glu Pro
            130                 135                 140

Asp Ala Leu Cys Ala Ala Phe Gln Asp Asn Glu Gln Leu Phe Leu Gly
145                 150                 155                 160

Lys Tyr Leu Tyr Glu Ile Ala Arg Arg His Pro Tyr Phe Tyr Ala Pro
                165                 170                 175

Glu Leu Leu Tyr Tyr Ala Gln Gln Tyr Lys Gly Val Phe Ala Glu Cys
            180                 185                 190

Cys Gln Ala Ala Asp Lys Ala Ala Cys Leu Gly Pro Lys Ile Glu Ala
            195                 200                 205

Leu Arg Glu Lys Val Leu Leu Ser Ser Ala Lys Glu Arg Phe Lys Cys
            210                 215                 220

Ala Ser Leu Gln Lys Phe Gly Asp Arg Ala Phe Lys Ala Trp Ser Val
225                 230                 235                 240

Ala Arg Leu Ser Gln Arg Phe Pro Lys Ala Asp Phe Ala Glu Ile Ser
```

```
            245                 250                 255
Lys Val Val Thr Asp Leu Thr Lys Val His Lys Glu Cys Cys His Gly
            260                 265                 270

Asp Leu Leu Glu Cys Ala Asp Asp Arg Ala Asp Leu Ala Lys Tyr Met
            275                 280                 285

Cys Glu Asn Gln Asp Ser Ile Ser Thr Lys Leu Lys Glu Cys Cys Asp
        290                 295                 300

Lys Pro Val Leu Glu Lys Ser Gln Cys Leu Ala Glu Val Glu Arg Asp
305                 310                 315                 320

Glu Leu Pro Gly Asp Leu Pro Ser Leu Ala Ala Asp Phe Val Glu Asp
                325                 330                 335

Lys Glu Val Cys Lys Asn Tyr Gln Glu Ala Lys Asp Val Phe Leu Gly
            340                 345                 350

Thr Phe Leu Tyr Glu Tyr Ala Arg Arg His Pro Glu Tyr Ser Val Ser
            355                 360                 365

Leu Leu Leu Arg Leu Ala Lys Glu Tyr Glu Ala Thr Leu Glu Lys Cys
        370                 375                 380

Cys Ala Thr Asp Asp Pro Pro Thr Cys Tyr Ala Lys Val Leu Asp Glu
385                 390                 395                 400

Phe Lys Pro Leu Val Asp Glu Pro Gln Asn Leu Val Lys Thr Asn Cys
                405                 410                 415

Glu Leu Phe Glu Lys Leu Gly Glu Tyr Gly Phe Gln Asn Ala Leu Leu
            420                 425                 430

Val Arg Tyr Thr Lys Lys Ala Pro Gln Val Ser Thr Pro Thr Leu Val
            435                 440                 445

Glu Val Ser Arg Lys Leu Gly Lys Val Gly Thr Lys Cys Cys Lys Lys
        450                 455                 460

Pro Glu Ser Glu Arg Met Ser Cys Ala Glu Asp Phe Leu Ser Val Val
465                 470                 475                 480

Leu Asn Arg Leu Cys Val Leu His Glu Lys Thr Pro Val Ser Glu Arg
                485                 490                 495

Val Thr Lys Cys Cys Ser Glu Ser Leu Val Asn Arg Arg Pro Cys Phe
            500                 505                 510

Ser Gly Leu Glu Val Asp Glu Thr Tyr Val Pro Lys Glu Phe Asn Ala
            515                 520                 525

Glu Thr Phe Thr Phe His Ala Asp Leu Cys Thr Leu Pro Glu Ala Glu
        530                 535                 540

Lys Gln Val Lys Lys Gln Thr Ala Leu Val Glu Leu Leu Lys His Lys
545                 550                 555                 560

Pro Lys Ala Thr Asp Glu Gln Leu Lys Thr Val Met Gly Asp Phe Gly
                565                 570                 575

Ala Phe Val Glu Lys Cys Cys Ala Ala Glu Asn Lys Glu Gly Cys Phe
            580                 585                 590

Ser Glu Glu Gly Pro Lys Leu Val Ala Ala Gln Ala Ala Leu Val
            595                 600                 605

<210> SEQ ID NO 52
<211> LENGTH: 55
<212> TYPE: PRT
<213> ORGANISM: Artificial Sequence
<220> FEATURE:
<223> OTHER INFORMATION: constructed sequence

<400> SEQUENCE: 52

Met Lys Trp Val Thr Phe Ile Ser Leu Phe Phe Leu Phe Ser Ser Ala
```

```
                 1               5                  10                 15
              Tyr Ser Arg Gly Leu Val Arg Arg His Ala Glu Gly Thr Phe Thr Ser
                             20                 25                 30
              Asp Val Ser Ser Tyr Leu Glu Gly Gln Ala Ala Lys Glu Phe Ile Ala
                             35                 40                 45
              Trp Leu Val Lys Gly Arg Gly
                             50                 55

<210> SEQ ID NO 53
<211> LENGTH: 609
<212> TYPE: PRT
<213> ORGANISM: Homo sapiens

<400> SEQUENCE: 53

Met Lys Trp Val Thr Phe Ile Ser Leu Leu Phe Leu Phe Ser Ser Ala
 1                5                  10                 15
Tyr Ser Arg Gly Val Phe Arg Arg Asp Ala His Lys Ser Glu Val Ala
                 20                 25                 30
His Arg Phe Lys Asp Leu Gly Glu Glu Asn Phe Lys Ala Leu Val Leu
             35                 40                 45
Ile Ala Phe Ala Gln Tyr Leu Gln Gln Cys Pro Phe Glu Asp His Val
     50                 55                 60
Lys Leu Val Asn Glu Val Thr Glu Phe Ala Lys Thr Cys Val Ala Asp
 65                 70                 75                 80
Glu Ser Ala Glu Asn Cys Asp Lys Ser Leu His Thr Leu Phe Gly Asp
                 85                 90                 95
Lys Leu Cys Thr Val Ala Thr Leu Arg Glu Thr Tyr Gly Glu Met Ala
            100                105                110
Asp Cys Cys Ala Lys Gln Glu Pro Glu Arg Asn Glu Cys Phe Leu Gln
        115                120                125
His Lys Asp Asp Asn Pro Asn Leu Pro Arg Leu Val Arg Pro Glu Val
    130                135                140
Asp Val Met Cys Thr Ala Phe His Asp Asn Glu Glu Thr Phe Leu Lys
145                150                155                160
Lys Tyr Leu Tyr Glu Ile Ala Arg Arg His Pro Tyr Phe Tyr Ala Pro
                165                170                175
Glu Leu Leu Phe Phe Ala Lys Arg Tyr Lys Ala Ala Phe Thr Glu Cys
            180                185                190
Cys Gln Ala Ala Asp Lys Ala Ala Cys Leu Leu Pro Lys Leu Asp Glu
        195                200                205
Leu Arg Asp Glu Gly Lys Ala Ser Ser Ala Lys Gln Arg Leu Lys Cys
    210                215                220
Ala Ser Leu Gln Lys Phe Gly Glu Arg Ala Phe Lys Ala Trp Ala Val
225                230                235                240
Ala Arg Leu Ser Gln Arg Phe Pro Lys Ala Glu Phe Ala Glu Val Ser
                245                250                255
Lys Leu Val Thr Asp Leu Thr Lys Val His Thr Glu Cys Cys His Gly
            260                265                270
Asp Leu Leu Glu Cys Ala Asp Asp Arg Ala Asp Leu Ala Lys Tyr Ile
        275                280                285
Cys Glu Asn Gln Asp Ser Ile Ser Ser Lys Leu Lys Glu Cys Cys Glu
    290                295                300
Lys Pro Leu Leu Glu Lys Ser His Cys Ile Ala Glu Val Glu Asn Asp
305                310                315                320
```

-continued

```
Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
        340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
        420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
        500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
        580                 585                 590

Ala Glu Glu Gly Lys Lys Leu Val Ala Ala Ser Gln Ala Ala Leu Gly
        595                 600                 605

Leu
```

<210> SEQ ID NO 54
<211> LENGTH: 55
<212> TYPE: PRT
<213> ORGANISM: Artificial Sequence
<220> FEATURE:
<223> OTHER INFORMATION: constructed sequence

<400> SEQUENCE: 54

```
Met Lys Trp Val Thr Phe Ile Ser Leu Leu Phe Leu Phe Ser Ser Ala
1               5                   10                  15

Tyr Ser Arg Gly Val Phe Arg Arg His Ala Glu Gly Thr Phe Thr Ser
            20                  25                  30

Asp Val Ser Ser Tyr Leu Glu Gly Gln Ala Ala Lys Glu Phe Ile Ala
        35                  40                  45

Trp Leu Val Lys Gly Arg Gly
    50                  55
```

```
<210> SEQ ID NO 55
<211> LENGTH: 5428
<212> TYPE: DNA
<213> ORGANISM: Artificial Sequence
<220> FEATURE:
<223> OTHER INFORMATION: constructed sequence
<220> FEATURE:
<221> NAME/KEY: polyA_signal
<222> LOCATION: (56)..(182)
<223> OTHER INFORMATION: rabit globin poly a
<220> FEATURE:
<221> NAME/KEY: repeat_region
<222> LOCATION: (271)..(400)
<223> OTHER INFORMATION: complement 3' ITR
<220> FEATURE:
<221> NAME/KEY: rep_origin
<222> LOCATION: (577)..(1032)
<220> FEATURE:
<221> NAME/KEY: misc_feature
<222> LOCATION: (1163)..(2020)
<223> OTHER INFORMATION: AP(R)
<220> FEATURE:
<221> NAME/KEY: rep_origin
<222> LOCATION: (2194)..(2782)
<220> FEATURE:
<221> NAME/KEY: repeat_region
<222> LOCATION: (3222)..(3351)
<223> OTHER INFORMATION: 5' ITR
<220> FEATURE:
<221> NAME/KEY: repeat_region
<222> LOCATION: (3419)..(3800)
<223> OTHER INFORMATION: CMV/IE/Promoter
<220> FEATURE:
<221> NAME/KEY: promoter
<222> LOCATION: (3803)..(4084)
<220> FEATURE:
<221> NAME/KEY: TATA_signal
<222> LOCATION: (4057)..(4060)
<220> FEATURE:
<221> NAME/KEY: Intron
<222> LOCATION: (4179)..(5151)
<223> OTHER INFORMATION: chicken\beta-actin\intron

<400> SEQUENCE: 55
ctctagagtc gacccgggcg gcctcgagga cggggtgaac tacgcctgag gatccgatct      60 ttttcccct ct gccaaaaatt atggggacat catgaagccc cttgagcatc tgacttctgg    120
ctaataaagg aaatttattt tcattgcaat agtgtgttgg aatttttttgt gtctctcact    180 cggaagcaat tcgttgatct gaatttcgac cacccataat acccattacc ctggtagata    240
agtagcatgg cgggttaatc attaactaca aggaacccct agtgatggag ttggccactc    300
cctctctgcg cgctcgctcg ctcactgagg ccgggcgacc aaaggtcgcc cgacgcccgg    360
gctttgcccg gcggcctca gtgagcgagc gagcgcgcag ccttaattaa cctaattcac    420
tggccgtcgt tttacaacgt cgtgactggg aaaaccctgg cgttacccaa cttaatcgcc    480
ttgcagcaca tccccctttc gccagctggc gtaatagcga agaggcccgc accgatcgcc    540
cttcccaaca gttgcgcagc ctgaatggcg aatgggacgc gccctgtagc ggcgcattaa    600
gcgcggcggg tgtggtggtt acgcgcagcg tgaccgctac acttgccagc gccctagcgc    660
ccgctccttt cgctttcttc ccttcctttc tcgccacgtt cgccggcttt ccccgtcaag    720
ctctaaatcg ggggctccct ttagggttcc gatttagtgc tttacggcac ctcgacccca    780
aaaaacttga ttagggtgat ggttcacgta gtgggccatc gccctgatag acggtttttc    840
gccctttgac gttggagtcc acgttcttta atagtggact cttgttccaa actggaacaa    900
cactcaaccc tatctcggtc tattcttttg atttataagg gattttgccg atttcggcct    960
attggttaaa aaatgagctg atttaacaaa aatttaacgc gaattttaac aaaatattaa   1020
```

```
cgcttacaat ttaggtggca cttttcgggg aaatgtgcgc ggaacccta tttgtttatt      1080 tttctaaata cattcaaata tgtatccgct catgagacaa taaccctgat aaatgcttca      1140
ataatattga aaaggaaga gtatgagtat tcaacatttc cgtgtcgccc ttattccctt      1200
ttttgcggca ttttgccttc ctgttttttgc tcacccagaa acgctggtga agtaaaaga     1260 tgctgaagat cagttgggtg cacgagtggg ttacatcgaa ctggatctca acagcggtaa     1320
gatccttgag agttttcgcc ccgaagaacg ttttccaatg atgagcactt ttaaagttct     1380
gctatgtggc gcggtattat cccgtattga cgccgggcaa gagcaactcg gtcgccgcat     1440
acactattct cagaatgact tggttgagta ctcaccagtc acagaaaagc atcttacgga     1500
tggcatgaca gtaagagaat tatgcagtgc tgccataacc atgagtgata acactgcggc     1560
caacttactt ctgacaacga tcggaggacc gaaggagcta accgcttttt tgcacaacat     1620
gggggatcat gtaactcgcc ttgatcgttg gaaccggag ctgaatgaag ccataccaaa      1680
cgacgagcgt gacaccacga tgcctgtagc aatggcaaca acgttgcgca aactattaac     1740
tggcgaacta cttactctag cttcccggca acaattaata gactggatgg aggcggataa     1800
agttgcagga ccacttctgc gctcggccct tccggctggc tggtttattg ctgataaatc     1860
tggagccggt gagcgtgggt ctcgcggtat cattgcagca ctggggccag atggtaagcc     1920
ctcccgtatc gtagttatct acacgacggg gagtcaggca actatggatg aacgaaatag     1980
acagatcgct gagataggtg cctcactgat taagcattgg taactgtcag accaagttta     2040
ctcatatata ctttagattg atttaaaact tcatttttaa tttaaaagga tctaggtgaa     2100
gatccttttt gataatctca tgaccaaaat cccttaacgt gagttttcgt tccactgagc     2160
gtcagacccc gtagaaaaga tcaaaggatc ttcttgagat cctttttttc tgcgcgtaat     2220
ctgctgcttg caaacaaaaa aaccaccgct accagcggtg gtttgtttgc cggatcaaga     2280
gctaccaact ctttttccga aggtaactgg cttcagcaga gcgcagatac caaatactgt     2340
tcttctagtg tagccgtagt taggccacca cttcaagaac tctgtagcac cgcctacata     2400
cctcgctctg ctaatcctgt taccagtggc tgctgccagt ggcgataagt cgtgtcttac     2460
cgggttggac tcaagacgat agttaccgga taaggcgcag cggtcgggct gaacggggg      2520 ttcgtgcaca cagcccagct tggagcgaac gacctacacc gaactgagat acctacagcg     2580
tgagctatga gaaagcgcca cgcttcccga agggagaaag gcggacaggt atccggtaag     2640
cggcagggtc ggaacaggag agcgcacgag ggagcttcca gggggaaacg cctggtatct     2700
ttatagtcct gtcgggtttc gccacctctg acttgagcgt cgatttttgt gatgctcgtc     2760
aggggggcgg agcctatgga aaaacgccag caacgcggcc ttttacggt tcctggcctt      2820 ttgctggcct tttgctcaca tgttctttcc tgcgttatcc cctgattctg tggataaccg     2880
tattaccgcc tttgagtgag ctgataccgc tcgccgcagc cgaacgaccg agcgcagcga     2940
gtcagtgagc gaggaagcgg aagagcgccc aatacgcaaa ccgcctctcc ccgcgcgttg     3000
gccgattcat taatgcagct ggcacgacag gtttcccgac tggaaagcgg gcagtgagcg     3060
caacgcaatt aatgtgagtt agctcactca ttaggcaccc caggctttac actttatgct     3120
tccggctcgt atgttgtgtg gaattgtgag cggataacaa tttcacacag gaaacagcta     3180
tgaccatgat tacgccagat ttaattaagg ccttaattag gctgcgcgct cgctcgctca     3240
ctgaggccgc ccgggcaaag cccgggcgtc gggcgacctt ggtcgcccg gcctcagtga     3300 gcgagcgagc gcgcagagag ggagtggcca actccatcac taggggttcc ttgtagttaa     3360
tgattaaccc gccatgctac ttatctacca gggtaatggg gatcctctag aactatagct     3420
```

```
agtcgacatt gattattgac tagttattaa tagtaatcaa ttacgggtc attagttcat   3480 agcccatata tggagttccg cgttacataa cttacggtaa atggcccgcc tggctgaccg   3540
cccaacgacc cccgcccatt gacgtcaata atgacgtatg ttcccatagt aacgccaata   3600
gggactttcc attgacgtca atgggtggac tatttacggt aaactgccca cttggcagta   3660
catcaagtgt atcatatgcc aagtacgccc cctattgacg tcaatgacgg taaatggccc   3720
gcctggcatt atgcccagta catgacctta tgggactttc ctacttggca gtacatctac   3780
gtattagtca tcgctattac catggtcgag gtgagcccca cgttctgctt cactctcccc   3840 atctccccc cctccccacc cccaattttg tatttattta ttttttaatt attttgtgca   3900
gcgatggggg cggggggggg ggggggcgc gcgccaggcg gggcggggcg gggcgagggg   3960
cggggcgggg cgaggcggag aggtgcggcg gcagccaatc agagcggcgc gctccgaaag   4020 tttccttta tggcgaggcg gcggcggcgg cggccctata aaaagcgaag cgcgcggcgg   4080
gcggggagtc gctgcgacgc tgccttcgcc ccgtgcccg ctccgccgcc gcctcgcgcc   4140
gcccgccccg gctctgactg accgcgttac tcccacaggt gagcgggcgg gacggccctt   4200
ctcctccggg ctgtaattag cgcttggttt aatgacggct tgtttctttt ctgtggctgc   4260
gtgaaagcct tgaggggctc cgggagggcc ctttgtgcgg gggagcggc tcgggggtg    4320 cgtgcgtgtg tgtgtgcgtg gggagcgccg cgtgcggctc cgcgctgccc ggcggctgtg   4380
agcgctgcgg gcgcggcgcg gggctttgtg cgctccgcag tgtgcgcgag gggagcgcgg   4440
ccgggggcgg tgccccgcgg tgcgggggg gctgcgaggg gaacaaaggc tgcgtgcggg   4500
gtgtgtgcgt gggggggtga gcaggggtg tgggcgcgtc ggtcgggctg caacccccc    4560 tgcaccccc tccccgagtt gctgagcacg gcccggcttc gggtgcgggg ctccgtacgg   4620
ggcgtggcgc ggggctcgcc gtgccgggcg ggggtggcg gcaggtgggg gtgccgggcg   4680
gggcggggcc gcctcgggcc ggggagggct cggggaggg gcgcggcggc ccccggagcg   4740
ccggcggctg tcgaggcgcg gcgagccgca gccattgcct tttatggtaa tcgtgcgaga   4800
gggcgcaggg acttcctttg tcccaaatct gtgcggagcc gaaatctggg aggcgccgcc   4860 gcacccctc tagcgggcgc ggggcgaagc ggtgcgcgcg cggcaggaag gaaatgggcg   4920
gggagggcct tcgtgcgtcg ccgcgccgcc gtcccttct ccctctccag cctcggggct   4980
gtccgcgggg gacgcgctgc cttcgggggg gacggggcag ggcggggttc ggcttctggc   5040
gtgtgaccgg cggctctaga gcctctgcta accatgttca tgccttcttc ttttccctac   5100
agctcctggg caacgtgctg gttattgtgc tgtctcatca ttttggcaaa gaattcgcca   5160
ccatgggagc cgatgctaga cctctggag tgcgggctgg cggcggagga agaggcgctg   5220
caagacctgg cacaagcagc agagcactgc ctccacctct gccccctctg agctttctcc   5280
tgctgctgct ggctgcccct ggcgctagag ccagaaaaag aaggcacgcc gagggcacct   5340
tcaccagcga cgtgtccagc tacctggaag gccaggccgc caaagagttt atcgcctggc   5400
tcgtgaaggg cagaggctga tgaggtac                                     5428
```

<210> SEQ ID NO 56
<211> LENGTH: 93
<212> TYPE: DNA
<213> ORGANISM: Artificial Sequence
<220> FEATURE:
<223> OTHER INFORMATION: constructed sequence

<400> SEQUENCE: 56
catgctgaag ggacctttac cagtgatgta agttcttatt tggaaggcca agctgccaag    60
gaattcattg cttggctggt gaaaggccgg gga    93

<210> SEQ ID NO 57
<211> LENGTH: 5437
<212> TYPE: DNA
<213> ORGANISM: Artificial Sequence
<220> FEATURE:
<223> OTHER INFORMATION: constructed sequence
<220> FEATURE:
<221> NAME/KEY: misc_feature
<222> LOCATION: (12)..(170)
<223> OTHER INFORMATION: leader
<220> FEATURE:
<221> NAME/KEY: misc_feature
<222> LOCATION: (171)..(182)
<223> OTHER INFORMATION: furin site
<220> FEATURE:
<221> NAME/KEY: misc_feature
<222> LOCATION: (183)..(275)
<223> OTHER INFORMATION: GLP1
<220> FEATURE:
<221> NAME/KEY: polyA_signal
<222> LOCATION: (342)..(468)
<223> OTHER INFORMATION: Rabbit\globin\poly\A
<220> FEATURE:
<221> NAME/KEY: rep_origin
<222> LOCATION: (863)..(1318)
<223> OTHER INFORMATION: f1\ori (complement)
<220> FEATURE:
<221> NAME/KEY: misc_feature
<222> LOCATION: (1449)..(2306)
<223> OTHER INFORMATION: AP(R)
<220> FEATURE:
<221> NAME/KEY: rep_origin
<222> LOCATION: (2480)..(3068)
<223> OTHER INFORMATION: Origin\of\replication
<220> FEATURE:
<221> NAME/KEY: repeat_region
<222> LOCATION: (3508)..(3637)
<223> OTHER INFORMATION: 5' ITR
<220> FEATURE:
<221> NAME/KEY: misc_feature
<222> LOCATION: (3705)..(4086)
<223> OTHER INFORMATION: CMV\IE\promoter
<220> FEATURE:
<221> NAME/KEY: promoter
<222> LOCATION: (4089)..(4370)
<223> OTHER INFORMATION: CB promoter
<220> FEATURE:
<221> NAME/KEY: TATA_signal
<222> LOCATION: (4343)..(4346)
<220> FEATURE:
<221> NAME/KEY: Intron
<222> LOCATION: (4465)..(5437)
<223> OTHER INFORMATION: chicken\beta-actin\intron

<400> SEQUENCE: 57
aattcgccac catgggcgtg gacggccgga tattcttcct gatgcccagc atggccttcc    60
agctgctgaa cgagagcaga cccagcagcc tgctgatcca gatgttcccc ggcctgagct    120
tcatctgcac caccgtgctg agcaagcagc acgccgccaa ggtgctgatc cggaagagaa    180
ggcacgccga gggcaccttc accagcgacg tgtccagcta cctggaagga caggccgcca    240
aagagtttat cgcctggctc gtgaagggca gaggctgatg aggtacctct agagtcgacc    300
cgggcggcct cgaggacggg gtgaactacg cctgaggatc cgatcttttt ccctctgcca    360
aaaattatgg ggacatcatg aagccccttg agcatctgac ttctggctaa taaggaaat    420 ttattttcat tgcaatagtg tgttggaatt ttttgtgtct ctcactcgga agcaattcgt    480
tgatctgaat ttcgaccacc cataataccc attaccctgg tagataagta gcatggcggg    540

```
ttaatcatta actacaagga acccctagtg atggagttgg ccactccctc tctgcgcgct    600
cgctcgctca ctgaggccgg gcgaccaaag gtcgcccgac gcccgggctt tgcccgggcg    660
gcctcagtga gcgagcgagc gcgcagcctt aattaaccta attcactggc cgtcgtttta    720
caacgtcgtg actgggaaaa ccctggcgtt acccaactta atcgccttgc agcacatccc    780
cctttcgcca gctggcgtaa tagcgaagag gcccgcaccg atcgcccttc ccaacagttg    840
cgcagcctga atggcgaatg gacgcgccc tgtagcggcg cattaagcgc ggcgggtgtg    900
gtggttacgc gcagcgtgac cgctacactt gccagcgccc tagcgcccgc tcctttcgct    960
ttcttccctt cctttctcgc cacgttcgcc ggctttcccc gtcaagctct aaatcggggg   1020
ctcccttag ggttccgatt tagtgcttta cggcacctcg accccaaaaa acttgattag   1080
ggtgatggtt cacgtagtgg gccatcgccc tgatagacgg ttttcgccc tttgacgttg   1140
gagtccacgt tctttaatag tggactcttg ttccaaactg gaacaacact caaccctatc   1200
tcggtctatt cttttgattt ataagggatt ttgccgattt cggcctattg gttaaaaaat   1260
gagctgattt aacaaaaatt taacgcgaat tttaacaaaa tattaacgct tacaatttag   1320
gtggcacttt tcggggaaat gtgcgcggaa cccctatttg tttattttc taaatacatt   1380
caaatatgta tccgctcatg agacaataac cctgataaat gcttcaataa tattgaaaaa   1440
ggaagagtat gagtattcaa catttccgtg tcgcccttat ccctttttt gcggcatttt   1500
gccttcctgt ttttgctcac ccagaaacgc tggtgaaagt aaaagatgct gaagatcagt   1560
tgggtgcacg agtgggttac atcgaactgg atctcaacag cggtaagatc cttgagagtt   1620
ttcgccccga agaacgtttt ccaatgatga gcacttttaa agttctgcta tgtggcgcgg   1680
tattatcccg tattgacgcc gggcaagagc aactcggtcg ccgcatacac tattctcaga   1740
atgacttggt tgagtactca ccagtcacag aaaagcatct tacggatggc atgacagtaa   1800
gagaattatg cagtgctgcc ataaccatga gtgataacac tgcggccaac ttacttctga   1860
caacgatcgg aggaccgaag gagctaaccg cttttttgca caacatgggg gatcatgtaa   1920
ctcgccttga tcgttgggaa ccggagctga atgaagccat accaaacgac gagcgtgaca   1980
ccacgatgcc tgtagcaatg gcaacaacgt tgcgcaaact attaactggc gaactactta   2040
ctctagcttc ccggcaacaa ttaatagact ggatggaggc ggataaagtt gcaggaccac   2100
ttctgcgctc ggcccttccg gctggctggt ttattgctga taaatctgga gccggtgagc   2160
gtgggtctcg cggtatcatt gcagcactgg ggccagatgg taagccctcc cgtatcgtag   2220
ttatctacac gacggggagt caggcaacta tggatgaacg aaatagacag atcgctgaga   2280
taggtgcctc actgattaag cattggtaac tgtcagacca agtttactca tatatacttt   2340
agattgattt aaaacttcat ttttaattta aaaggatcta ggtgaagatc ctttttgata   2400
atctcatgac caaaatccct taacgtgagt tttcgttcca ctgagcgtca gaccccgtag   2460
aaaagatcaa aggatcttct tgagatcctt ttttctgcg cgtaatctgc tgcttgcaaa   2520
caaaaaaacc accgctacca gcggtggttt gtttgccgga tcaagagcta ccaactcttt   2580
ttccgaaggt aactggcttc agcagagcgc agataccaaa tactgttctt ctagtgtagc   2640
cgtagttagg ccaccacttc aagaactctg tagcaccgcc tacatacctc gctctgctaa   2700
tcctgttacc agtggctgct gccagtggcg ataagtcgtg tcttaccggg ttggactcaa   2760
gacgatagtt accggataag gcgcagcggt cgggctgaac ggggggttcg tgcacacagc   2820
ccagcttgga gcgaacgacc tacaccgaac tgagatacct acagcgtgag ctatgagaaa   2880
gcgccacgct tcccgaaggg agaaaggcgg acaggtatcc ggtaagcggc agggtcggaa   2940
```

```
caggagagcg cacgagggag cttccagggg gaaacgcctg gtatctttat agtcctgtcg   3000
ggtttcgcca cctctgactt gagcgtcgat ttttgtgatg ctcgtcaggg gggcggagcc   3060
tatggaaaaa cgccagcaac gcggccttt tacggttcct ggccttttgc tggccttttg   3120
ctcacatgtt ctttcctgcg ttatccctg attctgtgga taaccgtatt accgcctttg   3180
agtgagctga taccgctcgc cgcagccgaa cgaccgagcg cagcgagtca gtgagcgagg   3240
aagcggaaga gcgcccaata cgcaaaccgc ctctccccgc gcgttggccg attcattaat   3300
gcagctggca cgacaggttt cccgactgga aagcgggcag tgagcgcaac gcaattaatg   3360
tgagttagct cactcattag gcaccccagg ctttacactt tatgcttccg gctcgtatgt   3420
tgtgtggaat tgtgagcgga taacaatttc acacaggaaa cagctatgac catgattacg   3480
ccagatttaa ttaaggcctt aattaggctg cgcgctcgct cgctcactga gccgcccgg    3540 gcaaagcccg ggcgtcgggc gacctttggt cgcccggcct cagtgagcga gcgagcgcgc   3600
agagagggag tggccaactc catcactagg ggttccttgt agttaatgat taacccgcca   3660
tgctacttat ctaccagggt aatggggatc ctctagaact atagctagtc gacattgatt   3720
attgactagt tattaatagt aatcaattac ggggtcatta gttcatagcc catatatgga   3780
gttccgcgtt acataactta cggtaaatgg cccgcctggc tgaccgccca cgacccccg    3840 cccattgacg tcaataatga cgtatgttcc catagtaacg ccaatagga ctttccattg    3900 acgtcaatgg gtggactatt tacggtaaac tgcccacttg gcagtacatc aagtgtatca   3960
tatgccaagt acgccccta ttgacgtcaa tgacggtaaa tggcccgcct ggcattatgc    4020
ccagtacatg accttatggg actttcctac ttggcagtac atctacgtat tagtcatcgc   4080
tattaccatg gtcgaggtga gccccacgtt ctgcttcact ctccccatct cccccccctc   4140
cccaccccca ttttgtatt tatttatttt ttaattattt tgtgcagcga tggggcggg    4200 gggggggggg gggcgcgcgc caggcgggc ggggcgggc gagggcggg gcggggcgag    4260 gcggagaggt gcggcggcag ccaatcagag cggcgcgctc cgaaagtttc cttttatggc   4320
gaggcggcgg cggcggcggc cctataaaaa gcgaagcgcg cggcgggcgg ggagtcgctg   4380
cgacgctgcc ttcgccccgt gccccgctcc gccgccgcct cgcgccgccc gccccggctc   4440
tgactgaccg cgttactccc acaggtgagc gggcgggacg gcccttctcc tccgggctgt   4500
aattagcgct tggtttaatg acggcttgtt tcttttctgt ggctgcgtga aagccttgag   4560
ggctccgggg agggccctt gtgcgggggg agcggctcgg ggggtgcgtg cgtgtgtgtg    4620
tgcgtgggga gcgccgcgtg cggctccgcg ctgcccggcg gctgtgagcg ctgcgggcgc   4680 ggcgcgggc tttgtgcgct ccgcagtgtg cgcgagggga gcgcggccgg gggcggtgcc   4740
ccgcggtgcg ggggggctg cgaggggaac aaaggctgcg tgcggggtgt gtgcgtgggg    4800
gggtgagcag ggggtgtggg cgcgtcggtc gggctgcaac ccccctgca ccccctccc    4860 cgagttgctg agcacggccc ggcttcgggt gcggggctcc gtacgggcg tggcgcgggg    4920 ctcgccgtgc cgggcgggg gtggcggcag gtgggggtgc cgggcgggc ggggccgcct    4980 cgggccgggg agggctcggg ggaggggcgc ggcggccccc ggagcgccgg cggctgtcga   5040
ggcgcggcga gccgcagcca ttgccttta tggtaatcgt gcgagagggc gcaggactt    5100 cctttgtccc aaatctgtgc ggagccgaaa tctgggaggc gccgccgcac cccctctagc   5160
gggcgcgggg cgaagcggtg cggcgccggc aggaaggaaa tgggcgggga gggccttcgt   5220
gcgtcgccgc gccgccgtcc ccttctccct ctccagcctc ggggctgtcc gcgggggac    5280
```

```
ggctgccttc ggggggacg gggcagggcg gggttcggct tctggcgtgt gaccggcggc    5340
tctagagcct ctgctaacca tgttcatgcc ttcttctttt tcctacagct cctgggcaac    5400
gtgctggtta ttgtgctgtc tcatcatttt ggcaaag                              5437

<210> SEQ ID NO 58
<211> LENGTH: 5338
<212> TYPE: DNA
<213> ORGANISM: Artificial Sequence
<220> FEATURE:
<223> OTHER INFORMATION: constructed sequence
<220> FEATURE:
<221> NAME/KEY: polyA_signal
<222> LOCATION: (56)..(182)
<223> OTHER INFORMATION: Rabbit\globin\poly\A
<220> FEATURE:
<221> NAME/KEY: repeat_region
<222> LOCATION: (271)..(400)
<223> OTHER INFORMATION: 3' ITR (complement)
<220> FEATURE:
<221> NAME/KEY: rep_origin
<222> LOCATION: (577)..(1032)
<223> OTHER INFORMATION: f1 ori (complement)
<220> FEATURE:
<221> NAME/KEY: misc_feature
<222> LOCATION: (1163)..(2020)
<223> OTHER INFORMATION: AP(R)
<220> FEATURE:
<221> NAME/KEY: rep_origin
<222> LOCATION: (2194)..(2782)
<223> OTHER INFORMATION: Origin\of\replication
<220> FEATURE:
<221> NAME/KEY: repeat_region
<222> LOCATION: (3222)..(3351)
<223> OTHER INFORMATION: 5' ITR
<220> FEATURE:
<221> NAME/KEY: misc_feature
<222> LOCATION: (3419)..(3800)
<223> OTHER INFORMATION: CMV\IE\promoter
<220> FEATURE:
<221> NAME/KEY: promoter
<222> LOCATION: (3803)..(4084)
<223> OTHER INFORMATION: DB promoter
<220> FEATURE:
<221> NAME/KEY: TATA_signal
<222> LOCATION: (4057)..(4060)
<220> FEATURE:
<221> NAME/KEY: Intron
<222> LOCATION: (4179)..(5151)
<223> OTHER INFORMATION: chicken\beta-actin\intron

<400> SEQUENCE: 58
ctctagagtc gacccgggcg gcctcgagga cggggtgaac tacgcctgag gatccgatct     60
ttttccctct gccaaaaatt atggggacat catgaagccc cttgagcatc tgacttctgg   120
ctaataaagg aaatttattt tcattgcaat agtgtgttgg aatttttttgt gtctctcact   180 cggaagcaat tcgttgatct gaatttcgac cacccataat acccattacc ctggtagata   240
agtagcatgg cgggttaatc attaactaca aggaaccct agtgatggag ttggccactc    300
cctctctgcg cgctcgctcg ctcactgagg cgggcgacc aaaggtcgcc cgacgcccgg    360
gctttgcccg ggcggcctca gtgagcgagc gagcgcgcag ccttaattaa cctaattcac    420
tggccgtcgt tttacaacgt cgtgactggg aaaaccctgg cgttacccaa cttaatcgcc    480
ttgcagcaca tccccctttc gccagctggc gtaatagcga agaggcccgc accgatcgcc    540
cttcccaaca gttgcgcagc ctgaatggcg aatgggacgc gccctgtagc ggcgcattaa    600
gcgcggcggg tgtggtggtt acgcgcagcg tgaccgctac acttgccagc gccctagcgc    660
ccgctccttt cgctttcttc ccttcctttc tcgccacgtt cgccggcttt ccccgtcaag    720
```

```
ctctaaatcg ggggctccct ttagggttcc gatttagtgc tttacggcac ctcgacccca   780
aaaaacttga ttagggtgat ggttcacgta gtgggccatc gccctgatag acggttttc    840
gcccttgac gttggagtcc acgttcttta atagtggact cttgttccaa actggaacaa    900
cactcaaccc tatctcggtc tattctttg atttataagg gattttgccg atttcggcct    960
attggttaaa aaatgagctg atttaacaaa aatttaacgc gaattttaac aaaatattaa  1020
cgcttacaat ttaggtggca cttttcgggg aaatgtgcgc ggaacccta tttgtttatt   1080
tttctaaata cattcaaata tgtatccgct catgagacaa taaccctgat aaatgcttca  1140
ataatattga aaaggaaga gtatgagtat tcaacatttc cgtgtcgccc ttattccctt   1200
ttttgcggca ttttgccttc ctgttttgc tcacccagaa acgctggtga agtaaaaga   1260
tgctgaagat cagttgggtg cacgagtggg ttacatcgaa ctggatctca acagcggtaa  1320
gatccttgag agttttcgcc ccgaagaacg ttttccaatg atgagcactt ttaaagttct  1380
gctatgtggc gcggtattat cccgtattga cgccgggcaa gagcaactcg gtcgccgcat  1440
acactattct cagaatgact tggttgagta ctcaccagtc acagaaaagc atcttacgga  1500
tggcatgaca gtaagagaat tatgcagtgc tgccataacc atgagtgata acactgcggc  1560
caacttactt ctgacaacga tcggaggacc gaaggagcta accgcttttt tgcacaacat  1620
gggggatcat gtaactcgcc ttgatcgttg ggaaccggag ctgaatgaag ccataccaaa  1680
cgacgagcgt gacaccacga tgcctgtagc aatggcaaca acgttgcgca aactattaac  1740
tggcgaacta cttactctag cttcccggca acaattaata gactggatgg aggcggataa  1800
agttgcagga ccacttctgc gctcggccct tccggctggc tggtttattg ctgataaatc  1860
tggagccggt gagcgtgggt ctcgcggtat cattgcagca ctggggccag atggtaagcc  1920
ctcccgtatc gtagttatct acacgacggg gagtcaggca actatggatg aacgaaatag  1980
acagatcgct gagataggtg cctcactgat taagcattgg taactgtcag accaagttta  2040
ctcatatata ctttagattg atttaaaact tcatttttaa tttaaaagga tctaggtgaa  2100
gatccttttt gataatctca tgaccaaaat cccttaacgt gagttttcgt tccactgagc  2160
gtcagacccc gtagaaaaga tcaaaggatc ttcttgagat cctttttttc tgcgcgtaat  2220
ctgctgcttg caaacaaaaa aaccaccgct accagcggtg gtttgtttgc cggatcaaga  2280
gctaccaact cttttccga aggtaactgg cttcagcaga gcgcagatac caaatactgt   2340
tcttctagtg tagccgtagt taggccacca cttcaagaac tctgtagcac cgcctacata  2400
cctcgctctg ctaatcctgt taccagtggc tgctgccagt ggcgataagt cgtgtcttac  2460
cgggttggac tcaagacgat agttaccgga taaggcgcag cggtcgggct gaacggggg   2520
ttcgtgcaca cagcccagct tggagcgaac gacctacacc gaactgagat acctacagcg  2580
tgagctatga gaaagcgcca cgcttcccga agggagaaag gcggacaggt atccggtaag  2640
cggcagggtc ggaacaggag agcgcacgag ggagcttcca gggggaaacg cctggtatct  2700
ttatagtcct gtcgggtttc gccacctctg acttgagcgt cgatttttgt gatgctcgtc  2760
agggggggcgg agcctatgga aaaacgccag caacgcggcc ttttacggt tcctggcctt   2820
ttgctggcct tttgctcaca tgttctttcc tgcgttatcc cctgattctg tggataaccg  2880
tattaccgcc tttgagtgag ctgataccgc tcgccgcagc cgaacgaccg agcgcagcga  2940
gtcagtgagc gaggaagcgg aagagcgccc aatacgcaaa ccgcctctcc ccgcgcgttg  3000
gccgattcat taatgcagct ggcacgacag gtttcccgac tggaaagcgg gcagtgagcg  3060
caacgcaatt aatgtgagtt agctcactca ttaggcaccc caggctttac actttatgct  3120
```

```
tccggctcgt atgttgtgtg gaattgtgag cggataacaa tttcacacag gaaacagcta    3180
tgaccatgat tacgccagat ttaattaagg ccttaattag gctgcgcgct cgctcgctca    3240
ctgaggccgc ccgggcaaag cccgggcgtc gggcgacctt tggtcgcccg gcctcagtga    3300
gcgagcgagc gcgcagagag ggagtggcca actccatcac tagggggttcc ttgtagttaa    3360 tgattaaccc gccatgctac ttatctacca gggtaatggg gatcctctag aactatagct    3420
agtcgacatt gattattgac tagttattaa tagtaatcaa ttacgggtc attagttcat    3480 agcccatata tggagttccg cgttacataa cttacggtaa atggcccgcc tggctgaccg    3540
cccaacgacc cccgcccatt gacgtcaata atgacgtatg ttcccatagt aacgccaata    3600
gggactttcc attgacgtca atgggtggac tatttacggt aaactgccca cttggcagta    3660
catcaagtgt atcatatgcc aagtacgccc cctattgacg tcaatgacgg taaatggccc    3720
gcctggcatt atgcccagta catgacctta tgggactttc ctacttggca gtacatctac    3780
gtattagtca tcgctattac catggtcgag gtgagcccca cgttctgctt cactctcccc    3840
atctcccccc cctccccacc cccaattttg tatttattta ttttttaatt attttgtgca    3900
gcgatggggg cggggggggg ggggggcgc gcgccaggcg gggcggggcg gggcgagggg    3960
cggggcgggg cgaggcggag aggtgcggcg gcagccaatc agagcggcgc gctccgaaag    4020 tttccttttta tggcgaggcg gcggcggcgg cggccctata aaaagcgaag cgcgcggcgg    4080
gcggggagtc gctgcgacgc tgccttcgcc ccgtgccccg ctccgccgcc gcctcgcgcc    4140
gcccgccccg gctctgactg accgcgttac tcccacaggt gagcgggcgg gacgcccctt    4200
ctcctccggg ctgtaattag cgcttggttt aatgacggct tgtttctttt ctgtggctgc    4260
gtgaaagcct tgaggggctc cgggagggcc ctttgtgcgg gggagcggc tcggggggtg    4320 cgtgcgtgtg tgtgtgcgtg gggagcgccg cgtgcggctc cgcgctgccc ggcggctgtg    4380
agcgctgcgg gcgcggcgcg gggctttgtg cgctccgcag tgtgcgcgag gggagcgcgg    4440
ccgggggcgg tgccccgcgg tgcgggggg gctgcgaggg gaacaaaggc tgcgtgcggg    4500
gtgtgtgcgt gggggggtga gcaggggtg tgggcgcgtc ggtcgggctg caaccccccc    4560 tgcaccccccc tccccgagtt gctgagcacg gcccggcttc gggtgcgggg ctccgtacgg    4620
ggcgtggcgc ggggctcgcc gtgccgggcg ggggtggcg caggtgggg gtgccgggcg    4680 gggcggggcc gcctcgggcc ggggagggct cggggaggg gcgcggcggc ccccggagcg    4740
ccggcggctg tcgaggcgcg gcgagccgca gccattgcct tttatggtaa tcgtgcgaga    4800
gggcgcaggg acttcctttg tcccaaatct gtgcggagcc gaaatctggg aggcgccgcc    4860 gcacccctc tagcgggcgc ggggcgaagc ggtgcggcgc cggcaggaag gaaatgggcg    4920
gggagggcct tcgtgcgtcg ccgcgccgcc gtccccttct ccctctccag cctcgggct    4980 gtccgcgggg ggacggctgc cttcgggggg gacggggcag ggcggggttc ggcttctggc    5040
gtgtgaccgg cggctctaga gcctctgcta accatgttca tgccttcttc tttttcctac    5100
agctcctggg caacgtgctg gttattgtgc tgtctcatca ttttggcaaa gaattcgcca    5160
ccatgtacaa gatccagctg ctgagctgta tcgccctgac cctgatcctc gtgaccaaca    5220
gcagaaagaa gagacacgcc gagggcacct tcaccagcga cgtgtcctct tacctggaag    5280
gccaggccgc caaagagttt atcgcctggc tcgtgaaggg cagaggctga tgaggtac    5338
```

<210> SEQ ID NO 59
<211> LENGTH: 5395
<212> TYPE: DNA

```
<213> ORGANISM: Artificial Sequence
<220> FEATURE:
<223> OTHER INFORMATION: constructed sequence
<220> FEATURE:
<221> NAME/KEY: polyA_signal
<222> LOCATION: (56)..(182)
<223> OTHER INFORMATION: Rabbit\globin\poly\A
<220> FEATURE:
<221> NAME/KEY: repeat_region
<222> LOCATION: (271)..(400)
<223> OTHER INFORMATION: 3' ITR (complement)
<220> FEATURE:
<221> NAME/KEY: rep_origin
<222> LOCATION: (577)..(1032)
<223> OTHER INFORMATION: F1 ori
<220> FEATURE:
<221> NAME/KEY: misc_feature
<222> LOCATION: (1163)..(2020)
<223> OTHER INFORMATION: AP(R)
<220> FEATURE:
<221> NAME/KEY: rep_origin
<222> LOCATION: (2194)..(2782)
<223> OTHER INFORMATION: Origin\of\replication
<220> FEATURE:
<221> NAME/KEY: misc_feature
<222> LOCATION: (3083)..(4084)
<223> OTHER INFORMATION: CB promoter
<220> FEATURE:
<221> NAME/KEY: repeat_region
<222> LOCATION: (3222)..(3351)
<223> OTHER INFORMATION: 5' ITR
<220> FEATURE:
<221> NAME/KEY: repeat_region
<222> LOCATION: (3419)..(3800)
<223> OTHER INFORMATION: CMV\IE\promoter
<220> FEATURE:
<221> NAME/KEY: TATA_signal
<222> LOCATION: (4057)..(4060)
<220> FEATURE:
<221> NAME/KEY: Intron
<222> LOCATION: (4179)..(5151)
<223> OTHER INFORMATION: chicken\beta-actin\intron
<220> FEATURE:
<221> NAME/KEY: misc_feature
<222> LOCATION: (5163)..(5291)
<223> OTHER INFORMATION: leader
<220> FEATURE:
<221> NAME/KEY: misc_feature
<222> LOCATION: (5292)..(5384)
<223> OTHER INFORMATION: GLP1

<400> SEQUENCE: 59
ctctagagtc gacccgggcg gcctcgagga cggggtgaac tacgcctgag gatccgatct    60 ttttcccctct gccaaaaatt atggggacat catgaagccc cttgagcatc tgacttctgg   120
ctaataaagg aaatttattt tcattgcaat agtgtgttgg aatttttttgt gtctctcact   180 cggaagcaat tcgttgatct gaatttcgac cacccataat acccattacc ctggtagata   240
agtagcatgg cgggttaatc attaactaca aggaacccct agtgatggag ttggccactc   300
cctctctgcg cgctcgctcg ctcactgagg ccgggcgacc aaaggtcgcc cgacgcccgg   360
gctttgcccg gcggcctca gtgagcgagc gagcgcgcag ccttaattaa cctaattcac    420
tggccgtcgt tttacaacgt cgtgactggg aaaaccctgg cgttacccaa cttaatcgcc   480
ttgcagcaca tccccctttc gccagctggc gtaatagcga agaggcccgc accgatcgcc   540
cttcccaaca gttgcgcagc ctgaatggcg aatgggacgc gccctgtagc ggcgcattaa   600
gcgcggcggg tgtggtggtt acgcgcagcg tgaccgctac acttgccagc gccctagcgc   660
ccgctccttt cgctttcttc ccttcctttc tcgccacgtt cgccggcttt ccccgtcaag   720
ctctaaatcg ggggctccct ttagggttcc gatttagtgc tttacggcac ctcgacccca   780
```

```
aaaaacttga ttagggtgat ggttcacgta gtgggccatc gccctgatag acggtttttc    840
gcccttttgac gttggagtcc acgttcttta atagtggact cttgttccaa actggaacaa    900
cactcaaccc tatctcggtc tattcttttg atttataagg gattttgccg atttcggcct    960
attggttaaa aaatgagctg atttaacaaa aatttaacgc gaattttaac aaaatattaa   1020
cgcttacaat ttaggtggca cttttcgggg aaatgtgcgc ggaacccta tttgtttatt    1080
tttctaaata cattcaaata tgtatccgct catgagacaa taaccctgat aaatgcttca   1140
ataatattga aaaggaaga gtatgagtat tcaacatttc cgtgtcgccc ttattccctt    1200
ttttgcggca ttttgccttc ctgttttttgc tcacccagaa acgctggtga agtaaaaga    1260
tgctgaagat cagttgggtg cacgagtggg ttacatcgaa ctggatctca acagcggtaa   1320
gatccttgag agtttttcgcc ccgaagaacg ttttccaatg atgagcactt ttaaagttct   1380
gctatgtggc gcggtattat cccgtattga cgccgggcaa gagcaactcg gtcgccgcat   1440
acactattct cagaatgact tggttgagta ctcaccagtc acagaaaagc atcttacgga   1500
tggcatgaca gtaagagaat tatgcagtgc tgccataacc atgagtgata acactgcggc   1560
caacttactt ctgacaacga tcggaggacc gaaggagcta accgcttttt tgcacaacat   1620
gggggatcat gtaactcgcc ttgatcgttg ggaaccggag ctgaatgaag ccataccaaa   1680
cgacgagcgt gacaccacga tgcctgtagc aatggcaaca acgttgcgca aactattaac   1740
tggcgaacta cttactctag cttcccggca acaattaata gactggatgg aggcggataa   1800
agttgcagga ccacttctgc gctcggccct tccggctggc tggtttattg ctgataaatc   1860
tggagccggt gagcgtgggt ctcgcggtat cattgcagca ctggggccag atggtaagcc   1920
ctcccgtatc gtagttatct acacgacggg gagtcaggca actatggatg aacgaaatag   1980
acagatcgct gagataggtg cctcactgat taagcattgg taactgtcag accaagttta   2040
ctcatatata ctttagattg atttaaaact tcatttttaa tttaaaagga tctaggtgaa   2100
gatcctttt gataatctca tgaccaaaat cccttaacgt gagttttcgt tccactgagc   2160
gtcagacccc gtagaaaaga tcaaaggatc ttcttgagat cctttttttc tgcgcgtaat   2220
ctgctgcttg caaacaaaaa aaccaccgct accagcggtg gtttgtttgc cggatcaaga   2280
gctaccaact ctttttccga aggtaactgg cttcagcaga gcgcagatac caaatactgt   2340
tcttctagtg tagccgtagt taggccacca cttcaagaac tctgtagcac cgcctacata   2400
cctcgctctg ctaatcctgt taccagtggc tgctgccagt ggcgataagt cgtgtcttac   2460
cgggttggac tcaagacgat agttaccgga taaggcgcag cggtcgggct gaacggggggg   2520
ttcgtgcaca cagcccagct tggagcgaac gacctacacc gaactgagat acctacagcg   2580
tgagctatga gaaagcgcca cgcttcccga agggagaaag gcggacaggt atccggtaag   2640
cggcagggtc ggaacaggag agcgcacgag ggagcttcca gggggaaacg cctggtatct   2700
ttatagtcct gtcgggtttc gccacctctg acttgagcgt cgatttttgt gatgctcgtc   2760
agggggggcgg agcctatgga aaaacgccag caacgcggcc ttttacggtt cctggccctt   2820
ttgctggcct tttgctcaca tgttctttcc tgcgttatcc cctgattctg tggataaccg   2880
tattaccgcc tttgagtgag ctgataccgc tcgccgcagc cgaacgaccg agcgcagcga   2940
gtcagtgagc gaggaagcgg aagagcgccc aatacgcaaa ccgcctctcc ccgcgcgttg   3000
gccgattcat taatgcagct ggcacgacag gtttcccgac tggaaagcgg gcagtgagcg   3060
caacgcaatt aatgtgagtt agctcactca ttaggcaccc caggctttac actttatgct   3120
tccggctcgt atgttgtgtg gaattgtgag cggataacaa tttcacacag gaaacagcta   3180
```

-continued

```
tgaccatgat tacgccagat ttaattaagg ccttaattag gctgcgcgct cgctcgctca    3240
ctgaggccgc ccgggcaaag cccgggcgtc gggcgacctt tggtcgcccg gcctcagtga    3300
gcgagcgagc gcgcagagag ggagtggcca actccatcac tagggggttcc ttgtagttaa    3360 tgattaaccc gccatgctac ttatctacca gggtaatggg gatcctctag aactatagct    3420
agtcgacatt gattattgac tagttattaa tagtaatcaa ttacggggtc attagttcat    3480
agcccatata tggagttccg cgttacataa cttacggtaa atggcccgcc tggctgaccg    3540
cccaacgacc cccgcccatt gacgtcaata atgacgtatg ttcccatagt aacgccaata    3600
gggactttcc attgacgtca atgggtggac tatttacggt aaactgccca cttggcagta    3660
catcaagtgt atcatatgcc aagtacgccc cctattgacg tcaatgacgg taaatggccc    3720
gcctggcatt atgcccagta catgacctta tgggactttc ctacttggca gtacatctac    3780
gtattagtca tcgctattac catggtcgag gtgagcccca cgttctgctt cactctcccc    3840
atctcccccc cctccccacc cccaattttg tatttattta ttttttaatt attttgtgca    3900 gcgatgggggg cggggggggg gggggggcgc gcgccaggcg gggcggggcg gggcgagggg    3960
cggggcgggg cgaggcggag aggtgcggcg gcagccaatc agagcggcgc gctccgaaag    4020 tttccttta tggcgaggcg gcggcggcgg cggccctata aaaagcgaag cgcgcggcgg    4080
gcggggagtc gctgcgacgc tgccttcgcc ccgtgcccg ctccgccgcc gcctcgcgcc    4140
gcccgccccg gctctgactg accgcgttac tcccacaggt gagcgggcgg gacggccctt    4200
ctcctccggg ctgtaattag cgcttggttt aatgacggct tgtttctttt ctgtggctgc    4260
gtgaaagcct tgagggctc cgggagggcc ctttgtgcgg gggagcggc tcgggggtg    4320 cgtgcgtgtg tgtgtgcgtg gggagcgccg cgtgcggctc cgcgctgccc ggcggctgtg    4380
agcgctgcgg gcgcggcgcg gggctttgtg cgctccgcag tgtgcgcgag gggagcgcgg    4440 ccggggggcgg tgccccgcgg tgcggggggg gctgcgaggg gaacaaaggc tgcgtgcggg    4500
gtgtgtgcgt ggggggggtga gcaggggggtg tgggcgcgtc ggtcgggctg caacccccc    4560 tgcaccccc tccccgagtt gctgagcacg gcccggcttc gggtgcgggg ctccgtacgg    4620
ggcgtggcgc ggggctcgcc gtgccggggcg ggggtggcg gcaggtgggg gtgccgggcg    4680
gggcggggcc gcctcgggcc ggggagggct cggggaggg gcgcggcggc ccccggagcg    4740
ccggcggctg tcgaggcgcg gcgagccgca gccattgcct tttatggtaa tcgtgcgaga    4800
gggcgcaggg acttcctttg tcccaaatct gtgcggagcc gaaatctggg aggcgccgcc    4860 gcacccctc tagcgggcgc ggggcgaagc ggtgcgcgc cggcaggaag gaaatgggcg    4920
gggagggcct tcgtgcgtcg ccgcgccgcc gtcccttct ccctctccag cctcggggct    4980
gtccgcgggg gacgctgc cttcgggggg gacggggcag ggcggggttc ggcttctggc    5040
gtgtgaccgg cggctctaga gcctctgcta accatgttca tgccttcttc tttttcctac    5100
agctcctggg caacgtgctg gttattgtgc tgtctcatca ttttggcaaa gaattcgcca    5160
ccatggccca catcagaggc ctgtggctgc ctggatgtct ggccctggct gccctgtgta    5220
gcctggtgca cagccagcat gtgtttctgg cccctcagca ggccctgagc ctgctgcaga    5280
gagtgcggag acacgccgag ggcacctta cctccgacgt gtccagctac ctggaaggcc    5340
aggccgccaa agagtttatc gcctggctcg tgaagggcag aggctgatga ggtac    5395
```

<210> SEQ ID NO 60
<211> LENGTH: 5428
<212> TYPE: DNA

```
<213> ORGANISM: Artificial Sequence
<220> FEATURE:
<223> OTHER INFORMATION: constructed sequence
<220> FEATURE:
<221> NAME/KEY: polyA_signal
<222> LOCATION: (56)..(182)
<223> OTHER INFORMATION: Rabbit\globin\poly\A
<220> FEATURE:
<221> NAME/KEY: repeat_region
<222> LOCATION: (271)..(400)
<223> OTHER INFORMATION: 3' ITR (complement)
<220> FEATURE:
<221> NAME/KEY: rep_origin
<222> LOCATION: (577)..(1032)
<223> OTHER INFORMATION: F1 ori (Complement)
<220> FEATURE:
<221> NAME/KEY: misc_feature
<222> LOCATION: (1163)..(2020)
<223> OTHER INFORMATION: AP(R)
<220> FEATURE:
<221> NAME/KEY: rep_origin
<222> LOCATION: (2194)..(2784)
<223> OTHER INFORMATION: Origin\of\replication
<220> FEATURE:
<221> NAME/KEY: misc_feature
<222> LOCATION: (3149)..(3800)
<223> OTHER INFORMATION: CMV\IE\promoter
<220> FEATURE:
<221> NAME/KEY: repeat_region
<222> LOCATION: (3222)..(3351)
<223> OTHER INFORMATION: 5' ITR
<220> FEATURE:
<221> NAME/KEY: misc_feature
<222> LOCATION: (3803)..(4084)
<223> OTHER INFORMATION: CB promoter
<220> FEATURE:
<221> NAME/KEY: TATA_signal
<222> LOCATION: (4057)..(4060)
<220> FEATURE:
<221> NAME/KEY: Intron
<222> LOCATION: (4179)..(5151)
<223> OTHER INFORMATION: chicken\beta-actin\intron
<220> FEATURE:
<221> NAME/KEY: misc_feature
<222> LOCATION: (5163)..(5312)
<223> OTHER INFORMATION: leader
<220> FEATURE:
<221> NAME/KEY: misc_feature
<222> LOCATION: (5313)..(5324)
<223> OTHER INFORMATION: furin site
<220> FEATURE:
<221> NAME/KEY: misc_feature
<222> LOCATION: (5325)..(5417)
<223> OTHER INFORMATION: GLP1

<400> SEQUENCE: 60
ctctagagtc gacccgggcg gcctcgagga cggggtgaac tacgcctgag gatccgatct      60 ttttcccttct gccaaaaatt atggggacat catgaagccc cttgagcatc tgacttctgg   120
ctaataaagg aaatttattt tcattgcaat agtgtgttgg aatttttttgt gtctctcact   180 cggaagcaat tcgttgatct gaatttcgac cacccataat acccattacc ctggtagata   240
agtagcatgg cgggttaatc attaactaca aggaacccct agtgatggag ttggccactc   300
cctctctgcg cgctcgctcg ctcactgagg ccgggcgacc aaaggtcgcc cgacgcccgg   360
gctttgcccg gcggcctca gtgagcgagc gagcgcgcag ccttaattaa cctaattcac    420
tggccgtcgt tttacaacgt cgtgactggg aaaaccctgg cgttacccaa cttaatcgcc   480
ttgcagcaca tccccctttc gccagctggc gtaatagcga agaggcccgc accgatcgcc   540
cttcccaaca gttgcgcagc ctgaatggcg aatgggacgc gccctgtagc ggcgcattaa   600
gcgcggcggg tgtggtggtt acgcgcagcg tgaccgctac acttgccagc gccctagcgc   660
```

-continued

```
ccgctcctttt cgctttcttc ccttcctttc tcgccacgtt cgccggcttt ccccgtcaag    720
ctctaaatcg ggggctccct ttagggttcc gatttagtgc tttacggcac ctcgacccca    780
aaaaacttga ttagggtgat ggttcacgta gtgggccatc gccctgatag acggtttttc    840 gcccttttgac gttggagtcc acgttcttta atagtggact cttgttccaa actggaacaa    900
cactcaaccc tatctcggtc tattcttttg atttataagg gattttgccg atttcggcct    960
attggttaaa aaatgagctg atttaacaaa aatttaacgc gaattttaac aaaatattaa   1020
cgcttacaat ttaggtggca cttttcgggg aaatgtgcgc ggaacccta tttgtttatt    1080 tttctaaata cattcaaata tgtatccgct catgagacaa taaccctgat aaatgcttca   1140
ataatattga aaaggaaga gtatgagtat tcaacatttc cgtgtcgccc ttattcccttt   1200 ttttgcggca ttttgccttc ctgttttttgc tcacccagaa acgctggtga agtaaaaga    1260 tgctgaagat cagttgggtg cacgagtggg ttacatcgaa ctggatctca acagcggtaa   1320
gatccttgag agttttcgcc ccgaagaacg ttttccaatg atgagcactt ttaaagttct   1380
gctatgtggc gcggtattat cccgtattga cgccgggcaa gagcaactcg gtcgccgcat   1440
acactattct cagaatgact tggttgagta ctcaccagtc acagaaaagc atcttacgga   1500
tggcatgaca gtaagagaat tatgcagtgc tgccataacc atgagtgata acactgcggc   1560
caacttactt ctgacaacga tcggaggacc gaaggagcta accgcttttt tgcacaacat   1620
gggggatcat gtaactcgcc ttgatcgttg ggaaccggag ctgaatgaag ccataccaaa   1680
cgacgagcgt gacaccacga tgcctgtagc aatggcaaca acgttgcgca aactattaac   1740
tggcgaacta cttactctag cttcccggca acaattaata gactggatgg aggcggataa   1800
agttgcagga ccacttctgc gctcggccct tccggctggc tggtttattg ctgataaatc   1860
tggagccggt gagcgtgggt ctcgcggtat cattgcagca ctggggccag atggtaagcc   1920
ctcccgtatc gtagttatct acacgacggg gagtcaggca actatggatg aacgaaatag   1980
acagatcgct gagataggtg cctcactgat taagcattgg taactgtcag accaagttta   2040
ctcatatata ctttagattg atttaaaact tcatttttaa tttaaaagga tctaggtgaa   2100
gatccttttt gataatctca tgaccaaaat cccttaacgt gagttttcgt tccactgagc   2160
gtcagacccc gtagaaaaga tcaaaggatc ttcttgagat cctttttttc tgcgcgtaat   2220
ctgctgcttg caaacaaaaa aaccaccgct accagcggtg gtttgtttgc cggatcaaga   2280
gctaccaact cttttttccga aggtaactgg cttcagcaga gcgcagatac caaatactgt   2340
tcttctagtg tagccgtagt taggccacca cttcaagaac tctgtagcac cgcctacata   2400
cctcgctctg ctaatcctgt taccagtggc tgctgccagt ggcgataagt cgtgtcttac   2460
cgggttggac tcaagacgat agttaccgga taaggcgcag cggtcgggct gaacggggggg  2520 ttcgtgcaca cagcccagct tggagcgaac gacctacacc gaactgagat acctacagcg   2580
tgagctatga gaaagcgcca cgcttcccga agggagaaag gcggacaggt atccggtaag   2640
cggcagggtc ggaacaggag agcgcacgag ggagcttcca gggggaaacg cctggtatct   2700
ttatagtcct gtcgggtttc gccacctctg acttgagcgt cgatttttgt gatgctcgtc   2760
aggggggcgg agcctatgga aaaacgccag caacgcggcc ttttttacggt tcctggcctt   2820 ttgctggcct tttgctcaca tgttctttcc tgcgttatcc cctgattctg tggataaccg   2880
tattaccgcc tttgagtgag ctgataccgc tcgccgcagc cgaacgaccg agcgcagcga   2940
gtcagtgagc gaggaagcgg aagagcgccc aatacgcaaa ccgcctctcc ccgcgcgttg   3000
gccgattcat taatgcagct ggcacgacag gtttcccgac tggaaagcgg gcagtgagcg   3060
```

```
caacgcaatt aatgtgagtt agctcactca ttaggcaccc caggctttac actttatgct    3120
tccggctcgt atgttgtgtg gaattgtgag cggataacaa tttcacacag gaaacagcta    3180
tgaccatgat tacgccagat ttaattaagg ccttaattag gctgcgcgct cgctcgctca    3240
ctgaggccgc ccgggcaaag cccgggcgtc gggcgacctt tggtcgcccg gcctcagtga    3300
gcgagcgagc gcgcagagag ggagtggcca actccatcac taggggttcc ttgtagttaa    3360
tgattaaccc gccatgctac ttatctacca gggtaatggg gatcctctag aactatagct    3420
agtcgacatt gattattgac tagttattaa tagtaatcaa ttacgggtgc attagttcat    3480
agcccatata tggagttccg cgttacataa cttacggtaa atggcccgcc tggctgaccg    3540
cccaacgacc cccgcccatt gacgtcaata atgacgtatg ttcccatagt aacgccaata    3600
gggactttcc attgacgtca atgggtggac tatttacggt aaactgccca cttggcagta    3660
catcaagtgt atcatatgcc aagtacgccc cctattgacg tcaatgacgg taaatggccc    3720
gcctggcatt atgcccagta catgacctta tgggactttc ctacttggca gtacatctac    3780
gtattagtca tcgctattac catggtcgag gtgagcccca cgttctgctt cactctcccc    3840
atctcccccc cctccccacc cccaattttg tatttattta ttttttaatt attttgtgca    3900
gcgatggggg cggggggggg ggggggcgc gcgccaggcg gggcggggcg gggcgagggg    3960
cggggcgggg cgaggcggag aggtgcggcg gcagccaatc agagcggcgc gctccgaaag    4020
tttcctttta tggcgaggcg gcggcggcgg cggccctata aaaagcgaag cgcgcggcgg    4080
gcggggagtc gctgcgacgc tgccttcgcc ccgtgcccg ctccgccgcc gcctcgcgcc    4140
gcccgccccg gctctgactg accgcgttac tcccacaggt gagcgggcgg gacggccctt    4200
ctcctccggg ctgtaattag cgcttggttt aatgacggct tgtttctttt ctgtggctgc    4260
gtgaaagcct tgagggggctc cgggagggcc ctttgtgcgg gggagcggc tcgggggtg    4320
cgtgcgtgtg tgtgtgcgtg gggagcgccg cgtgcggctc cgcgctgccc ggcggctgtg    4380
agcgctgcgg gcgcggcgcg gggctttgtg cgctccgcag tgtgcgcgag gggagcgcgg    4440
ccggggggcgg tgccccgcgg tgcggggggg gctgcgaggg gaacaaaggc tgcgtgcggg    4500
gtgtgtgcgt gggggggtga gcaggggtg tgggcgcgtc ggtcgggctg caaccccccc    4560
tgcaccccc tccccgagtt gctgagcacg gcccggcttc gggtgcgggg ctccgtacgg    4620
ggcgtggcgc ggggctcgcc gtgccggggcg ggggggtggcg gcaggtgggg gtgccgggcg    4680
gggcggggcc gcctcgggcc gggagggct cgggggaggg gcgcggcggc cccggagcg    4740
ccggcggctg tcgaggcgcg gcgagccgca gccattgcct tttatggtaa tcgtgcgaga    4800
gggcgcaggg acttcctttg tcccaaatct gtgcggagcc gaaatctggg aggcgccgcc    4860
gcacccctc tagcgggcgc ggggcgaagc ggtgcgcgc cggcaggaag gaaatgggcg    4920
gggagggcct tcgtgcgtcg ccgcgccgcc gtccccttct ccctctccag cctcggggct    4980
gtccgcgggg gacgcgctgc cttcgggggg acggggcag ggcggggttc ggcttctggc    5040
gtgtgaccgg cggctctaga gcctctgcta accatgttca tgccttcttc ttttcctac    5100
agctcctggg caacgtgctg gttattgtgc tgtctcatca ttttggcaaa gaattcgcca    5160
ccatgggagc cgatgctaga cctctgggag tgcgggctgg cggcggagga agaggcgctg    5220
caagacctgg cacaagcagc agagcactgc ctccacctct gccccctctg agctttctcc    5280
tgctgctgct ggctgcccct ggcgctagag ccagaaaaag aaggcacgcc gagggcacct    5340
tcaccagcga cgtgtccagc tacctggaag gccaggccgc caaagagttt atcgcctggc    5400
```

```
tcgtgaaggg cagaggctga tgaggtac                                        5428
```

<210> SEQ ID NO 61
<211> LENGTH: 5338
<212> TYPE: DNA
<213> ORGANISM: Artificial Sequence
<220> FEATURE:
<223> OTHER INFORMATION: constructed sequence
<220> FEATURE:
<221> NAME/KEY: polyA_signal
<222> LOCATION: (243)..(369)
<223> OTHER INFORMATION: Rabbit\globin\poly\A
<220> FEATURE:
<221> NAME/KEY: repeat_region
<222> LOCATION: (458)..(587)
<223> OTHER INFORMATION: 3' ITR (complement)
<220> FEATURE:
<221> NAME/KEY: rep_origin
<222> LOCATION: (764)..(1219)
<223> OTHER INFORMATION: f1 ori (complement)
<220> FEATURE:
<221> NAME/KEY: misc_feature
<222> LOCATION: (1350)..(2270)
<223> OTHER INFORMATION: AP(R)
<220> FEATURE:
<221> NAME/KEY: rep_origin
<222> LOCATION: (2381)..(2969)
<223> OTHER INFORMATION: origin of replication
<220> FEATURE:
<221> NAME/KEY: repeat_region
<222> LOCATION: (3409)..(3538)
<223> OTHER INFORMATION: 5' ITR
<220> FEATURE:
<221> NAME/KEY: misc_feature
<222> LOCATION: (3606)..(3987)
<223> OTHER INFORMATION: CMV\IE\promoter
<220> FEATURE:
<221> NAME/KEY: promoter
<222> LOCATION: (3990)..(4271)
<223> OTHER INFORMATION: CB promoter
<220> FEATURE:
<221> NAME/KEY: TATA_signal
<222> LOCATION: (4244)..(4247)
<220> FEATURE:
<221> NAME/KEY: Intron
<222> LOCATION: (4366)..(5338)
<223> OTHER INFORMATION: chicken\beta-actin\intron

<400> SEQUENCE: 61

```
aattcgccac catgaaatgg gtcaccttca tcagcctgct gctgctgttc agcagcgcct     60
acagcagagg cgtgaccaga aggcacgccg agggcacctt taccagcgac gtgtccagct    120
acctggaagg ccaggccgcc aaagagttta tcgcctggct cgtgaagggc aggggctgat    180
gaggtacctc tagagtcgac ccgggcggcc tcgaggacgg ggtgaactac gcctgaggat    240
ccgatctttt tccctctgcc aaaaattatg gggacatcat gaagcccctt gagcatctga    300
cttctggcta taaaggaaa tttatttttca ttgcaatagt gtgttggaat tttttgtgtc    360
tctcactcgg aagcaattcg ttgatctgaa tttcgaccac ccataatacc cattaccctg    420
gtagataagt agcatggcgg gttaatcatt aactacaagg aacccctagt gatggagttg    480
gccactccct ctctgcgcgc tcgctcgctc actgaggccg ggcgaccaaa ggtcgcccga    540
cgcccgggct ttgcccgggc ggcctcagtg agcgagcgag cgcgcagcct taattaacct    600
aattcactgg ccgtcgtttt acaacgtcgt gactgggaaa accctggcgt tacccaactt    660
aatcgccttg cagcacatcc ccctttcgcc agctggcgta atagcgaaga ggcccgcacc    720
gatcgccctt cccaacagtt gcgcagcctg aatggcgaat gggacgcgcc ctgtagcggc    780
gcattaagcg cggcgggtgt ggtggttacg cgcagcgtga ccgctacact tgccagcgcc    840
```

```
ctagcgcccg ctcctttcgc tttcttccct tcctttctcg ccacgttcgc cggctttccc    900
cgtcaagctc taaatcgggg gctcccttta gggttccgat ttagtgcttt acggcacctc    960
gaccccaaaa aacttgatta gggtgatggt tcacgtagtg ggccatcgcc ctgatagacg   1020
gttttttcgcc ctttgacgtt ggagtccacg ttctttaata gtggactctt gttccaaact   1080
ggaacaacac tcaaccctat ctcggtctat tcttttgatt tataagggat tttgccgatt   1140
tcggcctatt ggttaaaaaa tgagctgatt taacaaaaat ttaacgcgaa ttttaacaaa   1200
atattaacgc ttacaatttta ggtggcactt tcggggaaa tgtgcgcgga acccctatttt   1260
gtttatttttt ctaaatacat tcaaatatgt atccgctcat gagacaataa ccctgataaa   1320
tgcttcaata atattgaaaa aggaagagta tgagtattca catttccgt gtcgccctta   1380
ttccctttttt tgcggcattt tgccttcctg ttttttgctca cccagaaacg ctggtgaaag   1440
taaaagatgc tgaagatcag ttgggtgcac gagtgggtta catcgaactg gatctcaaca   1500
gcggtaagat ccttgagagt tttcgccccg aagaacgttt tccaatgatg agcactttta   1560
aagttctgct atgtggcgcg gtattatccc gtattgacgc cgggcaagag caactcggtc   1620
gccgcataca ctattctcag aatgacttgg ttgagtactc accagtcaca gaaaagcatc   1680
ttacggatgg catgacagta agagaattat gcagtgctgc cataaccatg agtgataaca   1740
ctgcggccaa cttacttctg acaacgatcg gaggaccgaa ggagctaacc gcttttttgc   1800
acaacatggg ggatcatgta actcgccttg atcgttggga accggagctg aatgaagcca   1860
taccaaacga cgagcgtgac accacgatgc ctgtagcaat ggcaacaacg ttgcgcaaac   1920
tattaactgg cgaactactt actctagctt cccggcaaca attaatagac tggatggagg   1980
cggataaagt tgcaggacca cttctgcgct cggcccttcc ggctggctgg tttattgctg   2040
ataaatctgg agccggtgag cgtgggtctc gcggtatcat tgcagcactg gggccagatg   2100
gtaagccctc ccgtatcgta gttatctaca cgacggggag tcaggcaact atggatgaac   2160
gaaatagaca gatcgctgag ataggtgcct cactgattaa gcattggtaa ctgtcagacc   2220
aagtttactc atatatactt tagattgatt taaaacttca ttttttaattt aaaaggatct   2280
aggtgaagat cctttttgat aatctcatga ccaaaatccc ttaacgtgag ttttcgttcc   2340
actgagcgtc agaccccgta gaaaagatca aaggatcttc ttgagatcct ttttttctgc   2400
gcgtaatctg ctgcttgcaa acaaaaaaac caccgctacc agcggtggtt tgtttgccgg   2460
atcaagagct accaactctt tttccgaagg taactggctt cagcagagcg cagataccaa   2520
atactgttct tctagtgtag ccgtagttag gccaccactt caagaactct gtagcaccgc   2580
ctacatacct cgctctgcta atcctgttac cagtggctgc tgccagtggc gataagtcgt   2640
gtcttaccgg gttggactca agacgatagt taccggataa ggcgcagcgg tcgggctgaa   2700
cggggggttc gtgcacacag cccagcttgg agcgaacgac ctacaccgaa ctgagatacc   2760
tacagcgtga gctatgagaa agcgccacgc ttcccgaagg gagaaaggcg gacaggtatc   2820
cggtaagcgg cagggtcgga acaggagagc gcacgaggga gcttccaggg ggaaacgcct   2880
ggtatcttta tagtcctgtc gggtttcgcc acctctgact tgagcgtcga ttttttgtgat   2940
gctcgtcagg gggcggagc ctatggaaaa acgccagcaa cgcggccttt ttacggttcc   3000
tggccttttg ctggcctttt gctcacatgt tctttcctgc gttatcccct gattctgtgg   3060
ataaccgtat taccgccttt gagtgagctg ataccgctcg ccgcagccga acgaccgagc   3120
gcagcgagtc agtgagcgag gaagcggaag agcgcccaat acgcaaaccg cctctccccg   3180
cgcgttggcc gattcattaa tgcagctggc acgacaggtt tcccgactgg aaagcgggca   3240
```

```
gtgagcgcaa cgcaattaat gtgagttagc tcactcatta ggcacccag gctttacact      3300 ttatgcttcc ggctcgtatg ttgtgtggaa ttgtgagcgg ataacaattt cacacaggaa      3360
acagctatga ccatgattac gccagattta attaaggcct taattaggct gcgcgctcgc      3420
tcgctcactg aggccgcccg ggcaaagccc gggcgtcggg cgacctttgg tcgcccggcc      3480
tcagtgagcg agcgagcgcg cagagaggga gtggccaact ccatcactag gggttccttg      3540
tagttaatga ttaacccgcc atgctactta tctaccaggg taatgggat cctctagaac       3600 tatagctagt cgacattgat tattgactag ttattaatag taatcaatta cggggtcatt      3660
agttcatagc ccatatatgg agttccgcgt tacataactt acggtaaatg gcccgcctgg      3720
ctgaccgccc aacgaccccc gcccattgac gtcaataatg acgtatgttc ccatagtaac      3780
gccaataggg actttccatt gacgtcaatg ggtggactat ttacggtaaa ctgcccactt      3840
ggcagtacat caagtgtatc atatgccaag tacgccccct attgacgtca atgacggtaa      3900
atggcccgcc tggcattatg cccagtacat gaccttatgg gactttccta cttggcagta      3960
catctacgta ttagtcatcg ctattaccat ggtcgaggtg agccccacgt tctgcttcac      4020
tctccccatc tccccccct ccccacccc aattttgtat ttatttattt tttaattatt       4080
ttgtgcagcg atggggggcgg ggggggggg ggggcgcgcg ccaggcgggg cggggcgggg     4140 cgagggggcgg ggcggggcga ggcggagagg tgcggcggca gccaatcaga gcggcgcgct   4200
ccgaaagttt cctttatgg cgaggcgcg gcggcggcg ccctataaaa agcgaagcgc       4260
gcggcgggcg gggagtcgct gcgacgctgc cttcgcccg tgcccgctc cgccgccgcc       4320 tcgcgccgcc cgccccggct ctgactgacc gcgttactcc cacaggtgag cgggcgggac     4380 ggccttctc ctccgggctg taattagcgc ttggtttaat gacggcttgt ttcttttctg      4440
tggctgcgtg aaagccttga ggggctccgg gaggccctt tgtgcggggg gagcggctcg      4500 ggggtgcgt gcgtgtgtgt gtgcgtgggg agcgccgcgt gcggctccgc gctgcccggc      4560
ggctgtgagc gctgcgggcg cggcgcgggg ctttgtgcgc tccgcagtgt gcgcgagggg     4620
agcgcggccg ggggcggtgc cccgcggtgc ggggggggct gcgagggaa caaaggctgc      4680 gtgcggggtg tgtgcgtggg ggggtgagca ggggtgtgg gcgcgtcggt cgggctgcaa    4740 cccccctgc accccctcc ccgagttgct gagcacggcc cggcttcggg tgcggggctc       4800
cgtacggggc gtggcgcggg gctcgccgtg ccgggcgggg ggtggcggca ggtgggggtg    4860
ccgggcgggg cggggccgcc tcgggccggg gagggctcgg gggagggggcg cggcggcccc   4920 cggagcgccg gcggctgtcg aggcgcggcg agccgcagcc attgcctttt atggtaatcg     4980
tgcgagaggg cgcagggact ccttttgtcc caaatctgtg cggagccgaa atctgggagg     5040
cgccgccgca ccccctctag cgggcgcggg gcgaagcggt gcggcgccgg caggaaggaa     5100
atgggcgggg agggccttcg tgcgtcgccg cgccgccgtc ccttctcc tctccagcct      5160 cggggctgtc cgcggggggga cggctgcctt cgggggggac ggggcagggc ggggttcggc   5220
ttctggcgtg tgaccggcgg ctctagagcc tctgctaacc atgttcatgc cttcttcttt     5280
ttcctacagc tcctgggcaa cgtgctggtt attgtgctgt ctcatcattt tggcaaag       5338
```

<210> SEQ ID NO 62
<211> LENGTH: 5344
<212> TYPE: DNA
<213> ORGANISM: Artificial Sequence
<220> FEATURE:
<223> OTHER INFORMATION: constructed sequence
<220> FEATURE:

```
<221> NAME/KEY: polyA_signal
<222> LOCATION: (56)..(182)
<223> OTHER INFORMATION: Rabbit\globin\poly\A
<220> FEATURE:
<221> NAME/KEY: repeat_region
<222> LOCATION: (271)..(400)
<223> OTHER INFORMATION: 3' ITR (complement)
<220> FEATURE:
<221> NAME/KEY: rep_origin
<222> LOCATION: (577)..(1032)
<223> OTHER INFORMATION: f1 ori (complement)
<220> FEATURE:
<221> NAME/KEY: misc_feature
<222> LOCATION: (1163)..(2020)
<223> OTHER INFORMATION: AP(R)
<220> FEATURE:
<221> NAME/KEY: misc_feature
<222> LOCATION: (2194)..(2782)
<223> OTHER INFORMATION: origin of replication
<220> FEATURE:
<221> NAME/KEY: repeat_region
<222> LOCATION: (3222)..(3351)
<223> OTHER INFORMATION: 5' ITR
<220> FEATURE:
<221> NAME/KEY: misc_feature
<222> LOCATION: (3419)..(3800)
<223> OTHER INFORMATION: CMV\IE\promoter
<220> FEATURE:
<221> NAME/KEY: promoter
<222> LOCATION: (3803)..(4084)
<223> OTHER INFORMATION: CB promoter
<220> FEATURE:
<221> NAME/KEY: TATA_signal
<222> LOCATION: (4057)..(4060)
<220> FEATURE:
<221> NAME/KEY: Intron
<222> LOCATION: (4197)..(5151)
<223> OTHER INFORMATION: chicken\beta-actin\intron
<220> FEATURE:
<221> NAME/KEY: misc_feature
<222> LOCATION: (5163)..(5228)
<223> OTHER INFORMATION: leader
<220> FEATURE:
<221> NAME/KEY: misc_feature
<222> LOCATION: (5229)..(5240)
<223> OTHER INFORMATION: furin site
<220> FEATURE:
<221> NAME/KEY: misc_feature
<222> LOCATION: (5241)..(5333)
<223> OTHER INFORMATION: GLP1

<400> SEQUENCE: 62
ctctagagtc gacccgggcg gcctcgagga cggggtgaac tacgcctgag gatccgatct      60 ttttcccctct gccaaaaatt atggggacat catgaagccc cttgagcatc tgacttctgg    120
ctaataaagg aaatttattt tcattgcaat agtgtgttgg aatttttttgt gtctctcact    180 cggaagcaat tcgttgatct gaatttcgac cacccataat acccattacc ctggtagata    240
agtagcatgg cgggttaatc attaactaca aggaacccct agtgatggag ttggccactc    300
cctctctgcg cgctcgctcg ctcactgagg ccgggcgacc aaaggtcgcc cgacgcccgg    360
gctttgcccg gcggcctca gtgagcgagc gagcgcgcag ccttaattaa cctaattcac     420
tggccgtcgt tttacaacgt cgtgactggg aaaaccctgg cgttacccaa cttaatcgcc    480
ttgcagcaca tccccctttc gccagctggc gtaatagcga agaggcccgc accgatcgcc    540
cttcccaaca gttgcgcagc ctgaatggcg aatgggacgc gccctgtagc ggcgcattaa    600
gcgcggcggg tgtggtggtt acgcgcagcg tgaccgctac acttgccagc gccctagcgc    660
ccgctccttt cgctttcttc ccttcctttc tcgccacgtt cgccggcttt ccccgtcaag    720
ctctaaatcg ggggctccct ttagggttcc gatttagtgc tttacggcac ctcgacccca    780
```

```
aaaaacttga ttagggtgat ggttcacgta gtgggccatc gccctgatag acggtttttc    840
gcccttttgac gttggagtcc acgttcttta atagtggact cttgttccaa actggaacaa    900
cactcaaccc tatctcggtc tattcttttg atttataagg attttgccg atttcggcct    960
attggttaaa aaatgagctg atttaacaaa aatttaacgc gaattttaac aaaatattaa   1020
cgcttacaat ttaggtggca cttttcgggg aaatgtgcgc ggaacccta tttgtttatt   1080
tttctaaata cattcaaata tgtatccgct catgagacaa taaccctgat aaatgcttca   1140
ataatattga aaaggaaga gtatgagtat tcaacatttc cgtgtcgccc ttattccctt   1200
ttttgcggca ttttgccttc ctgttttgc tcacccagaa acgctggtga agtaaaaga    1260
tgctgaagat cagttgggtg cacgagtggg ttacatcgaa ctggatctca acagcggtaa   1320
gatccttgag agttttcgcc ccgaagaacg ttttccaatg atgagcactt ttaaagttct   1380
gctatgtggc gcggtattat cccgtattga cgccgggcaa gagcaactcg gtcgccgcat   1440
acactattct cagaatgact tggttgagta ctcaccagtc acagaaaagc atcttacgga   1500
tggcatgaca gtaagagaat tatgcagtgc tgccataacc atgagtgata acactgcggc   1560
caacttactt ctgacaacga tcggaggacc gaaggagcta accgcttttt tgcacaacat   1620
gggggatcat gtaactcgcc ttgatcgttg ggaaccggag ctgaatgaag ccataccaaa   1680
cgacgagcgt gacaccacga tgcctgtagc aatggcaaca acgttgcgca aactattaac   1740
tggcgaacta cttactctag cttcccggca acaattaata gactggatgg aggcggataa   1800
agttgcagga ccacttctgc gctcggccct tccggctggc tggtttattg ctgataaatc   1860
tggagccggt gagcgtgggt ctcgcggtat cattgcagca ctggggccag atggtaagcc   1920
ctcccgtatc gtagttatct acacgacggg gagtcaggca actatggatg aacgaaatag   1980
acagatcgct gagataggtg cctcactgat taagcattgg taactgtcag accaagttta   2040
ctcatatata ctttagattg atttaaaact tcatttttaa tttaaaagga tctaggtgaa   2100
gatccttttt gataatctca tgaccaaaat cccttaacgt gagttttcgt tccactgagc   2160
gtcagacccc gtagaaaaga tcaaaggatc ttcttgagat cctttttttc tgcgcgtaat   2220
ctgctgcttg caaacaaaaa aaccaccgct accagcggtg gtttgtttgc cggatcaaga   2280
gctaccaact cttttttccga aggtaactgg cttcagcaga gcgcagatac caaatactgt   2340
tcttctagtg tagccgtagt taggccacca cttcaagaac tctgtagcac cgcctacata   2400
cctcgctctg ctaatcctgt taccagtggc tgctgccagt ggcgataagt cgtgtcttac   2460
cgggttggac tcaagacgat agttaccgga taaggcgcag cggtcgggct gaacggggggg   2520
ttcgtgcaca cagcccagct tggagcgaac gacctacacc gaactgagat acctacagcg   2580
tgagctatga gaaagcgcca cgcttcccga agggagaaag gcggacaggt atccggtaag   2640
cggcagggtc ggaacaggag agcgcacgag ggagcttcca gggggaaacg cctggtatct   2700
ttatagtcct gtcgggtttc gccacctctg acttgagcgt cgatttttgt gatgctcgtc   2760
aggggggcgg agcctatgga aaaacgccag caacgcggcc ttttacggt tcctggcctt   2820
ttgctggcct tttgctcaca tgttctttcc tgcgttatcc cctgattctg tggataaccg   2880
tattaccgcc tttgagtgag ctgataccgc tcgccgcagc cgaacgaccg agcgcagcga   2940
gtcagtgagc gaggaagcgg aagagcgccc aatacgcaaa ccgcctctcc ccgcgcgttg   3000
gccgattcat taatgcagct ggcacgacag gtttcccgac tggaaagcgg gcagtgagcg   3060
caacgcaatt aatgtgagtt agctcactca ttaggcaccc caggctttac actttatgct   3120
tccggctcgt atgttgtgtg gaattgtgag cggataacaa tttcacacag gaaacagcta   3180
```

```
tgaccatgat tacgccagat ttaattaagg ccttaattag gctgcgcgct cgctcgctca   3240
ctgaggccgc ccgggcaaag cccgggcgtc gggcgacctt tggtcgcccg gcctcagtga   3300
gcgagcgagc gcgcagagag ggagtggcca actccatcac tagggggttcc ttgtagttaa   3360 tgattaaccc gccatgctac ttatctacca gggtaatggg gatcctctag aactatagct   3420
agtcgacatt gattattgac tagttattaa tagtaatcaa ttacggggtc attagttcat   3480
agcccatata tggagttccg cgttacataa cttacggtaa atggcccgcc tggctgaccg   3540
cccaacgacc cccgcccatt gacgtcaata atgacgtatg ttcccatagt aacgccaata   3600
gggactttcc attgacgtca atgggtggac tatttacggt aaactgccca cttggcagta   3660
catcaagtgt atcatatgcc aagtacgccc cctattgacg tcaatgacgg taaatggccc   3720
gcctggcatt atgcccagta catgacctta tgggactttc ctacttggca gtacatctac   3780
gtattagtca tcgctattac catggtcgag gtgagcccca cgttctgctt cactctcccc   3840
atctcccccc cctccccacc cccaattttg tatttattta ttttttaatt attttgtgca   3900
gcgatggggg cggggggggg ggggggcgc gcgccaggcg gggcggggcg gggcgagggg   3960
cggggcgggg cgaggcggag aggtgcggcg gcagccaatc agagcggcgc gctccgaaag   4020
tttcctttta tggcgaggcg gcggcggcgg cggccctata aaaagcgaag cgcgcggcgg   4080
gcggggagtc gctgcgacgc tgccttcgcc ccgtgccccg ctccgccgcc gcctcgcgcc   4140
gcccgccccg gctctgactg accgcgttac tcccacaggt gagcgggcgg gacggccctt   4200
ctcctccggg ctgtaattag cgcttggttt aatgacggct tgtttctttt ctgtggctgc   4260
gtgaaagcct tgaggggctc cggggaggcc ctttgtgcgg ggggagcggc tcggggggtg   4320
cgtgcgtgtg tgtgtgcgtg gggagcgccg cgtgcggctc cgcgctgccc ggcggctgtg   4380
agcgctgcgg gcgcggcgcg gggctttgtg cgctccgcag tgtgcgcgag gggagcgcgg   4440 ccggggggcgg tgccccgcgg tgcggggggg gctgcgaggg gaacaaaggc tgcgtgcggg   4500
gtgtgtgcgt ggggggggtga gcaggggggtg tgggcgcgtc ggtcgggctg caacccccccc   4560 tgcaccccc tccccgagtt gctgagcacg gcccggcttc gggtgcgggg ctccgtacgg   4620
ggcgtggcgc ggggctcgcc gtgccggcg ggggtggcg gcaggtgggg gtgccgggcg   4680
gggcggggcc gcctcgggcc ggggagggct cggggagggg gcgcggcggc ccccggagcg   4740
ccggcggctg tcgaggcgcg gcgagccgca gccattgcct tttatggtaa tcgtgcgaga   4800
gggcgcaggg acttcctttg tcccaaatct gtgcggagcc gaaatctggg aggcgccgcc   4860
gcaccccctc tagcgggcgc ggggcgaagc ggtgcggcgc cggcaggaag gaaatgggcg   4920
gggagggcct tcgtgcgtcg ccgcgccgcc gtccccttct ccctctccag cctcggggct   4980
gtccgcgggg ggacgctgc cttcgggggg gacggggcag ggcggggttc ggcttctggc   5040
gtgtgaccgg cggctctaga gcctctgcta accatgttca tgccttcttc ttttccctac   5100
agctcctggg caacgtgctg gttattgtgc tgtctcatca ttttggcaaa gaattcgcca   5160
ccatgaaatg ggtcaccttc atcagcctgc tgctgctgtt cagcagcgcc tacagcagag   5220
gcgtgaccag aagaaagaga cacgccgagg gcaccttcac cagcgacgtg tcctcttacc   5280
tggaaggcca ggccgccaaa gagtttatcg cctggctcgt gaagggcagg ggctgatgag   5340
gtac                                                                5344
```